United States Patent [19]

Jung et al.

[11] Patent Number: 4,492,692
[45] Date of Patent: Jan. 8, 1985

[54] CEPHALOSPORIN DERIVATIVES

[75] Inventors: Frederic H. Jung, Rilly la Montagne, France; Gareth M. Davies, Cheshire, England

[73] Assignees: Imperial Chemical Industries PLC, London, England; ICI Pharma, Enghien-les-Bains, France

[21] Appl. No.: 333,570

[22] Filed: Dec. 22, 1981

[30] Foreign Application Priority Data

Dec. 22, 1980 [FR] France ................. 80 27254

[51] Int. Cl.$^3$ ................. A61K 31/545; C07D 501/56
[52] U.S. Cl. .................. 424/246; 544/22; 544/25; 544/27; 544/28; 544/90; 544/92
[58] Field of Search ............ 424/246, 248.4; 544/28, 544/90, 92, 22, 25, 27

[56] References Cited

U.S. PATENT DOCUMENTS 4,358,447 11/1982 Hannah ................. 544/27

FOREIGN PATENT DOCUMENTS 0031708 7/1981 European Pat. Off. .

Primary Examiner—Paul M. Coughlan, Jr.
Attorney, Agent, or Firm—Cushman, Darby & Cushman

[57] ABSTRACT

A cephalosporin derivative of the formula:

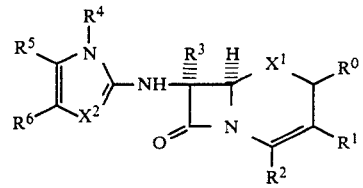

in which $R^0$ is a hydrogen atom or a methyl radical, $R^1$ is any one of the C-3 substituents from antibacterially-active cephalosporins known in the art; $R^2$ is any one of the C-4 substituents from antibacterially-active cephalosporins known in the art; $R^3$ is a hydrogen atom or a 1-6C alkoxy or 1-6C alkylthio radical; $X^1$ is a sulphur or oxygen atom, a $CH_2$ radical or a radical of the formula $NR^7$ in which $R^7$ is a hydrogen atom, a 1-6C alkyl, formyl or benzyl radical; $X^2$ is a nitrogen atom or a radical of the formula $N^{\oplus}$-$R^7$; $R^4$ and $R^7$, and $R^5$ and $R^6$ are a variety of substituents which are described in the specification; and the pharmaceutically-acceptable acid- or base-addition salts thereof. Pharmaceutical compositions, manufacturing processes and intermediates are also described.

9 Claims, No Drawings

CEPHALOSPORIN DERIVATIVES

This invention relates to cephalosporin derivatives which have antibacterial properties.

The vast majority of therapeutically useful antibiotics based on the penicillin and cephalosporin ring systems have an acylamino radical at the 6β and 7β positions respectively. A number of other substituents at these positions have been investigated but in the main the resulting compounds have at best possessed only weak antibacterial activity. One exception to this generalisation is the amidino substituent. Penicillin derivatives carrying a substituted amidino radical in the 6β position (see for example U.K. Pat. Nos. 1,315,566 and 1,406,732) have been found to have useful antibacterial activity and two such compounds, mecillinam and pivmecillinam, are commercially available. However, the corresponding cephalosporin derivatives have been found to have a surprisingly low level of antibacterial activity. European Patent Publication No. 18595 describes a series of cephalosporin derivatives carrying a 2- or 4-pyridinioamino radical in the 7-position.

European Patent Publication No. 31708 describes a series of caphalosporin derivatives carrying a 7-(imidazolin-2-yl)amino or 7-(imidazo-2-yl)amino radical. The present application represents an extension of this work to a variety of substituted imidazole derivatives.

According to the invention there is provided a cephalosporin derivative of the formula:

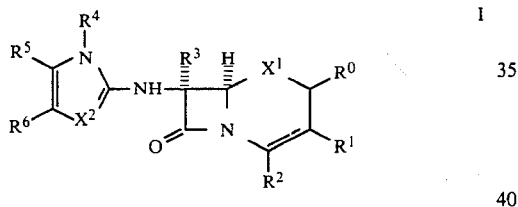

in which $R^0$ is a hydrogen atom or a methyl radical;

$R^1$ is any one of the C-3 substituents from antibacterially-active cephalosporins known in the art;

$R^2$ is any one of the C-4 substituents from antibacterially-active cephalosporins known in the art;

$R^3$ is a hydrogen atom or a 1–6C alkoxy or 1–6C alkylthio radical;

$X^1$ is a sulphur or oxygen atom, a $CH_2$ radical or a radical of the formula $NR^7$ in which $R^7$ is a hydrogen atom, a 1–6C alkyl, formyl or benzyl radical;

$X^2$ is a nitrogen atom or a radical of the formula $N^{\oplus}$-$R^8$;

$R^4$ and $R^8$, which may be the same or different, are hydrogen atoms or 1–6C alkyl, 1–6C alkanoyl, hydroxy, 1–6C alkoxy, amino, 1–6C alkanoylamino, 1–6C alkylamino, 1–6C aminoalkyl, 1–6C hydroxyalkyl, 2–6C carboxyalkyl, 2–6C alkenyl, 3–6C alkoxyalkyl, 3–8C alkoxycarbonylalkyl, furylmethyl, phenyl, 7–11C phenylalkyl,
in the latter two of which the phenyl ring is optionally substituted by a halogen atom or by a methyl, methoxy, nitro, hydroxy, amino, carboxy or methoxycarbonyl radical, 3–6C alkynyl, 3–6C alkadienyl or 9–16C arylalkenyl radicals;

$R^5$ and $R^6$, which may be the same or different, are 1–6C haloalkyl, 1–6C azidoalkyl, 2–6C cyanoalkyl, 2–6C carboxyalkyl, 3–8C alkoxycarbonylalkyl, 2–6C carbamoylalkyl, 3–8C alkylcarbamoylalkyl, 4–10C dialkylcarbamoylalkyl, 2–6C (amino)(carboxy)alkyl, 2–6C alkenyl, 2–6C nitroalkenyl, 8–15C arylalkenyl, 14–25C diarylalkenyl, 20–35C triarylalkenyl, 1–6C alkylthio, 2–6C aminoalkylthio, 3–8C alkylaminoalkylthio, 4–12C dialkylaminoalkylthio, 2–6C aminoalkoxy, 3–8C alkylaminoalkoxy, 4–12C dialkylaminoalkoxy, 6–10C arylthio, 6–10C aryloxy, 7–11C arylalkyl, amino, 1–6C alkylamino, 2–8C dialkylamino, 6–10C arylamino, 7–11C arylalkylamino, 12–20C diarylamino, 1–6C alkanoyl, 7–11C aroyl, 2–6C alkoxycarbonylamino, 7–11C aryloxycarbonylamino, 2–6C alkoxythiocarbonylamino, 7–11C aryloxythiocarbonylamino, 1–6C alkanoylamino, 7–11C aroylamino, 2–6C alkylureido, 7–11C arylureido, 3–8C hydroxyalkenyl, carbamoyl, 2–6C alkylcarbamoyl, 3–8C dialkylcarbamoyl, 5–10C (dialkylaminoalkyl)carbamoyl, 7–11C arylcarbamoyl, thiocarbamoyl, 2–6C (alkyl)thiocarbamoyl, 3–8C (dialkyl)thiocarbamoyl, 7–11C (aryl)thiocarbamoyl, 5–10C (dialkylaminoalkyl)thiocarbamoyl, 2–6C alkoxyalkyl, 2–6C alkanoyloxyalkyl, 2–6C carbamoyloxyalkyl, 3–8C alkylcarbamoyloxyalkyl, 4–12C dialkylcarbamoyloxyalkyl, 7–11C (aryl)(hydroxy)alkyl, 7–11C (aryl)(amino)alkyl, 2–6C alkanoylaminoalkyl, 3–8C haloalkanoylaminoalkyl, 8–15C aroylaminoalkyl, 2–6C ureidoalkyl, 3–8C (alkylureido)alkyl, 4–12C (dialkylureido)alkyl, 8–15C (arylureido)alkyl, guanidinoalkyl, 2–6C formimidoylaminoalkyl, 3–8C alkylimidoylaminoalkyl, 1–6C alkoxy, 2–6C formylalkyl, 2–10C alkanesulphonylaminoalkyl, 7–15C arenesulphonylaminoalkyl, 2–6C alkyl substituted on different carbon atoms by two radicals selected from hydroxy, nitro, amino, 1–6C alkylamino, 2–8C dialkylamino, 6–10C arylamino, 7–11C arylalkylamino, 7–15C (aryl)(alkyl)amino, 8–20C (arylalkyl)(alkyl)amino, pyrrolidino, piperidino, piperazino, N-methylpiperazino, morpholino, 1–6C alkoxy, 1–6C alkylthio, 6–10C aryloxy, 6–10C arylthio, 7–11C arylalkoxy and 7–11C arylalkylthio radicals, 2–6C alkyl radicals substituted on one carbon atom by a nitro, amino, 1–6C alkylamino, 2–10C dialkylamino or 1–6C alkanoylamino radical and on a different carbon atom by a methyl radical which is itself substituted by two radicals selected from cyano, 2–6C alkoxycarbonyl and 1–6C alkanoyl radicals, radicals of the formula:

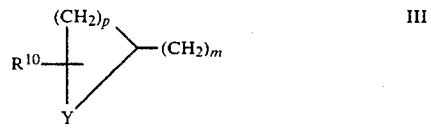

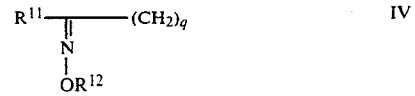

-continued

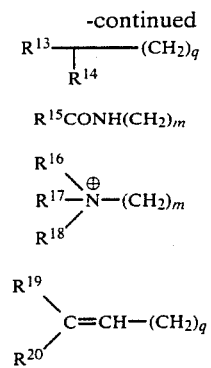

in which Y is an oxygen or sulphur atom or a $CH_2$ radical, m is 1 to 6, q is 0 to 6, n is 0 to 2, p is 1 to 4, $R^9$ is a 1–6C alkyl, 6–10C aryl or 7–11C aralkyl radical, $R^{10}$ is a hydrogen atom or a 1–6C alkyl or 6–10C aryl radical, $R^{11}$ is a hydrogen atom or a 1–6C alkyl, 6–10C aryl, 7–11C arylalkyl or heterocyclyl radical, $R^{12}$ is a hydrogen atom or a 1–6C alkyl radical which is optionally substituted by a carboxy, 2–6C alkoxycarbonyl, carbamoyl or cyano radical, $R^{13}$ is a heterocyclyl radical, $R^{14}$ is a hydroxy or amino radical, $R^{15}$ is a pyridyl radical, $R^{16}$, $R^{17}$ and $R^{18}$, which may be the same or different, are hydrogen atoms or 1–6C alkyl or 6–10C aryl radicals and $R^{19}$ and $R^{20}$ which may be the same or different, are cyano, nitro, 2–6C alkoxycarbonyl, 7–11C aryloxycarbonyl, 1–6C alkanoyl or 7–11C aroyl radicals, or $R^5$ and $R^6$ are heterocyclic radicals which are linked (to the imidazole ring) by a direct bond or by a methylene or thiomethylene ($SCH_2$) bridge, or $R^5$ and $R^6$ are hydrogen or halogen atoms or 1–6C alkyl, cyano, hydroxy, carboxy, 2–6C alkoxycarbonyl, 1–6C aminoalkyl, 2–10C alkylaminoalkyl, 3–15C dialkylaminoalkyl or 1–6C hydroxyalkyl radicals, or phenyl radicals optionally substituted by
1 or 2 radicals selected from halogen atoms and nitro, amino, hydroxy, carboxy, cyano, 1–6C alkyl and 2–6C alkoxycarbonyl radicals, or $R^5$ and $R^6$ are 1–6C nitroalkyl, 4–8C alkadienyl, 4–8C alkenynyl, 3–10C alkoxycarbonylaminoalkyl, 3–10C alkylcarbamoylalkyl, 4–15C dialkylcarbamoylalkyl, 8–15C arylcarbamoylalkyl, 3–15C heterocyclylcarbonylaminoalkyl, 4–15C heterocyclylalkylcarbonylaminoalkyl, 3–10C alkanoylcarbamoyloxyalkyl, 9–18C aroylcarbamoyloxyalkyl, 4–15C heterocyclylcarbonylcarbamoyloxyalkyl, 8–18C arylcarbamoyloxyalkyl, 3–15C heterocyclylcarbamoyloxyalkyl, 3–10C (haloalkylureido)alkyl, 8–18C (arylureido)alkyl, 3–15C (heterorcyclylureido)alkyl, 3–10C [alkyl(thioureido)]alkyl, 3–10C [haloalkyl(thioureido)]alkyl, 8–18C [aryl(thioureido)]alkyl, 3–15C [heterocyclyl(thioureido)alkyl, 1-aminocyanomethyl, 1-dimethylaminocyanomethyl or N-trifluoroacetyl-N-benzylaminomethyl radicals or radicals of the formula:

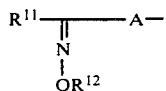     IX

-continued

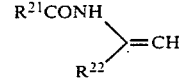     X

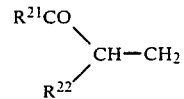     XI in which $R^{11}$ and $R^{12}$ have the meanings given above, A is a 2–6C alkenylene radical, $R^{21}$ is a hydrogen atom or a 1–6C alkyl, 6–10C aryl or 4–7C cycloalkyl radical and $R^{22}$ is a carboxy, carbamoyl, 2–6C alkoxycarbonyl or toluene-p-sulphonyl radical, wherein when $R^5$ or $R^6$ contains an aryl radical, that aryl radical may optionally be substituted by 1 or 2 substituents selected from halogen atoms and nitro, amino, hydroxy, carboxy, cyano, 1–6C alkyl, 2–6C alkoxycarbonyl, sulpho, 1–6C alkoxy, 1–6C haloalkyl, 1–6C alkylsulphamoyl, 2–8C dialkylsulphamoyl and 2–8C dialkylamino radicals, and wherein when $R^5$ or $R^6$ contains a heterocyclic radical that radical is a 5- or 6-membered aromatic or non-aromatic heterocyclic radical which contains 1, 2, 3 or 4 hetero atoms selected from oxygen, nitrogen and sulphur atoms, such ring, where possible, optionally being in the form of the N-oxide and such ring being optionally fused with a benzene ring, and such fused benzene ring and/or (where possible) the heterocyclic ring being optionally substituted by one or two substituents selected from halogen atoms and 1–6C alkyl, hydroxy, 1–6C akoxy, phenoxy, mercapto, 1–6C alkylthio, phenylthio, carboxy, 2–6C alkoxycarbonyl, phenoxycarbonyl, carbamoyl, 2–6C alkylcarbamoyl, 3–10C dialkylcarbamoyl, phenylcarbamoyl, diphenylcarbamoyl, nitro, amino, 1–6C alkylamino, 2–8C dialkylamino, phenylamino, 7–12C (phenyl)(alkyl)amino, diphenylamino, carboxyamino, 2–6C (carboxy)(alkyl)amino, (carboxy)(phenyl)amino, 1–6C alkanoylamino, 2–10C (alkanoyl(alkyl)amino, benzoylamino, 8–14C (benzoyl)(alkyl)amino, cyano, phenyl, sulphamoyl, 1–6C alkylsulphamoyl, 2–10C dialkylsulphamoyl, phenylsulphamoyl, 1–6C haloalkyl, 1–6C aminoalkyl, 2–8C alkylaminoalkyl, 3–12C dialkylaminoalkyl, 2–6C carboxyalkyl, 1–6C sulphoalkyl and oxo radicals, provided that when $X^1$ is a sulphur atom, $X^2$ is a nitrogen atom or $N^{\oplus}$-$R^8$ in which $R^8$ is a hydrogen atom, $R^3$ is a hydrogen atom and $R^4$ is a hydrogen atom or an alkyl, alkanoyl, hydroxy, alkoxy, amino, alkanoylamino, alkylamino, phenyl or phenylalkyl radical, the latter two being optionally substituted on the phenyl ring by a methoxy radical, then $R^5$ and $R^6$ cannot both be selected from the group consisting of hydrogen and halogen atoms and cyano, carboxy, alkoxycarbonyl, aminoalkyl, alkylaminoalkyl, dialkylaminoalkyl, hydroxyalkyl and pyridyl radicals and phenyl radicals optionally substituted by 1 or 2 radicals selected from halogen atoms and nitro, amino, hydroxy, carboxy, cyano, alkyl and alkoxycarbonyl radicals, and provided that when $R^o$ is a methyl radical then $R^1$ is a hydrogen atom and $X^1$ is a sulphur or oxygen atom;

and, where the compound of the formula I contains a free basic or acidic group, the pharmaceutically-acceptable acid- or base-addition salts thereof.

It is to be understood that in the above formula I and throughout this specification the illustrated stereochemistry of the ceph-3-em nucleus of the formula:

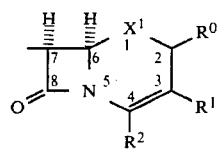

XII is the absolute configuration. It is also to be understood that although the double bonds in the imidazole ring in formula I have been inserted in particular positions, other tautomeric forms are, in certain instances, possible, and these other forms are included within the scope of this invention. Note, however, that the $\Delta^3$ double bond between $R^1$ and $R^2$ in formula I is fixed in position. It is also to be understood that when the compound of the formula I contains both an acidic and basic centre, the compound may exist in the form of a zwitterion.

The characterising feature of the present invention is the nature of the 7β-substituent on the cephalosporin nucleus. $R^1$ may thus be a hydrogen or halogen atom (e.g. a fluorine, chlorine or bromine atom), a hydroxy or amino radical or a saturated or unsaturated, substituted or unsubstituted 1-20C organic group. Illustrative values for $R^1$ when it is a 1-20C organic group are as follows:

(a) 1-6C alkyl, benzyl optionally substituted by fluorine or methoxy, 1-6C haloalkyl, formyl, carboxy, 1-6C alkoxy, 1-6C methylthio, 1-6C alkylamino, phenylamino, benzylamino, 3-6C cycloalkylamino, cyano, 2-6C alkoxycarbonyl, 2-6C alkanoyl, 3-10C alkoxycarbonylalkyl, 2-6C alkoxycarbonylamino, 2-6C alkylthiocarbonylamino, piperidino, pyrrolidino, morpholino, 2-6C alkanoylamino, ureido, 2-6C alkylureido, 3-8C dialkylureido, 1-6C alkanesulphinyl, 1-6C alkanesulphonyl, heterocyclyl and heterocyclylthio radicals in which the heterocycle is a 1,3,4-thiadiazol-2-yl or 1,3,4-oxadiazol-2-yl, each optionally substituted in the 5-position, a 1H-tetrazol-5-yl optionally substituted in the 1-position, or a 1H-1,2,3-triazol-4-yl radical optionally substituted in the 1 or 5 position, the optional substituents in each of these heterocycles being a 1-6C alkyl, a 1-6C sulphoalkyl, a 2-6C carboxyalkyl, a 1-6C haloalkyl or a 3-6C alkylthioalkyl radical or a pyridazin-3-yl, oxazol-3-yl or thiazol-3-yl each optionally substituted by 1 or 2 radicals selected from 1-6C alkyl, 1-6C haloalkyl and 2-6C alkoxycarbonyl radicals;

(b) radicals of the formula:

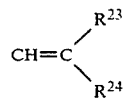

XIII in which $R^{23}$ and $R^{24}$, which may be the same or different, are hydrogen atoms, 1-6C alkyl, 5-7C cycloaliphatic, 6-12C aryl, 7-10C arylalkyl, (e.g. benzyl, 2-phenethyl), formyl, cyano, carboxy, 2-6C alkoxycarbonyl, sulpho, 1-6C alkanesulphinyl, 1-6C alkanesulphonyl, 1-6C alkoxy, 1-6C alkylthio, carbamoyl, nitro, 1-6C hydroxyalkyl, methylcarbamoyloxymethyl, benzylcarbamoyloxymethyl, 2-6C alkoxymethyl, 2-6C alkylthiomethyl, 2-haloethoxymethyl, cyclopentyloxymethyl, benzyloxymethyl or 3-8C alkanoyloxymethyl radicals or radicals of the formula $CH_2SHet^1$ in which $Het^1$ is a 1,3,4-thiadiazol-2-yl or 1,3,4-oxadiazol-2-yl, both optionally substituted in the 5-position by a methyl radical, a 1H-triazol-5-yl radical optionally substituted in the 1-position by a methyl radical or a 1H-1,2,3-triazol-4-yl radical;

(c) radicals of the formula:

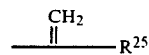

XIV in which $R^{25}$ is a cyano, carboxy or 2-6C alkoxycarbonyl radical;

(d) radicals of the formula:

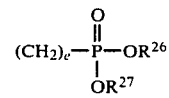

XV in which $R^{26}$ and $R^{27}$, which may be the same or different, are hydrogen atoms or 1-6C alkyl radicals and e is 1 to 4; and (e) radicals of the formula $CH_2Y$ in which Y is an atom or group which is the residue of a nucleophile or a derivative of a residue of a nucleophile, such a nucleophile or a derivative thereof being:

A. 3-15C trialkylamines;
B. heterocyclic amines having more than one heteroatom, at least heteroatom being nitrogen;
C. pyridines which are optionally substituted by 1 to 3 substituents selected from halogen atoms, and 1-6C alkyl, 6-10C aryl, 7-11C arylalkyl, 2-10C alkoxyalkyl, 3-10C alkanoyloxymethyl, formyl, carbamoyl, 2-6C alkanoyloxy, 2-6C alkoxycarbonyl, 1-6C alkoxy, 6-10C aryloxy, 7-11C aralkoxy, 1-6C alkylthio, 6-10C arylthio, 7-11C aralkylthio, cyano, hydroxy, 2-6C alkylcarbamoyl, 3-10C dialkylcarbamoyl, 2-6C (hydroxyalkyl) carbamoyl and 2-6C carbamoylalkyl radicals;
D. azide radicals;
E. amino, 1-6C alkanoylamino and 7-11C aroylamino radicals;
F. cyanide, pyrroles and substituted pyrroles;
G. nucleophiles giving rise to $R^1$ of the formula:

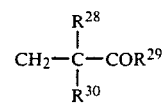

XVI in which $R^{28}$ and $R^{29}$, which may be the same or different, are selected from hydrogen atoms and cyano, 1-6C alkyl, 2-6C alkoxycarbonyl, 8-20C mono- or di-arylalkoxycarbonyl, 2-6C alkanoyl, 7-11C aralkyl, cyclopentyl and cyclohexyl radicals, and phenyl radicals optionally substituted by 1 or 2 radicals selected from halogen atoms and 1-6C alkyl, 1-6C alkoxy, 1-6C alkylamino, nitro and amino radicals, and $R^{30}$ is selected from hydrogen, 1-6C alkyl, 7-11C aralkyl, cyclopentyl and cyclohexyl radicals, and phenyl radicals optionally substituted by 1 or 2 radicals selected from halogen atoms, 1–6C alkyl, 1–6C alkoxy and 1–6C alkylamino radicals;

H. thiourea optionally substituted by a 1–6C alkyl, 6–10C aryl, 5–7C alicyclic or a heterocyclic radical, dithiocarbamates, thioamides substituted by a 1–6C alkyl or 6–10C aryl radical or thiosemicarbazides, thiosulphates, arylthioacids or heterocyclicthioacids of up to 10 carbon atoms and dithioacids of the formula:

       XVII in which $R^{31}$ and $R^{32}$ which may be the same or different, are hydrogen atoms, 1–6C alkyl, 2–6C hydroxyalkyl, 3–8C alkylaminoalkyl, 4–10C dialkylaminoalkyl or phenyl radicals, or $R^{31}$ and $R^{32}$ are joined to form a pyrrolidine, piperidine or morpholine ring or a piperazine ring which is optionally substituted on the nitrogen atom by one or two (in quaternised form) radicals selected from 1–6C alkyl and 3–6C alkenyl radicals;

I. compounds of the formula $R^{33}S(O)_dH$ in which d is 0, 1 or 2 and $R^{33}$ is a 1–6C alkyl, 5–7C alicyclic, 6–10C aryl optionally substituted by a carboxy radical, or 7–11C arylalkyl radical or a 5- or 6-membered heterocyclic ring (partially or fully unsaturated) containing 1 to 4 nitrogen atoms which ring may further include (where possible) oxygen and/or sulphur atoms, in which the nitrogen atom or atoms may be in the oxide form, which heterocyclic ring may be fused with another heterocyclic ring within the same definition or may be fused with a benzene ring, the above aryl, arylalkyl, heterocyclic or fused benzene ring being optionally substituted (where possible) by 1 or 2 substituents selected from halogen atoms and 1–6C alkyl, 1–6C haloalkyl, 6–10C aryl, 2–6C alkenyl, 1–6C alkoxy, oxo, hydroxy, mercapto, amino, carboxy, cyano, isothiocyanato, carbamoyl, sulphamoyl, 2–6C alkoxycarbonyl, 3–6C alkenyloxycarbonyl, 8–12C aralkylcarbonyl, 7–11C aryloxycarbonyl, 2–6C hydroxyalkyl, 3–6C dihydroxyalkyl, sulphoamino and 1–6C alkanesulphonylamino radicals and radicals of the formula B-$R^{34}$ in which B is a 2–8C straight or branched chain which may be interrupted by a sulphur or oxygen atom or by an NH or 1–6C N-alkyl radical and $R^{34}$ is a radical selected from hydroxy, mercapto, cyano, 1–6C alkylamino, 2–6C dialkylamino, 2–6C alkanoylamino, carboxy, sulpho, carbamoyl, sulphamoyl, amidino, guanidino, 2–6C alkoxycarbonyl, 2–6C alkylcarbamoyl, 2–6C dialkylcarbamoyl, 1–6C alkylsulphamoyl, 2–6C dialkylsulphamoyl, sulphoamino, ureido, 1–6C alkoxy, 1–6C alkylthio, 1–6C alkanesulphonyl, 2–6C alkanoyl and 2–6C alkanoyloxy radicals and radicals of the formula —S—$R^{35}$ in which $R^{35}$ is a 1–6C alkyl radical or a group of the formula B-$R^{34}$ in which B and $R^{34}$ have the meanings given above and radicals of the formula $NR^{36}R^{37}$ in which $R^{36}$ and $R^{37}$, which may be the same or different, are selected from 1–6C alkyl radicals, groups of the formula B-$R^{34}$ in which B and $R^{34}$ have the definitions given above, 1–6C alkoxycarbonyl, 2–6C alkanoyl, carbamoyl, 2–6C alkylcarbamoyl and 3–10C dialkylcarbamoyl radicals;

J. radicals of the formula $R^{38}$—OH in which $R^{38}$ is a hydrogen atom, or a 1–6C alkyl, 3–6C alkenyl, 3–6C alkynyl, 5–7C cycloalkyl, 6–12C cycloalkylalkyl, 6–10C aryl, 7–11C arylalkyl or furfuryl radical, any of which may be substituted by 1 or 2 radicals selected from halogen atoms, and 1–6C alkyl, nitro, hydroxy, carboxy, 2–6C alkanoyloxy, 2–6C alkoxcarbonyl, 2–6C alkanoyl, 1–6C alkanesulphonyl, 1–6C alkoxysulphonyl, amino, 1–6C alkylamino and 2–6C alkanoylamino radicals or $R^{38}$ is a carbamoyl radical;

K. radicals of the formula $R^{39}$—Q—COOH in which Q is a direct bond, an oxygen or sulphur atom or an NH radical and $R^{39}$ is:

(i) a hydrogen atom or a 1–6C alkyl radical which may be interrupted by an oxygen or sulphur atom or by an NH group or substituted by a cyano, carboxy, methoxycarbonyl, ethoxycarbonyl, hydroxy, carboxycarbonyl, halogen or amino radical;

(ii) a 2–6C alkenyl radical which may be interrupted by an oxygen or sulphur atom or an NH group;

(iii) a phenyl, hydroxyphenyl, chlorophenyl, fluorophenyl, tolyl, nitrophenyl, aminophenyl, methoxyphenyl, methylthiophenyl, thienyl, pyridyl, cyclohexyl, cyclopentyl, sydnonyl, naphthyl or ethoxynaphthyl radical; or (iv) $R^{40}$—$(CH_2)_g$ where $R^{40}$ has the value for $R^{39}$ listed in (i) above and g is 1 to 4.

A particular value for $R^2$ is a carboxy radical, a radical of the formula:

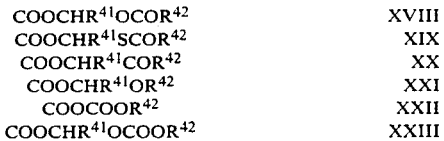

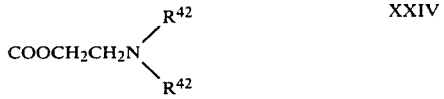

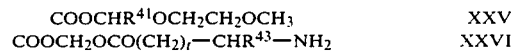

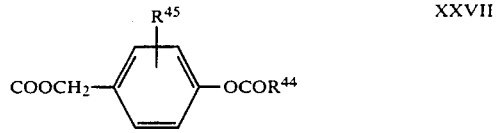

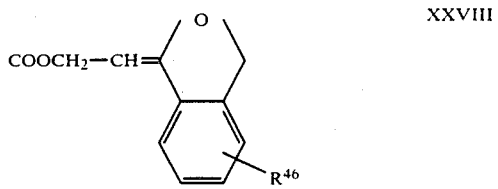

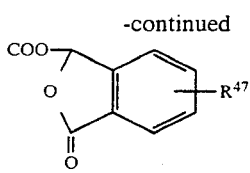

in which $R^{41}$ is a hydrogen atom or 1–6C alkyl radical, $R^{42}$ is a 1–6C alkyl radical, $R^{43}$ is a hydrogen atom, or a 1–6C alkyl, 7–11C arylalkyl or 2–6C alkoxycarbonyl radical, t is 0 or 1, $R^{44}$ is a 1–6C alkyl, 6–10C aryl or a 7–11C aralkyl radical, $R^{45}$ is a hydrogen atom or one, two or three radicals selected from halogen atoms and nitro, cyano, 1–6C alkyl, 1–6C alkoxy, 1–6C alkylthio, 1–6C alkylsulphinyl, 1–6C alkanesulphonyl, 2–6C alkoxycarbonyl, 2–6C alkoxythiocarbonyl, 2–6C alkanoylamino, 6–10C aryl, 6–10C aryloxy, 6–10C arylthio, arylsulphinyl 6–10C arylsulphonyl, 7–11C aryloxycarbonyl, 7–11C arylthiocarbonyl, and 7–11C aryloxythiocarbonyl radicals, $R^{46}$ is a hydrogen atom or one of the values for $R^{44}$ given above and $R^{47}$ is a hydrogen atom or one, two or three radicals selected from halogen atoms and 1–6C alkyl and 1–6C alkoxy radicals, or $R^2$ is a tetrazol-5-yl radical.

A particular value for $R^3$ is a hydrogen atom or a methoxy or methylthio radical.

A particular value for $X^1$ is a sulphur or oxygen atom, a CH$_2$ radical or a radical of the formula NR$^7$ in which R$^7$ is a hydrogen atom, a methyl, formyl or benzyl radical.

A particular value for $X^2$ is a nitrogen atom or a radical of the formula N⊕R$^8$.

Particular values for $R^4$ and $R^8$, which may be the same or different, are hydrogen atoms or methyl, acetyl, hydroxy, methoxy, amino, acetylamino, methylamino, 2-aminoethyl, 2-hydroxyethyl, carboxymethyl, 2-carboxyethyl, 3-carboxypropyl, allyl, methoxymethyl, methoxycarbonylmethyl, t-butoxycarbonylmethyl, 3-(ethoxycarbonyl)propyl, 3-(t-butoxycarbonyl)propyl, furylmethyl, phenyl, benzyl, in the latter two of which the phenyl ring is optionally substituted by a fluorine, chlorine or bromine atom or by a methyl, methoxy, nitro, hydroxy, amino, carboxy or methoxycarbonyl radical, propargyl, allenyl or 3-phenylallyl radicals.

Particular values for $R^5$ and $R^6$, which may be the same or different, are fluoromethyl, chloromethyl, bromomethyl, difluoromethyl, trifluoromethyl, azidomethyl, 3-azidopropyl, cyanomethyl, 2-cyanoethyl, carboxymethyl, 2-carboxyethyl, methoxycarbonylmethyl, carbamoylmethyl, 2-carbamoylethyl, methylcarbamoylmethyl, dimethylcarbamoylmethyl, 2-amino-2-carboxyethyl, vinyl, allyl, 2-nitrovinyl, 2-phenylvinyl, 1-phenylvinyl, 2-phenylallyl, 3-phenylallyl, 1,2-diphenylvinyl, 2,2-diphenylvinyl, 2,3-diphenylallyl, 3,3-diphenylallyl, 1,2,2-triphenylvinyl, 2,3,3-triphenylallyl, methylthio, 2-aminoethylthio, 2-methylaminoethylthio, 2-dimethylaminoethylthio, 2-aminoethoxy, 2-methylaminoethoxy, 2-dimethylaminoethoxy, phenylthio, phenoxy, benzyl, amino, methylamino, dimethylamino, phenylamino, benzylamino, diphenylamino, formyl, acetyl, benzoyl, methoxycarbonylamino, phenoxycarbonylamino, methoxythiocarbonylamino, phenoxythiocarbonylamino, acetylamino, propionylamino, benzoylamino, 3-methylureido, 3-phenylureido, 3-hydroxyprop-1-enyl, carbamoyl, methylcarbamoyl, dimethylcarbamoyl, 2-dimethylaminoethylcarbamoyl, 3-dimethylaminopropylcarbamoyl, phenylcarbamoyl, thiocarbamoyl, (methyl)thiocarbamoyl, (dimethyl)thiocarbamoyl, (phenyl)thiocarbamoyl, (2-dimethylaminoethyl)thiocarbamoyl, methoxymethyl, 3-methoxypropyl, acetoxymethyl, 3-acetoxypropyl, carbamoyloxymethyl, methylcarbamoyloxymethyl, 3-(methylcarbamoyloxy)propyl, dimethylcarbamoyloxymethyl, (phenyl)(hydroxy)methyl, (phenyl)(amino)methyl, acetylaminomethyl, 2-acetylaminoethyl, 3-acetylaminopropyl, 2-trifluoroacetylaminoethyl, 3-trifluoroacetylaminopropyl, benzoylaminomethyl, ureidomethyl, 3-ureidopropyl, (3-methylureido)methyl, 2-(3-methylureido)ethyl, (3,3-dimethylureido)methyl (3-phenylureido)methyl, guanidinomethyl, formimidoylaminomethyl, methylimidoylaminomethyl, methoxy, formylmethyl, methanesulphonylaminomethyl, 2-(methanesulphonylamino)ethyl, 3-(methanesulphonylamino)propyl or benzenesulphonylaminomethyl radicals or $R^5$ and $R^6$ are ethyl or propyl radicals which are substituted on different carbon atoms by two radicals selected from hydroxy, nitro, amino, methylamino, dimethylamino, phenylamino, benzylamino, (phenyl)(methyl)amino, (benzyl)(methyl)amino, pyrrolidino, piperidino, piperazino, N-methylpiperazino, morpholino, methoxy, methylthio, phenoxy, phenylthio, benzyloxy and benzylthio radicals, or $R^5$ and $R^6$ are ethyl or propyl radicals which are substituted on one carbon atom by a nitro, amino, methylamino, dimethylamino or acetylamino radical and on a different carbon atom by a methyl radical which is itself substituted by two radicals selected from cyano, methoxycarbonyl and acetyl radicals, or $R^5$ and $R^6$ are radicals of the formulae II, III, IV, V, VI, VII or VIII given in claim 1 in which Y is an oxygen or sulphur atom or a CH$_2$ radical, m is 1, 2 or 3, q is 0, 1 or 2, n is 0, 1 or 2, p is 1 to 4, $R^9$ is a methyl, ethyl, phenyl or benzyl radical, $R^{10}$ is a hydrogen atom or a methyl or phenyl radical, $R^{11}$ is a hydrogen atom or a methyl, phenyl, benzyl or heterocyclyl radical, $R^{12}$ is a hydrogen atom or a methyl or n-propyl radical optionally substituted by a carboxy, methoxycarbonyl, carbamoyl or cyano, radical, $R^{13}$ is a heterocyclyl radical, $R^{14}$ is a hydroxy or amino radical, $R^{15}$ is a pyridyl radical, $R^{16}$, $R^{17}$ and $R^{18}$, which may be the same or different, are hydrogen atoms or methyl or phenyl radicals, and $R^{19}$ and $R^{20}$, which may be the same or different, are cyano, nitro, methoxycarbonyl, phenoxycarbonyl, acetyl or benzoyl radicals, or $R^5$ and $R^6$ are heterocyclic radicals which are linked (to the imidazole ring) by a direct bond or by a methylene or thiomethylene (SCH$_2$) bridge, or $R^5$ and $R^6$ are hydrogen, fluorine, chlorine or bromine atoms or methyl, cyano, hydroxy, carboxy, methoxycarbonyl, aminomethyl, 2-aminoethyl, methylaminomethyl, dimethylaminomethyl, hydroxymethyl, 2-hydroxyethyl or pyridyl radicals or phenyl radicals optionally substituted by 1 or 2 radicals selected from fluorine, chlorine and bromine atoms and nitro, amino, hydroxy, carboxy, cyano, methyl and methoxycarbonyl radicals, or $R^5$ and $R^6$ are 2-nitroethyl, buta-1,4-dienyl, buta-1-en-4-ynyl, 2-ethoxycarbonylaminoethyl, 3-isobutoxycarbonylaminopropyl, 2-methylcarbamoylethyl, 2-dimethylcarbamoylethyl, 2-phenylcarbamoylethyl, 2-heterocyclylcarbonylaminoethyl, 3-heterocyclylcarbonylaminopropyl, 3-acetylcarbamoyloxypropyl, 3-benzoylcarbamoyloxypropyl, 3-heterocyclylcarbonylcarbamoyloxypropyl, 3-phenylcarbamoyloxypropyl, 3-heterocyclylcarbamoyloxypropyl, 3-[3-(2,2,2-trifluoroethyl)ureido]propyl, 3-(3-phenylureido)propyl, 2-(3-heterocyclylureido)ethyl, 2-[3-(methyl)thioureido]ethyl, 3-[3-(2,2,2-trifluoroethyl)thioureido)propyl, 2-[3-(phenyl)thioureido]ethyl, 2-[3-(heterocyclyl)thioureido]ethyl, 1-aminocyanomethyl, 1-dimethylaminocyanomethyl or N-trifluoroacetyl-N-benzylaminomethyl radicals or radicals of the formula IX, X and XI given in claim 1 in which $R^{11}$ and $R^{12}$ have the meanings given above, B is a vinylene radical, $R^{21}$ is a hydrogen atom or a methyl, phenyl or cyclohexyl radical, and $R^{22}$ is a carboxy, carbamoyl, methoxycarbonyl or toluene-p-sulphonyl radical, wherein when $R^5$ or $R^6$ contains a phenyl radical, that phenyl radical may optionally be substituted by 1 or 2 substituents selected from fluorine, chlorine and bromine atoms and nitro, amino, hydroxy, carboxy, cyano, methyl, methoxycarbonyl, sulpho, methoxy, trifluoromethyl, methylsulphamoyl, dimethylsulphamoyl and dimethylamino radicals, and wherein, when $R^5$ or $R^6$ contains a heterocyclic radical, that radical is a furan, thiophene, pyrrole, oxazole, thiazole, imidazole, isoxazole, isothiazole, thiadiazole, oxadiazole, triazole, tetrazole, pyridine, pyrimidine, pyrazine, pyridazine or piperazine ring, such ring, were possible, optionally being in the form of the N-oxide, such ring being optionally fused with a benzene ring and such fused benzene ring and/or (where possible) heterocyclic ring being optionally substituted by one or two substituents selected from fluorine, chlorine and bromine atoms and methyl, ethyl, hydroxy, methoxy, phenoxy, mercapto, methylthio, phenylthio, carboxy, methoxycarbonyl, phenoxycarbonyl, carbamoyl, methylcarbamoyl, dimethylcarbamoyl, phenylcarbamoyl, diphenylcarbamoyl, nitro, amino, methylamino, dimethylamino, phenylamino, (phenyl)(methyl)amino, diphenylamino, carboxyamino, (carboxy)(methyl)amino, (carboxy)(phenyl)amino, acetylamino, (acetyl)(methyl)amino, benzoylamino, (benzoyl)(methyl)amino, cyano, phenyl, sulphamoyl, methylsulphamoyl, dimethylsulphamoyl, phenylsulphamoyl, trifluoromethyl, 2,2,2-trifluoroethyl, 2-aminoethyl, 2-methylaminoethyl, 2-dimethylaminoethyl, 2-carboxyethyl, 2-sulphoethyl and oxo radicals, provided that when $X^1$ is a sulphur atom, $X^2$ is a nitrogen atom or $N \oplus R^8$ in which $R^8$ is a hydrogen atom, $R^3$ is a hydrogen atom and $R^4$ is a hydrogen atom or a methyl, acetyl, hydroxy, methoxy, amino, acetylamino, methylamino, phenyl or benzyl radical, the latter two being optionally substituted on the benzene ring by a methoxy radical, then $R^5$ and $R^6$ cannot both be selected from the group consisting of hydrogen, fluorine, chlorine and bromine atoms, and methyl, cyano, hydroxy, carboxy, methoxycarbonyl, aminomethyl, 2-aminoethyl, methylaminomethyl, dimethylaminomethyl, hydroxymethyl, 2-hydroxyethyl and pyridyl radicals and phenyl radicals optionally substituted by 1 or 2 radicals selected from fluorine, chlorine and bromine atoms and nitro, amino, hydroxy, carboxy, cyano, methyl and methoxycarbonyl radicals.

A particular value for $R^{41}$ is a hydrogen atom or a methyl radical.

A particular value for $R^{42}$ is a methyl, ethyl, n-propyl, i-propyl, n-butyl or t-butyl radical.

A particular value for $R^{43}$ is a hydrogen atom or a methyl, ethyl, n-propyl, i-propyl, i-butyl, s-butyl, benzyl or methoxycarbonyl radical.

A particular value for $R^{44}$ is a hydrogen atom or a methyl, ethyl, phenyl or benzyl radical.

A particular value for $R^{45}$ is a hydrogen atom or one, two or three substituents selected from chlorine and bromine atoms and nitro, cyano, methyl, methoxy, methylthio, methanesulphinyl, methanesulphonyl, methoxycarbonyl, methoxythiocarbonyl, acetylamino, phenyl, phenoxy, phenylthio, benzenesulphinyl, benzenesulphonyl, phenoxycarbonyl, phenylthiocarbonyl and phenoxythiocarbonyl radicals.

A particular value for $R^{46}$ is a hydrogen atom or one of the values for $R^{45}$ given immediately above.

A particular value for $R^{47}$ is a hydrogen atom or one, two or three radicals selected from chlorine and bromine atoms and methyl and methoxy radicals.

The following are 15 preferred features of the cephalosporin derivative of the formula I. When any one of these features is taken, either singly or in combination, with the other general features of the cephalosporin derivative of the formula I listed above, there are obtained preferred sub-groups of compounds within the above general definition.

1. $X^1$ is a sulphur atom.
2. $X^2$ is a nitrogen atom.
3. $R^2$ is a carboxy radical or an acetoxymethyl, pivaloyloxymethyl, acetylmethyl, ethoxycarbonyloxymethyl or phthalidyl ester thereof.
4. $R^3$ is a hydrogen atom.
5. $R^4$ is a hydrogen atom.
6. $R^6$ is a hydrogen atom.
7. $R^2$ is a carboxy radical.
8. $R^1$ is a radical of the formula $CH_2Y$ in which Y is derived from an oxygen nucleophile.
9. $R^1$ is a radical of the formula $CH_2Y$ in which Y is derived from a sulphur nucleophile.
10. $R^5$ and $R^6$ are hydrogen atoms.
11. $R^6$ is a hydrogen atom and $R^5$ is an alkenyl, alkanesulphonylaminoalkyl, cyanoalkyl, nitroalkyl, alkanesulphinyl, alkanesulphonyl, alkylcarbamoyloxyalkyl, alkanoylaminoalkyl, haloalkanoylaminoalkyl, heterocyclylcarbonylaminoalkyl, heterocyclylalkylcarbonylaminoalkyl or ureidoalkyl radical.
12. $R^6$ is a hydrogen atom and $R^5$ is an alkenyl radical (in which the double bond is other than at the 1-position), alkanesulphonylaminoalkyl, cyanoalkyl, nitroalkyl, alkanesulphinyl or alkanesulphonyl radical.
13. $R^6$ is a hydrogen atom and $R^5$ is an allyl, 2-methanesulphonylaminoethyl, 3-methanesulphonylaminopropyl, cyanomethyl, 2-cyanomethyl, 2-nitroethyl, 3-ethanesulphinylpropyl, 3-ethanesulphonylpropyl, 2-(2-aminothiazol-4-ylacetylamino)ethyl or 2-ethoxycarbonyl-2-formylaminoethyl radical.
14. $R^1$ is a hydrogen or chlorine atom or a methyl, hydroxymethyl, aminomethyl, azidomethyl, methoxymethyl, acetoxymethyl, benzoyloxymethyl, acetylaminomethyl, carbamoyloxymethyl, 1-methyl-1H-tetrazol-5-ylthiomethyl, 1-carboxymethyl-1H-tetrazol-5-ylthiomethyl, 1-(2-dimethylamino)ethyl-1H-tetrazol-5-ylthiomethyl, 1-sulphomethyl-1H-tetrazol-5-ylthiomethyl, 1-isopropyl-1H-tetrazol-5-ylthiomethyl, 1-(2,2,2-trifluoroethyl)-1H-tetrazol-5-ylthiomethyl, 1-phenyl-1H-tetrazol-5-ylthiomethyl, 1-(2-methylthioethyl)-1H-tetrazol-5-ylthiomethyl, 1,3,4-thiadiazol-2-ylthiomethyl, 5-methyl-1,3,4-thiadiazol-2-ylthiomethyl, 5-methylthio-1,3,4-thiadiazol-2-ylthiomethyl, 5-mercapto-1,3,4-thiadiazol-2-ylthiomethyl, 5-methyl-1,2,4-thiadiazol-3-ylthiomethyl, 5-acetamido-1,3,4-thiadiazol-2-ylthiomethyl, 1,2,3-thiadiazol-5-ylthiomethyl, 5-sulphomethyl-1,3,4-oxadiazol-2-ylthiomethyl, 1H-1,2,3-triazol-4-ylthiomethyl, 5-trifluoromethyl-1H-1,2,4-triazol-3-ylthiomethyl, 1H-1,2,4-triazol-3-ylthiomethyl, 2-methyl-2H-1,2,3-triazol-4-ylthiomethyl, 4-carboxymethyl-5-methylthiazol-2-ylthiomethyl, 4-(3-carboxypropyl)-5-methylthiazol-2-ylthiomethyl, 4,6-dimethylpyrimid-2-ylthiomethyl, 2-thiazolin-2-ylthiomethyl, benzoxazol-2-ylthiomethyl, benzthiazol-2-ylthiomethyl, 2-carboxyphenylthiomethyl, (6-carboxymethyl-7-hydroxypyrrolo[1,2-b]pyridazin-2-yl)thiomethyl, 4-methyl-6-hydroxy-5-oxodihydro-1,2,4-triazin-3-ylthiomethyl, 2-methyl-6-hydroxy-5-oxodihydro-1,2,4-triazin-3-ylthiomethyl, pyrid[2,3-c]imidazol-2-ylthiomethyl, pyrimid[4,5-c]imidazol-2-ylthiomethyl, 1-pyridiniomethyl, (1-oxido-2-pyridinio)thiomethyl, 4,4-dimethyl-1-piperaziniothiocarbonylthiomethyl, tetrazol[4,5-b]pyridazin-6-ylthiomethyl, 8-aminotetrazol[4,5-b]pyridazin-6-ylthiomethyl, 4-(2-sulphoethyl)-pyridiniomethyl or 6-hydroxypyridazin-3-ylthiomethyl radical.

15. $R^1$ is a hydrogen atom.

Particular compounds of the invention are described in the Examples. The following is a group of preferred compounds:

7-(4-allylimidazol-2-yl)amino-3-(1-methyl-1H-tetrazol-5-yl)thiomethylceph-3-em-4-carboxylic acid (Example 6.1);

7-(4-allylimidazol-2-yl)amino-3-(1H-1,2,3-triazol-4-yl)thiomethylceph-3-em-4-carboxylic acid (Example 6.2);

7-(4-allylimidazol-2-yl)amino-3-(1,3,4-thiadiazol-2-yl)thiomethylceph-3-em-4-carboxylic acid (Example 7);

7-(4-allylimidazol-2-yl)amino-3-chloroceph-3-em-4-carboxylic acid (Example 8.2);

7-(4-cyanomethylimidazol-2-yl)amino-3-(1-methyl-1H-tetrazol-5-yl)thiomethylceph-3-em-4-carboxylic acid (Example 44);

7-(4-cyanomethylimidazol-2-yl)amino-3-(1H-1,2,3-triazol-4-yl)thiomethylceph-3-em-4-carboxylic acid (Example 45);

7-[4-(2-cyanoethyl)imidazol-2-yl]amino-3-(1-methyl-1H-tetrazol-5-yl)thiomethylceph-3-em-4-carboxylic acid (Example 16);

7-[4-(2-methanesulphonylaminoethyl)imidazol-2-yl]amino-3-(1-methyl-1H-tetrazol-5-yl)thiomethylceph-3-em-4-carboxylic acid (Example 38);

7-[4-(3-methanesulphonylaminopropyl)imidazol-2-yl]amino-3-acetoxymethylceph-3-em-4-carboxylic acid (Example 23);

7-[4-(2-nitroethyl)imidazol-2-yl]amino-3-(1-methyl-1H-tetrazol-5-yl)thiomethylceph-3-em-4-carboxylic acid (Example 27);

7-[4-(3-ethanesulphinylpropyl)imidazol-2-yl]amino-3-(1-methyl-1H-tetrazol-5-yl)thiomethylceph-3-em-4-carboxylic acid (Example 50);

7-[4-(3-ethanesulphonylpropyl)imidazol-2-yl]amino-3-(1-methyl-1H-tetrazol-5-yl)thiomethylceph-3-em-4-carboxylic acid (Example 51);

7-[4-(3-acetylaminopropyl)imidazol-2-yl]amino-3-(1-methyl-1H-tetrazol-5-yl)thiomethylceph-3-em-4-carboxylic acid (Example 21);

3-acetoxymethyl-7-[4-(2-[2-aminothiazol-4-ylacetylamino]ethyl)imidazol-2-yl]aminoceph-3-em-4-carboxylic acid (Example 35);

7-[4-(2-amino-5-methylthiazol-4-ylmethyl)imidazol-2-yl]amino-3-(1-methyl-1H-tetrazol-5-yl)thiomethylceph-3-em-4-carboxylic acid (Example 47);

3-(1-methyl-1H-tetrazol-5-yl)thiomethyl-7-[4-(3-ureidopropyl)imidazol-2-yl]aminoceph-3-em-4-carboxylic acid (Example 81);

7-[4-(2-ethoxycarbonyl-2-formylaminoethyl)imidazol-2-yl]amino-3-(1-methyl-1H-tetrazol-5-yl)thiomethylceph-3-em-4-carboxylic acid (Example 85);

and the pharmaceutically-acceptable acid-addition salts and base-addition salts thereof.

A suitable acid-addition salt of the cephalosporin derivative of the invention is, for example, a salt formed with hydrochloric, hydrobromic, phosphoric, sulphuric, citric or maleic acid. A suitable base-addition salt of the cephalosporin derivative of the invention is, for example, an alkali metal salt (e.g. a sodium or potassium salt), an alkaline earth metal salt (e.g. a calcium or magnesium salt), or a salt with a primary, secondary or tertiary organic amine (e.g. triethylamine, procaine, dibenzylamine and N,N¹-dibenzyl ethylenediamine, and other amines which have been used to form salts with cephalosporins).

The cephalosporin derivative of the formula I may be manufactured by methods known in themselves for the manufacture of chemically analogous compounds. The following processes, $R^0$, $R^1$, $R^2$, $R^3$, $R^4$, $R^5$, $R^6$, $X^1$ and $X^2$ having the meanings stated above, unless indicated otherwise, are therefore provided as further features of the invention.

The process of the invention is characterised by:

(a) for those compounds in which $R^2$ is a carboxy radical or a heterocyclic radical carrying an acidic proton, and there is optionally a carboxy radical in another part of the molecule, deprotection of the corresponding compound which carries a protecting group, or groups, in place of the acidic hydrogen atom, or atoms. When $R^2$ is a carboxy radical a particularly useful protecting group is the diphenylmethyl or p-methoxybenzyl radical. Such a protecting group may be removed by treatment with a strong organic acid, for example trifluoroacetic acid. A further particularly useful protecting group is the t-butyl radical. This protecting group may be removed by treatment with a strong organic acid such as trifluoroacetic or formic acid. The process may be conducted in the presence of excess organic acid as diluent or solvent or in the presence of an additional diluent or solvent such as anisole or toluene. The process is preferably conducted at or below ambient temperature and preferably over a period of from 5 minutes to 5 hours. Other useful protecting groups are the trimethylsilyl radical (removed by water), the benzyl and substituted benzyl radicals, for example the p-nitrobenzyl or p-methoxybenzyl radical (removed by hydrogenolysis) and the 2,2,2-trichloroethyl radical (removed by zinc/acetic acid).

(b) reaction of a compound of the formula XXX:

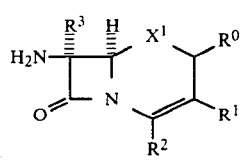

with a compound of the formula XXXI:

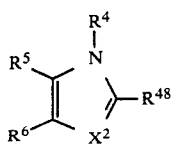

XXXI in which $R^{48}$ is a displaceable radical. $R^{48}$ is for example a halogen atom, preferably a fluorine or chlorine atom. The reaction is preferably conducted in the presence of at least one equivalent of an acid in order that the compound of the formula XXXI is in the protonated form. The reaction may be conducted in the presence of a diluent or solvent, for example acetonitrile, dimethylformamide or tetrahydrofuran or mixtures of these and it may be accelerated or completed by the application of heat, for example by heating to 85° or to the boiling point of the diluent or solvent. The compound of the formula XXXI may conveniently be prepared in situ by prior reaction of the corresponding N-triphenylmethyl derivative with toluene-p-sulphonic acid. The compound of the formula XXX is then added to the reaction mixture.

(c) for those compounds in which $R^1$ is a radical of the formula $CH_2Y$, reaction of a compound of the formula I in which $R^1$ is a radical of the formula $CH_2—R^{48}$ in which $R^{48}$ is a displaceable radical with a compound of the formula Y—H. $R^{48}$ is, for example, a halogen atom or an acetoxymethyl radical. The reaction may be conducted in a diluent or solvent such as acetonitrile, in the presence of boron trifluoride. The reaction may be accelerated or completed by the application of heat, for example by heating to 50°.

(d) for those compounds in which $X^2$ is a nitrogen atom, reaction of a compound of the formula XXXII:

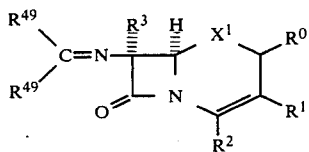

XXXII in which $R^{49}$ is a chlorine or bromine atom with a compound of the formula XXXIII:

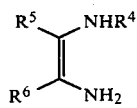

XXXIII or a formal tautomer thereof. $R^{49}$ is preferably a bromine atom. The reaction may be carried out in a diluent or solvent, a preferred solvent being tetrahydrofuran to which may, if necessary, be added a little methanol to achieve solution. It may be necessary to use an excess of the compound of the formula XXXIII in order to achieve optimal yields of the product. The reaction may be conducted over the temperature range −78° to ambient temperature depending on the nature of the starting materials, and indeed in some cases the reaction may be accelerated or completed by heating, for example by heating to 50° or to the boiling point of the diluent or solvent. The reaction is preferably conducted under an inert atmosphere, for example a nitrogen or argon atmosphere.

(e) for those compounds in which $R^4$ is other than a hydrogen atom, and $X^2$ is a nitrogen atom, reaction of a compound for the formula XXX with a compound of the formula XXXIV:

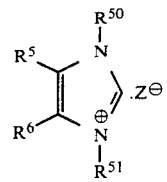

XXXIV in which $R^{50}$ has the value given above for $R^4$ other than a hydrogen atom, $R^{51}$ is a displaceable radical and $Z^\ominus$ is an anion. $R^{51}$ is, for example, a 1–6C alkoxy or 1–6C alkylthio radical, for example a methoxy or methylthio radical. $Z^\ominus$ is, for example, a halide anion, for example a chloride, bromide or iodide, or a methanesulphonate or toluene-p-sulphonate. The reaction may be conducted in a diluent or solvent such as methanol, water or an aqueous buffer. It is preferably conducted at ambient temperature.

(f) for those compounds in which $R^{52}$ is a hydrogen atom, replacement by hydrogen of the radical $R^1$ in a compound of the formula XXXV:

XXXV in which $R^{52}$ is a hydroxy, methoxy or methylthio radical. The process may be carried out using titanium trichloride or trimethyl phosphite. The reaction may be conducted in a diluent or solvent such as methanol, tetrahydrofuran or methylene chloride and may be accelerated or completed by the application of heat, for example by heating to 40°–50°.

or (g) for those compounds in which $R^4$ is an alkyl, alkanoyl, carboxyalkyl, alkenyl, alkoxyalkyl, alkoxycarbonylalkyl, furylmethyl, phenylalkyl, alkynyl, alkadienyl or aryalkenyl radical, alkylation or aceylation of the corresponding compound in which $R^4$ is a hydrogen atom.

When the process of the invention manufactures the compound of the formula I in the form of the free acid or free base, or the zwitterion, and a salt is required, the compound of the formula I in the free acid or zwitterionic form is reacted with a base which affords a pharmaceutically-acceptable cation, or the compound of the formula I in the free base or zwitterionic form is reacted with an acid which affords a pharmaceutically-acceptable anion. When the process of the invention manufactures the compound of the formula I in the form of an acid-addition salt and the zwitterionic form is required, the compound of the formula I in the form of the acid-addition salt is reacted with a low molecular weight epoxide such as epoxypropane.

The compound of the formula XXXII in which $X^1$ is an oxygen atom, a $CH_2$ radical or a radical of the formula $NR^7$ in which $R^7$ is a hydrogen atom, a 1–6C alkyl, formyl or benzyl radical, and when $R^3$ is an alkoxy or alkthio radical, $X^1$ is also a sulphur atom, and, when $R^2$ is a carboxy radical, the esters (for example the diphenylmethyl, t-butyl, trimethylsilyl, benzyl, substituted benzyl, and 2,2,2-trichloroethyl esters) thereof is a valuable intermediate for preparing many of the compounds of this invention. This compound is therefore provided as a further feature of the invention. It may be prepared by formylation of the compound of the formula XXX or an ester thereof, followed by reaction of the resulting formylamino compound with phosgene to give the corresponding isonitrile. This compound is then halogenated to give the compound of the formula XXXII. When $R^2$ is a carboxy radical additional protection and deprotection stages may be required.

The starting material for use in process (a) may be prepared using one of the processes (b) to (g) inclusive of the invention in which the acidic radical is in the protected form. Use of process (b) is illustrated in Examples 3, 4, 39, 40, 41, 42, 43, 78 and 83. Use of process (f) is illustrated in Examples 1 and 2.

Many of the starting materials of the formula XXX and XXXI for use in process (b) are described in European Patent Publication No. 31708. A large number of starting materials of the formula XXX are also known in the cephalosporin art. Other novel starting materials of the formula XXXI may be prepared from known compounds, by standard chemical reactions. Thus when $R^4$ is other than a hydrogen atom or a hydroxy or amino radical, the starting material of the formula XXXI may be prepared by direct replacement of the hydrogen atom, for example as described in Examples 72–78 and 83.

When $R^5$ or $R^6$ is other than hydrogen, many of the starting materials of the formula XXXI may be prepared from the anion of 2-fluoro-1-triphenylmethylimidazole (European Patent Publication No. 31708) by standard chemical reactions. Thus the compound of the formula XXXI in which $R^5$ or $R^6$ is a wide variety of radicals may be prepared by the methods set out in the Example listed in the following Table.

| $R^5$ or $R^6$ | Example No. |
| --- | --- |
| azidoalkyl | 41,48 |
| cyanoalkyl | 15,16,44,45 |
| carboxyalkyl | 17 |
| carbamoylalkyl | 39 |
| alkenyl | 52,73 |
| aryalkenyl | 6 |
| alkylthio | 6 |
| alkanoylamino | 66 |
| alkylcarbamoyl | 62 |
| (dialkylaminoalkyl)carbamoyl | 65 |
| arylcarbamoyl | 63,64 |
| alkoxyalkyl | 42,49 |
| alkanoyloxyalkyl | 9 |
| alkylcarbamoyloxyalkyl | 9 |
| alkanoylaminoalkyl | 20,21,29 |
| ureidoalkyl | 81 |
| alkylureidoalkyl | 36 |
| alkanesulphonylaminoalkyl | 23,38 |
| alkyl substituted on different carbon atoms by hydroxy radicals | 59 |
| radical formula II | 43,50,51 |
| radical formula IV | 8,19,57 |
| heterocycle linked via methylene | 47 |
| nitroalkyl | 26,27,28 |
| alkadienyl | 53 |
| alkenynyl | 54 |
| alkoxycarbonylaminoalkyl | 40 |
| arylcarbamoylalkyl | 18 |
| heterocycylcarbonylaminoalkyl | 25,30,31,32,33,34 |

| $R^5$ or $R^6$ | Example No. |
| --- | --- |
| heterocyclylalkylcarbonylaminoalkyl | 24,35 |
| alkanoylcarbamoyloxyalkyl | 12 |
| heterocyclylcarbonylcarbamoyloxyalkyl | 13 |
| arylcarbamoyloxyalkyl | 11 |
| heterocyclylcarbamoyloxyalkyl | 14 |
| (heterocyclylureido)alkyl | 37 |
| [haloalkyl(thioureido)]alkyl | 80 |
| 1-aminocyanomethyl | 60 |
| 1-dimethylaminocyanomethyl | 61 |
| N—trifluoroacetyl-N—benzyl-aminomethyl | 46 |
| radical formula IX | 55,56 |
| radical formula X | 58,67,68,69 |
| radical formula XI | 70,71,85 |

As noted above the cephalosporin derivatives of the invention have antibacterial properties. Thus they are useful antibacterial agents, many of then having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system.

The antibacterial properties of the compounds of the invention may also be demonstrated in conventional mouse protection tests.

Cephalosporin derivatives have generally been found to be relatively non-toxic to warm-blooded animals, and this generalisation holds true for the compounds of the present invention. A number of compounds were administered to mice at doses considerably in excess of those required to afford protection against bacterial infections. Thus the following compounds were administered subcutaneously to mice in two single doses over one day, each dose being at least five times the minimum effective dose which protected 50% of the mice against infection with Salmonella dublin (PD$_{50}$):

7-(4-benzylimidazol-2-yl)amino-3-acetoxymethylceph-3-em-4-carboxylic acid (Example 1);

7-[4-(2-trifluoroacetylaminoethyl)imidazol-2-yl]amino-3-(2-methyl-1,3,4-thiadiazol-5-yl)thiomethylceph-3-em-4-carboxylic acid (Example 4.2);

7-(4-allylimidazol-2-yl)amino-3-(1-methyl-1H-tetrazol-5-yl)thiomethylceph-3-em-4-carboxylic acid (Example 6.1);

7-[4-(3-methylcarbamoyloxypropyl)imidazol-2-yl]amino-3-acetoxymethylceph-3-em-4-carboxylic acid (Example 9.2);

7-[4-(2-trifluoroacetylaminoethyl)imidazol-2-yl]amino-3-(1H-1,2,3-triazol-4-yl)thiomethylceph-3-em-4-carboxylic acid (Example 10);

7-[4-(2-cyanomethyl)imidazol-2-yl]amino-3-(1-methyl-1H-tetrazol-5-yl)thiomethylceph-3-em-4-carboxylic acid (Example 16);

7-[4-(3-[3-(2,2,2-trifluoroethyl)thioureido]propyl)imidazol-2-yl]amino-3-(1H-1,2,3-triazol-4-yl)thiomethylceph-3-em-4-carboxylic acid (Example 80).

No overt toxic symptoms or side effects attributable to the administered compound were noted.

The results set out in the following Table are illustrative of the biological activity of the compounds of the present invention. The compounds whose activities are displayed in this Table are the same seven compounds whose testing in mice is described immediately above. The following results are those obtained on a standard in vitro test system using Jewell and Pearmain agar medium. The antibacterial activity is described in terms of the minimum inhibitory concentration (MIC) determined by agar-dilution technique with an inoculum size of $\sim 10^5$ CFU.

| Organism | Code No. | MIC µg/ml Example No. | | | | | | |
|---|---|---|---|---|---|---|---|---|
| | | 1 | 4.2 | 6.1 | 9.2 | 10 | 16 | 80 |
| Strep. pyogenes | A1 | — | 16 | 8 | 32 | 64 | 8 | 32 |
| Staph. aureus | A6 | 32 | 32 | 32 | 64 | 64 | 16 | 32 |
| E. coli | A8 | 0.25 | 0.12 | 0.016 | 0.03 | 0.03 | 0.016 | 1 |
| Salmonella dublin | A20 | 0.5 | 0.25 | 0.016 | 0.06 | 0.016 | 0.008 | 0.5 |
| K. aerogenes | A10 | 1 | 0.12 | 0.03 | 0.06 | 0.06 | 0.06 | 2 |
| Ent. cloacae | A13 | 128 | 16 | 16 | 64 | 16 | 4 | 4 |
| Serratia marescens | A16 | 64 | 4 | 0.25 | 8 | 16 | 2 | 64 |
| Proteus mirabilis | A18 | 32 | 16 | 2 | 8 | 2 | 1 | 4 |
| Ps. aeruginosa | A21 | >256 | >256 | >256 | >256 | >256 | >128 | >128 |

According to a further feature of the invention there is provided a pharmaceutical composition which comprises a cephalosporin derivative of the invention in association with a non-toxic pharmaceutically-acceptable diluent or carrier.

The pharmaceutical composition of the invention may, for example, be in a form suitable for oral, rectal or parenteral administration, for which purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the cephalosporin derivative of the formula I the pharmaceutical composition of the invention may also contain, or be co-administered with, one or more known drugs selected from other clinically useful antibacterial agents (for example other $\beta$-lactams or aminoglycosides), inhibitors of $\beta$-lactamase (for example clavulanic acid), renal tubular blocking agents (e.g. probenicid) and inhibitors of metabolising enzymes (for example inhibitors of peptidases, for example Z-2-acylamino-3-substituted propenoates).

A preferred pharmaceutical composition of the invention is one suitable for intravenous, subcutaneous or intramuscular injection, for example a sterile injectable containing between 1 and 10% w/w of the cephalosporin derivative, or one suitable for oral administration in unit dosage form, for example a tablet or capsule which contains between 100 mg. and 1 g. of the cephalosporin derivative.

The pharmaceutical composition of the invention will normally be administered to man in order to combat infections caused by bacteria, in the same general manner as that employed for cephalothin, cefoxitin, cephradine and other known clinically used cephalosporin derivatives, due allowance being made in terms of dose levels for the potency of the cephalosporin derivative of the present invention relative to the known clinically used cephalosporins. Thus each patient will receive a daily intravenous, subcutaneous or intramuscular dose of 0.5 to 50 g., and preferably 0.5 to 10 g., of the cephalosporin derivative, the composition being administered 1 to 4 times per day. The intravenous, subcutaneous and intramuscular dose will be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the cephalosporin derivative, the composition being administered 1 to 4 times per day.

The invention is illustrated, but not limited, by the following Examples. The n.m.r. spectra are quoted in $\delta$ relative to tetramethylsilane ($\delta$=0) as internal standard, (s=singlet, d=doublet, t=triplet, m=multiplet, br=broad). The temperatures are in degrees Centigrade. The following contractions are used:
TFA=trifluoroacetic acid
THF=tetrahydrofuran
HOAC=acetic acid
EtOAc=ethyl acetate
MeOH=methanol
DMF=dimethylformamide
DMSO=dimethylsulphoxide
ether=diethyl ether
HPLC=high pressure liquid chromatography In the examples the cephalosporin derivative of the invention is isolated in the form of a salt, either an internal salt (a zwitterion) or a salt with an acid such as HBr or $CF_3COOH$. The actual salt which is isolated is dependent on a number of factors including the basicity of the product, the reaction work-up and purification conditions used and the nature of the starting material (salt or free base).

EXAMPLE 1

A solution of diphenylmethyl 3-acetoxymethyl-7-(4-benzylimidazol-2-yl)aminoceph-3-em-4-carboxylate (106 mg.) in a mixture of anisole (0.7 ml.) and TFA (0.4 ml.) was stirred at ambient temperature for 30 minutes and then evaporated to dryness at 25°. The residue was dissolved in the minimum amount of methylene chloride and precipitated with hexane to give 7-(4-benzylimidazol-2-yl)aminoceph-3-em-4-carboxylic acid trifluoroacetate (61 mg.), m.p. 200°–220°, having the following n.m.r. spectrum in $d_6DMSO$: 2.0 (s, 3H); 3.6 (s, 2H); 3.9 (s, 2H); 4.7 (d, 1H); 5.0 (d, 1H); 5.2 (d, 1H); 5.6 (dd, 1H); 6.8 (s, 1H); 7.3 (s, 5H); 9.3 (d, 1H).

The diphenylmethyl 3-acetoxymethyl-7-(4-benzylimidazol-2-yl)aminoceph-3-em-4-carboxylate used as starting material may be prepared as follows:

A mixture of 1-bromo-3-phenylacetone (25.95 g.), distilled toluene (50 ml.) and potassium phthalimide (22.5 g.) was heated under reflux with stirring for 5

21 hours, and then stirred at ambient temperature overnight. The mixture was filtered, the filtrate concentrated and the residue taken up in DMF and the solution shaken with a liter of water. The resulting precipitate was collected and dried. Further material was obtained on extraction of the filtrate, giving a total of 23.4 g. of 1-phenyl-3-phthalimidoacetone.

A mixture of hydroxylamine hydrochloride (9 g.) and a solution of 1-phenyl-3-phthalimidoacetone (23.4 g.) in pyridine/ethanol (80 ml.-80 ml.) was stirred at ambient temperature for 3 days. The resulting solution was concentrated, the residue washed twice with a mixture of toluene and methylene chloride and dried. The residue was purified by column chromatography on activated silica gel using cyclohexane/EtOAc 7:3 v/v as eluant to give 2-oximino-1-phenyl-3-phthalimidopropane (7.35 g.) as a mixture of syn and anti isomers.

Hydrazine hydrate (1.21 ml.) was added to a stirred suspension of 2-oximino-1-phenyl-3-phthalimidopropane (7.35 g.) in ethanol (140 ml.) immersed in a bath at 45°. Solution was rapidly attained and after 2 hours a solid precipitated. After 24 hours the mixture was allowed to come to ambient temperature and 1N HCl (25 ml.) was added with stirring. After 1 hour the suspension was evaporated to dryness, the residue taken up in water, filtered and the filtrate evaporated to dryness to give 2-oximino-3-phenylpropylamine hydrochloride (4.3 g.).

To a solution of 2-oximino-3-phenylpropylamine hydrochloride (3.88 g.) in methanol (35 ml.) was added with stirring a solution of one equivalent of potassium methoxide. The precipitated potassium chloride was filtered off and the filtrate evaporated to dryness at ambient temperature. To a suspension of the residual free base (3.16 g.) in anhydrous THF (150 ml.) was added trimethylchlorosilane (4.9 ml.) and triethylamine (5.4 ml.) with stirring under argon. Stirring was continued for 24 hours, and the mixture filtered under a current of nitrogen. This solution was added with stirring to a solution of diphenylmethyl 3-acetoxymethyl-7-dibromomethyleneaminoceph-3-em-4-carboxylate (3.9 g.) in anhydrous THF (20 ml.) cooled in a solid CO$_2$/acetone bath at −30°. After 1.5 hours TFA (1.6 ml.) was added, the solution was evaporated to dryness and the residue taken up in CH$_2$Cl$_2$. The mixture was filtered and the filtrate evaporated and the residue dried. It was purified by low temperature column chromatography on activated silica gel using CH$_2$Cl$_2$/MeOH 100:0 to 98.5:1.5 v/v as eluant, to give diphenylmethyl 3-acetoxymethyl-7-(4-benzyl-3-hydroxyimidazol-2-yl)aminoceph-3-em-4-carboxylate (1.85 g.).

To a solution of the above hydroxyimidazole (1.57 g.) in MeOH (25 ml.) was added titanium trichloride (5.14 ml.). The mixture was heated to 40°-45° for 10 minutes and then the pH adjusted to 7 with 10% w/v aqueous sodium bicarbonate. The orange precipitate was filtered, washed with water and dried. The solid was extracted with CH$_2$Cl$_2$ and with methanol, and the combined extracts evaporated to dryness. The residue was purified by pressure chromatography (1 bar) at low temperature on finely divided silica gel using CH$_2$Cl$_2$/MeOH/HOAc 100:0:0 to 98:1:1 v/v/v as eluant to give diphenylmethyl 3-acetoxymethyl-7-(4-benzylimidazol-2-yl)aminoceph-3-em-4-carboxylate (0.588 g.) which was used without further purification.

22

EXAMPLE 2

The process described in Example 1 was repeated using the appropriate starting materials and the following compounds were thus obtained:

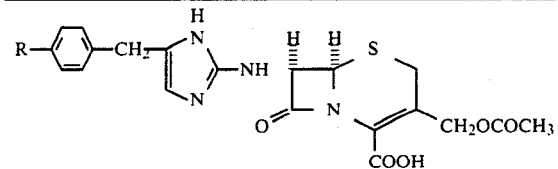

| —R | Footnotes |
|---|---|
| —NH$_2$ | 1 |
| —NO$_2$ | 2, 3 |

Footnotes
1. Product, the ditrifluoroacetate salt, had the following n.m.r. spectrum in d$_6$DMSO + CD$_3$CO$_2$D: - 2.0 (s, 3H); 3.5–3.8 (m, 4H); 4.7 (d, 1H); 5.0 (d, 1H); 5.2 (d, 1H); 5.7 (d, 1H); 6.5 (s, 1H); 6.6 (d, 2H); 6.9 (d, 2H).
2. Reaction carried out for 5 minutes.
3. Product, the trifluoroacetate salt, had the following n.m.r. in d$_6$DMSO + CD$_3$COOD: - 2.0 (s, 3H); 3.5–3.7 (m, 2H); 4.0 (s, 2H); 4.7 (d, 1H); 5.0 (d, 1H); 5.2 (d, 1H); 5.6 (d, 1H); 6.8 (s, 1H); 7.5 (d, 2H); 8.2 (d, 2H).

The starting materials used in the above process may be obtained as follows:

A mixture of 1-bromo-3-(4-nitrophenyl)acetone and potassium phthalimide (7.2 g.) in toluene (100 ml.) was heated under reflux with stirring for 4 hours. The mixture was filtered, the filtrate evaporated. The residue was purified by chromatography on silica gel using CH$_2$Cl$_2$ as eluant to give 1-phthalimido-3-(4-nitrophenyl)acetone, m.p. 184°.

A mixture of hydroxylamine hydrochloride (1.92 g.) and a solution of the above ketone (6 g.) in pyridine/ethanol (1:1 v/v, 70 ml.) was stirred at ambient temperature for 20 hours. The solvent was evaporated, the residue was washed with toluene/CH$_2$Cl$_2$ to remove residual pyridine and the resulting solid washed with water (x 2) then a small amount of CH$_2$Cl$_2$ to give 2-oximino-1-phthalimido-3-(4-nitrophenyl)propane, m.p. 181°-183°.

To a stirred suspension of the above oxime (3.78 g.) in ethanol (80 ml.) in a bath at 45° was added hydrazine hydrate (0.54 ml.). The stirred mixture was allowed to cool to ambient temperature over 24 hours. 1N HCl (11.1 ml.) was added with stirring and after 2 hours the mixture was evaporated to dryness, the residue taken up in water, filtered and the filtrate evaporated to dryness to give 2-oximino-3-(4-nitrophenyl)propylamine hydrochloride.

To a stirred solution of diphenylmethyl 3-acetoxymethyl-7-dibromomethyleneaminoceph-3-em-4-carboxylate (1.21 g.) in THF (10 ml.) at −35° was added 2-oximino-3-(4-nitrophenyl)propylamine (1.23 g., obtained from the HCl salt with aqueous 2N NH$_4$OH) in THF (20 ml.). After 15 minutes TFA (0.45 ml.) was added. The mixture was evaporated to dryness and the residue taken up in CH$_2$Cl$_2$, the mixture filtered and the filtrate evaporated to dryness. The residue was purified by chromatography on silica gel at low temperature using CH$_2$Cl$_2$/MeOH 100:0 to 97.5:2.5 v/v as eluant to give diphenylmethyl 3-acetoxymethyl-7-[4-(4-nitrobenzyl)-3-hydroxyimidazol-2-yl]aminoceph-3-em-4-carboxylate.

To a solution of the above imidazole derivative (0.685 g.) in MeOH (30 ml.) at 25° was dropwise added titanium trichloride (9.15 ml.). After 15 minutes a 10% w/v aqueous sodium bicarbonate solution was added to raise the pH to 7. The resulting precipitate was filtered and washed with methanol and the combined filtrates were evaporated. The residue was taken up in CH₂Cl₂, filtered and the filtrate evaporated. The residue was purified by low temperature chromatography on silica gel using CH₂Cl₂/MeOH/AcOH 100:0:0 to 90:5:5 v/v/v as eluant to give diphenylmethyl 3-acetoxymethyl-7-[4-(4-aminobenzyl)imidazol-2-yl]aminoceph-3-em-4-carboxylate ditrifluoroacetate, m.p. 140° (decomp.), which was used without further purification.

A suspension of diphenylmethyl 3-acetoxymethyl-7-[4-(4-nitrobenzyl)-3-hydroxyimidazol-2-yl]aminoceph-3-em-4-carboxylate (0.45 g.) and trimethylphosphite (0.8 ml.) in CH₂Cl₂ (1.0 ml.) at 45° with stirred for 2 hours. The solvent was evaporated and the residue purified by low temperature chromatography on silica gel using CH₂Cl₂/MeOH/AcOH 100:0:0 to 98:1:1 v/v/v as eluant to give diphenylmethyl 3-acetoxymethyl-7-[4-(4-nitrobenzyl)imidazol-2-yl]aminoceph-3-em-4-carboxylate trifluoroacetate which was used without further purification.

EXAMPLE 3

A suspension of t-butyl 3-methyl-7-[4-(2-trifluoroacetylaminoethyl)imidazol-2-yl]aminoceph-3-em-4-carboxylate (0.34 g.) in TFA (5 ml.) was stirred for 2 hours at ambient temperature and then evaporated to dryness. The residue was purified by precipitation from a THF solution with ether to give 3-methyl-7-[4-(2-trifluoroacetylaminoethyl)imidazol-2-yl]aminoceph-3-em-4-carboxylic acid trifluoroacetate as a cream solid (0.2 g.), m.p. 165° (decomp.), having the following n.m.r. spectrum in CH₃OD: 2.14 (s, 3H); 2.82 (t, 2H); 3.5 (m, 4H); 5.14 (d, 1H); 5.38 (d, 1H); 6.7 (s, 1H).

The t-butyl 3-methyl-7-[4-(2-trifluoroacetylaminoethyl)imidazol-2-yl]aminoceph-3-em-4-carboxylate used as starting material may be obtained as follows:

A mixture of t-butyl 3-methyl-7-aminoceph-3-em-4-carboxylate toluene-p-sulphonate (0.442 g.) and 2-fluoro-4-(2-trifluoroacetylaminoethyl)imidazole (0.45 g.) was stirred in acetonitrile (dried over molecular sieve, 10 ml.) at 70°–75° for 1.5 hours. The mixture was filtered and the filtrate purified on silica gel (500 g.) eluted with methylene chloride containing 1%, 2%, 3%, 4% and finally 5% v/v methanol. The relevant fractions were combined to give t-butyl 3-methyl-7-[4-(2-trifluoroacetylaminoethyl)imidazol-2-yl]aminoceph-3-em-4-carboxylate (0.34 g.) which was used without further purification.

EXAMPLE 4

The process described in Example 3 was repeated using the appropriate starting materials and the following compounds were thus obtained:

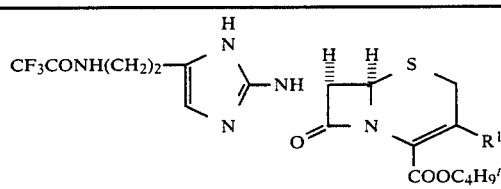

| R¹— | Footnotes |
|---|---|
| CH₃COOCH₂— | 1 |

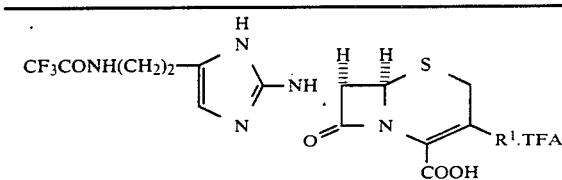

| R¹— | Footnotes |
|---|---|
| 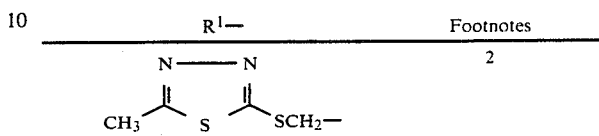 | 2 |

Footnotes
1. The product, 12% yield, had the following n.m.r. spectrum in CD₃OD: - 2.04 (s, 3H); 3.74 (t, 2H); 3.6 (m, 3H); 4.9 (M, 2H); 5.20 (d, 1H); 5.50 (d, 1H); 6.73 (s, 1H).
2. The product, 7% yield, had the following n.m.r. spectrum in d₆DMSO/CD₃CO₂H: - 2.70 (s, 3H); 3.45 (m, 4H); 3.72 (t, 2H); 4.42 (q, 2H); 5.19 (d, 1H); 5.58 (d, 1H); 6.78 (s, 1H).

The starting materials used in the above process may be obtained by repeating the process described in the second part of Example 3 using the appropriate starting materials. The following compounds were thus obtained:

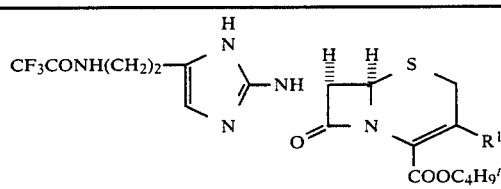

| R¹— | Footnotes |
|---|---|
| CH₃COOCH₂— | 1 |

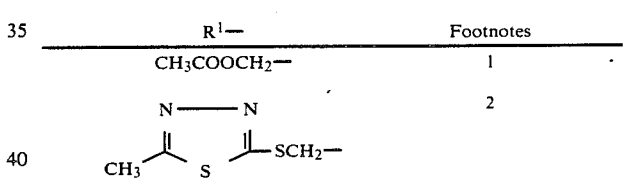

| R¹— | Footnotes |
|---|---|
| 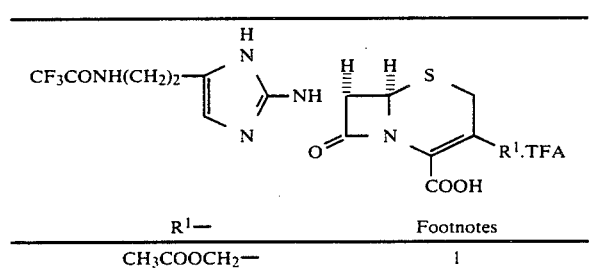 | 2 |

Footnotes
1. Reaction conducted at 90–95° under argon.
2. Reaction conducted at 85° for 1 hour under argon.

EXAMPLE 5

A mixture of 4-allyl-2-fluoro-1-triphenylmethyl imidazole (1.21 g.) and toluene-p-sulphonic acid monohydrate (0.635 g.) in DMF (8.5 ml.) was stirred at ambient temperature for 1 minute then at 80°. 3-Acetoxymethyl-7-aminoceph-3-em-4-carboxylic acid (0.904 g.) was added and the mixture was heated at 80° for 2.5 hours. The solution was evaporated to dryness in vacuo and water and EtOAc added to the residue. The aqueous layer was separated, evaporated to dryness, the residue redissolved in water and purified by preparative HPLC on Whatman "Partisil 10" using water/MeOH/HOAc 70:30:1 v/v/v as eluant to give 3-acetoxymethyl-7-(3-allylimidazol-2-yl)aminoceph-3-em-4-carboxylic acid (0.142 g.) having the following n.m.r. in d₆DMSO+CD₃COOD: 2.0 (s, 3H); 3.15 (d, 2H); 3.23 (d, 1H); 3.54 (d, 1H); 4.7 (d, 1H); 4.97 (d, 1H); 4.9–5.2 (m, 3H); 5.48 (d, 1H); 5.8 (m, 1H); 6.3 (s, 1H).

EXAMPLE 6

The process described in Example 5 was repeated using the appropriate starting materials and the following compounds were thus obtained:

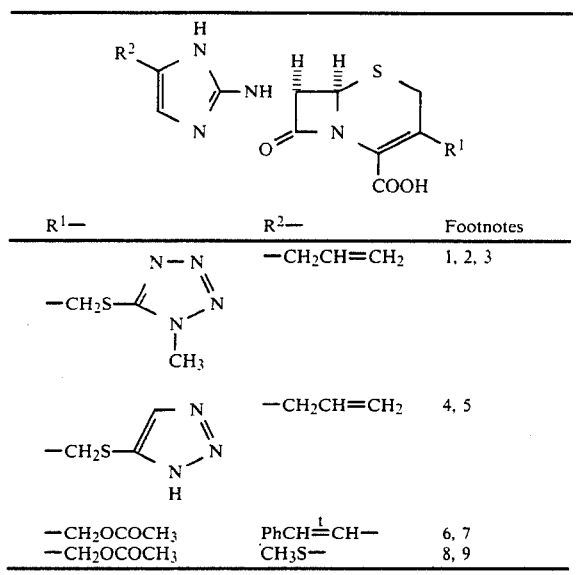

| $R^1-$ | $R^2-$ | Footnotes |
|---|---|---|
| $-CH_2S-\overset{N-N}{\underset{\underset{CH_3}{N}}{\diagdown\!\!\diagup}}N$ | $-CH_2CH=CH_2$ | 1, 2, 3 |
| $-CH_2S-\overset{N}{\underset{\underset{H}{N}}{\diagdown\!\!\diagup}}N$ | $-CH_2CH=CH_2$ | 4, 5 |
| $-CH_2OCOCH_3$ | $PhCH=CH-$ | 6, 7 |
| $-CH_2OCOCH_3$ | $CH_3S-$ | 8, 9 |

Footnotes
1. Reaction carried out at 40° for 3 days.
2. HPLC eluant: - water/MeOH/HOAc 65:35:1 v/v/v .
3. Product had the following n.m.r. in d$_6$DMSO + CD$_3$CO$_2$D: - 3.22 (d, 2H); 3.51 (d, 1H); 3.77 (d, 1H); 3.93 (s, 3H); 4.33 (s, 2H); 5.0–5.33 (m, 3H); 5.60 (d, 1H); 5.62–6.10 (m, 1H); 6.54 (s, 1H).
4. HPLC eluant: - water/MeOH/HOAc 60:40:1 v/v/v.
5. Product had the following n.m.r. in d$_6$DMSO: - 3.20 (d, 2H); 3.48 (d, 1H); 3.72 (d, 1H); 4.0 (s, 2H); 4.9–5.2 (m, 3H); 5.48 (d, 1H); 5.83 (m, 1H); 6.50 (s, 1H); 7.84 (s, 1H).
6. Product purified by evaporation of the reaction mixture, trituration of the residue with water/EtOAc, solution of undissolved material in the minimum DMF and precipitation with water.
7. Product had the following n.m.r. in d$_6$DMSO + CD$_3$COOD: - 2.0 (s, 3H); 3.4 (d, 1H); 3.7 (d, 1H); 4.7 (d, 1H); 5.02 (d, 1H); 5.17 (d, 1H); 5.76 (d, 1H); 6.8–7.5 (m, 8H).
8. HPLC eluant: - water/MeOH/HOAc 75:25:1.
9. Product had the following n.m.r. in d$_6$DMSO: - 2.08 (s, 3H); 2.28 (s, 3H); 3.4 (d, 1H); 3.64 (d, 1H); 4.7 (d, 1H); 5.05 (d, 1H); 5.15 (d, 1H); 5.62 (q, 1H); 6.60 (s, 1H); 6.95 (d, 1H).

The 2-fluoro-1-triphenylmethyl-4-(2-phenyl-trans-vinyl)imidazole used as starting material may be prepared as follows:

To a stirred mixture of 2-fluoro-4-formyl-1-triphenyl-methylimidazole (0.356 g.) and diethyl benzylphosphonate (0.228 g.) in 1,2-dimethoxyethane under an argon atmosphere at room temperature was added sodium hydride (0,048 g.). Stirring was continued for 18 hours and then water (15 ml.) was added. The precipitate was filtered and dried to give 2-fluoro-1-triphenyl-methyl-4-(2-phenyl-trans-vinyl)imidazole (0.415 g.), m.p. 167°–170°.

The 2-fluoro-4-methylthio-1-triphenylmethylimidazole used as starting material may be obtained as follows:

A mixture of 2-fluoro-1-triphenylmethylimidazole (0.328 g.) and t-butyl lithium (1.0 ml. of a 2M solution in pentane) in THF (3 ml.) was stirred at −78° for 2 hours. Dimethyl disulphide (0.18 ml.) was added and the mixture was stirred for 0.5 hours at −78° then at −15° for 1 hour. Ether was added and the organic layer washed to neutrality with water and finally with brine. The solution was dried and the solvent evaporated to give 2-fluoro-4-methylthio-1-triphenylmethylimidazole (0.368 g.), m.p. 142°–143°.

EXAMPLE 7

To a suspension of 3-acetoxymethyl-7-(3-allylimidazol-2-yl)aminoceph-3-em-4-carboxylic acid (0.038 g.) and 2-mercapto-1,3,4-thiadiazole (0.012 g.) in acetonitrile (0.2 ml.) was added boron trifluoride etherate (48% w/w, 32 µl) and the mixture heated at 60° for 2.5 hours. The solvent was evaporated and the residue dissolved in water/MeOH/HOAc 70:30:1 v/v/v (2 ml.). The solution was decanted from the residual tar and then purified by HPLC using water/MeOH/HOAc 70:30:1 then 60:40:1 v/v/v as eluants to give 7-(3-allylimidazol-2-yl)amino-3-(1,3,4-thiadiazol-2-yl)thiomethylceph-3-em-4-carboxylic acid (5 mg.) having the following n.m.r. in d$_6$DMSO+CD$_3$CO$_2$D: 3.20 (d, 2H); 3.50 (d, 1H); 3.75 (d, 1H); 4.31 (d, 1H); 4.60 (d, 1H); 5.0–5.38 (m, 3H); 5.52 (d, 1H); 5.8 (m, 1H); 6.5 (s, 1H); 9.49 (s, 1H).

EXAMPLE 8

The process described in Example 5 was repeated using 2-fluoro-4-hydroxyiminomethyl-1-triphenylmethylimidazole as starting material and water/MeOH/HOAc 80:20:1 v/v/v as the HPLC eluant. The product, 3-acetoxymethyl-7-(4-hydroxyiminomethylimidazol-2-yl)aminoceph-3-em-4-carboxylic acid, was obtained as a 1:1 mixture of E and Z isomers and had the following n.m.r. in d$_6$DMSO+CD$_3$COOD: 2.05 (s, 3H); 3.45 (d, 1H); 3.70 (d, 1H); 4.7 (d, 1H); 5.04 (d, 1H); 5.17 (d, 1H); 5.72 (d, 1H); 6.81 (s, 0.5H); 7.11 (s, 0.5H); 7.20 (s, 0.5H); 7.80 (s, 0.5H).

The 2-fluoro-4-hydroxyiminomethyl-1-triphenylmethylimidazole used as starting material may be obtained as follows:

To a stirred mixture of 4-formyl-2-fluoro-1-triphenylmethylimidazole (0.356 g.) and hydroxylamine hydrochloride (0.035 g.) in ethanol (4 ml.) was added pyridine (0.2 ml.). Stirring was continued at ambient temperature for 18 hours and the precipitated solid was filtered to give 2-fluoro-4-hydroxyiminomethyl-1-triphenylmethylimidazole, m.p. 147°–149°. Further amounts of product could be isolated from the mother liquors.

EXAMPLE 9

The process described in Example 5 was repeated using the appropriate starting materials and the following compounds are thus obtained:

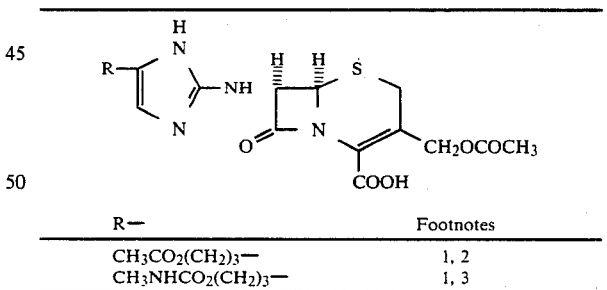

| R— | Footnotes |
|---|---|
| $CH_3CO_2(CH_2)_3-$ | 1, 2 |
| $CH_3NHCO_2(CH_2)_3-$ | 1, 3 |

Footnotes
1. H.P.L.C. eluant: - water/MeOH/HOAc 70:30:1 v/v/v.
2. Product had the following n.m.r. in d$_6$DMSO + CD$_3$CO$_2$D: - 1.80 (m, 2H); 2.00 (s, 3H); 2.04 (s, 3H); 2.5 (t, 2H); 3.51 (q, 2H); 4.02 (t, 2H); 4.89 (q, 2H); 5.13 (d, 1H); 5.55 (d, 1H); 6.60 (s, 1H).
3. Product had the following n.m.r. in d$_6$DMSO + CD$_3$CO$_2$D: - 1.80 (m, 2H); 2.03 (s, 3H); 2.4 (t, 2H); 2.57 (s, 3H); 3.50 (q, 2H); 3.96 (t, 2H); 4.90 (q, 2H); 5.12 (d, 1H); 5.57 (d, 1H); 6.56 (s, 1H).

The starting materials used in the above process may be obtained as follows:

A solution of 2-fluoro-4-(3-hydroxy)propyl-1-triphenylmethylimidazole (386 mg. in dry pyridine (2 ml.) and acetyl chloride (78.5 µl) was heated with stirring at 85° for 100 minutes. The solution was poured into water (25 ml.) and the mixture extracted with CH$_2$Cl$_2$ (3×15 ml.). The extract was washed with water and brine, dried (MgSO4), filtered, evaporated, and the residue azeotroped with toluene. The resulting orange oil was purified by column chromatography on silica gel eluting with CH2Cl2/MeOH 100:0 to 98:2 v/v to give 4-(3-acetoxy)propyl-2-fluoro-1-triphenylmethylimidazole (127 mg.) having the following n.m.r. in CDCl3: 1.9 (m, 2H); 2.02 (s, 3H); 2.47 (t, 2H); 4.07 (t, 2H) 6.22 (s, 1H); 7.0-7.5 (m, 15H).

A solution of 2-fluoro-4-(3-hydroxy)-propyl-1-triphenylmethylimidazole (386 mg) and methylisocyanate (100 μl.) in dry pyridine (2 ml.) was heated with stirring at 85° for 2 hours. The solution was poured into water (25 ml.) and the mixture extracted with CH2Cl2 (3×15 ml.). The extract was washed with water, brine, dried (MgSO4) filtered, evaporated and the residue azeotroped with toluene. The resulting colourless oil was purified by column chromatography on silica gel eluting with CH2Cl2/MeOH 100:0 to 98:2 v/v to give 2-fluoro-4-(3-methylcarbamoyloxy)propyl-1-triphenylmethylimidazole (280 mg.) having the following n.m.r. in d6DMSO: 1.8 (m, 2H); 2.40 (t, 2H); 2.53 (s, 3H); 3.94 (t, 2H); 6.30 (s, 1H); 7.0-7.5 (m, 15H).

EXAMPLE 10

A suspension of 7-amino-3-[1,2,3-triazol-5-yl]thiomethylceph-3-em-4-carboxylic acid (0.156 g.), 2-fluoro-4-(2-trifluoroacetylamino)ethylimidazole (0.190 g.) and toluene-p-sulphonic acid monohydrate (0.095 g.) in DMF (2 ml., dried over molecular sieve) was stirred at 80°-85° for 2.5 hours. The solution was evaporated to a gum which was partitioned between EtOAc and water. The aqueous phase was purified by preparative HPLC on Whatman "Partisil 10" using water/MeOH/HOAc 65:35:1 v/v/v as eluant, to give 3-(1,2,3-triazol-5-yl)thiomethyl-7-[4-(2-trifluoroacetylamino)ethylimidazol-2-yl]aminoceph-3-em-4-carboxylic acid (0.017 g.), having the following n.m.r. in d6DMSO+CD3COOD: 2.6 (t, 2H); 3.38 (t, 2H); 3.59 (d, 2H); 4.0 (s, 2H); 5.06 (d, 1H); 5.48 (d, 1H); 6.53 (s, 1H); 7.8 (s, 1H).

EXAMPLES 11-14

As a general process, 7-imidazolylamino cephalosporins were prepared as follows.

A solution of a substituted 2-fluoro-1-triphenylmethylimidazole (1 mM) in dry DMF (2 ml.) was treated with toluene-p-sulphonic acid monohydrate (1 mM) and stirred at 85° for 5 minutes, monitoring the loss of the triphenylmethyl group by HPLC. The appropriate 7-aminoceph-3-em-4-carboxylic acid (1 mM) was added, and heating continued for 2.5 hours, again monitoring the progress of the reaction by HPLC. The reaction mixture was then poured into the eluant to be used for purification (10 ml.), filtered and purified by preparative HPLC on Whatman "Partisil 10" using the indicated mixture of water/MeOH/HOAc, v/v/v.

Using this process, the following compounds were prepared.

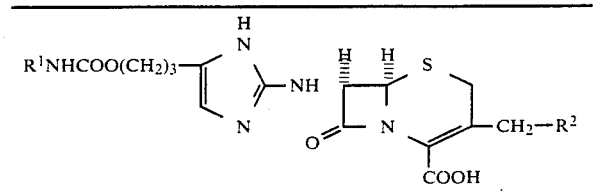

| Example | R¹— | —R² | HPLC eluant |
|---|---|---|---|
| 11 | Ph— | —OCOCH3 | 33:66:1 |
| 12 | CH3CO— | -S-[triazole] | 65:35:1 |
| 13 | [furyl]CO— | —OCOCH3 | 65:35:1 |
| 14 | [pyridyl] | —OCOCH3 | 65:35:1 |

Notes
The n.m.r. spectra of the products, obtained in d6DMSO + CD3CO2D, were as follows.
Example 11: 1.82 (m, 2H); 2.0 (s, 3H); 2.5 (t, 2H); 3.52 (q, 2H); 4.1 (t, 2H); 4.85 (q, 2H); 5.12 (d, 1H); 5.53 (d, 1H); 6.62 (s, 1H); 6.9-7.5 (m, 5H).
Example 12: 1.90 (m, 2H); 2.12 (s, 3H); 2.49 (t, 2H); 3.66 (q, 2H); 4.04 (q, 2H); 4.09 (t, 2H); 5.10 (d, 1H); 5.48 (d, 1H); 6.59 (s, 1H); 7.84 (s, 1H).
Example 13: 1.9 (m, 2H); 2.01 (s, 3H); 2.53 (t, 2H); 3.48 (q, 2H); 4.15 (t, 2H); 4.88 (q, 2H); 5.09 (d, 1H); 5.56 (d, 1H); 6.51 (s, 1H); 6.65 (m, 1H); 7.50 (m, 1H); 7.91 (m, 1H).
Example 14: 1.9 (m, 2H); 2.03 (s, 3H); 2.57 (t, 2H); 3.59 (q, 2H); 4.17 (t, 2H); 4.92 (q, 2H); 5.19 (d, 1H); 5.55 (d, 1H); 6.77 (s, 1H); 8.0-8.8 (m, 4H); toluene-p-sulphonate acid: 2.29 (s, 3H); 7.08 (d, 2H); 7.5 (d, 2H).

Starting materials used in the above process may be obtained as follows:

Example 11: A solution of 2-fluoro-4-(3-hydroxypropyl)-1-triphenylmethylimidazole in pyridine was treated with phenylisocyanate at ambient temperature. Work up as for the starting materials of Example 9 gave 2-fluoro-4-(3-phenylcarbamoyloxypropyl)-1-triphenylmethylimidazole, having the following n.m.r. spectrum in d6DMSO: 1.87 (m, 2H); 2.48 (t, 2H); 4.08 (t, 2H); 6.31 (s, 1H); 7.0-7.5 (m, 20H); 9.34 (br, 1H).

Example 12: A solution of 2-fluoro-4-(3-hydroxypropyl)-1-triphenylmethylimidazole in pyridine was treated with acetyl isocyanate at 85°. Work up as for the starting material of Example 11 gave 4-(3-acetylcarbamoyloxypropyl)-2-fluoro-1-triphenylmethylimidazole, having the following n.m.r. spectrum in d6DMSO: 1.82 (m, 2H); 2.12 (s, 3H); 2.45 (t, 2H) 4.05 (t, 2H); 6.28 (s, 1H); 7.0-7.5 (m, 15H); 10.12 (br, 1H).

Example 13: A suspension of 2-furoamide in 1,2-dichloroethane was treated with oxalyl chloride; 2-furoylisocyanate was isolated by distillation. This product was reacted with the hydroxypropylimidazole, as for the starting material of Example 12, to give 2-fluoro-4-[3-(fur-2-yl)carbamoyloxypropyl]-1-triphenylmethylimidazole, having the following n.m.r. in d6DMSO: 1.82 (m, 2H); 2.47 (t, 2H); 4.07 (t, 2H); 6.3 (s, 1H); 6.64 (m, 1H); 7.0-7.45 (m, 15H); 7.5 (m, 1H); 7.91 (m, 1H); 10.1 (br, 1H).

Example 14: A solution of the hydroxypropylimidazole was treated with 3-pyridylisocyanate as for the starting material of Example 12, to give 2-fluoro-4-[3-(pyrid-3-yl)carbamoyloxypropyl]-1-triphenylmethylimidazole having the following n.m.r. spectrum in CDCl$_3$: 1.97 (m, 2H); 2.5 (t, 2H); 4.16 (t, 2H); 6.25 (s, 1H); 6.9 (br s, 1H); 7.0–7.5 (m, 15H); 7.7–8.6 (m, 4H).

EXAMPLES 15–19

The process described in Example 11 was repeated, using the appropriate starting materials, to give the following compounds.

| Example | R$^1$— | —R$^2$ | HPLC eluant |
|---|---|---|---|
| 15 | —CN | —OCOCH$_3$ | 70:30:1 |
| 16 | —CN | —S-tetrazolyl-N-CH$_3$ | 80:20:1 |
| 17 | —COOH | —S-tetrazolyl-N-CH$_3$ | 75:25:1 |
| 18 | Cl-C$_6$H$_4$-NHCO— | —S-tetrazolyl-N-CH$_3$ | 50:50:1 |
| 19 | CH$_3$-C(=N-OCH$_3$)-Z | —OCOCH$_3$ | 60:40:1 |

Notes
The HPLC eluant was the indicated mixture of water/MeOH/HOAc, v/v/v. The n.m.r. spectra of the products, obtained in d$_6$DMSO + CD$_3$CO$_2$D, were as follows.
Example 15: 1.97 (s, 3H); 2.75 (m, 4H); 3.39 (d, 1H); 3.65 (d, 1H); 4.72 (d, 1H); 5.02 (d, 1H); 5.13 (d, 1H); 5.59 (d, 1H); 6.63 (s, 1H).
Example 16: 2.72 (br s, 4H); 3.62 (q, 2H); 3.77 (s, 3H); 4.29 (br s, 2H); 5.05 (d, 1H); 5.54 (d, 1H); 6.59 (s, 1H).
Example 17: 2.4–2.8 (m, 4H); 3.68 (d, 2H); 3.95 (s, 3H); 4.33 (br s, 2H); 5.09 (d, 1H); 5.52 (d, 1H); 6.68 (s, 1H).
Example 18: 2.3–2.95 (m, 4H); 3.71 (br s, 2H); 3.95 (s, 3H); 4.32 (br s, 2H); 5.15 (d, 1H); 5.54 (d, 2H); 6.72 (s, 1H); 7.0–7.7 (m, 4H).
Example 19: 1.8 (s, 3H); 2.04 (s, 3H); 2.5 (m, 4H); 3.4 (d, 1H); 3.64 (d, 1H); 3.74 (s, 3H); 4.76 (d, 1H); 5.04 (d, 1H); 5.13 (d, 1H); 5.61 (d, 1H); 6.52 (s, 1H).

Starting materials used in the above process may be obtained as follows:

Examples 15 and 16: Diethyl cyanomethylphosphonate was converted to its anion with sodium hydride in dimethoxyethane solution. An equal volume of DMF was added, followed by 2-fluoro-4-formyl-1-triphenylmethylimidazole. Reaction at room temperature gave 4-(2-cyanovinyl)-2-fluoro-1-triphenylmethyl imidazole. A suspension of this in MeOH was reduced by magnesium turnings to give 4-(2-cyanoethyl)-2-fluoro-1-triphenylmethylimidazole, having the following n.m.r. spectrum in CDCl$_3$: 2.71 (t, 4H); 6.42 (s, 1H); 7.1–7.4 (m, 15H).

Example 17: 2-Fluoro-4-formyl-1-triphenylmethylimidazole and ethoxycarbonylmethylene triphenylphosphorane were heated at 100°. Work-up by chromatography gave 4-(2-ethoxycarbonylvinyl)-2-fluoro-1-triphenylmethylimidazole, which was reduced using Adams catalyst in EtOAc to give 4-(2-ethoxycarbonylethyl)-2-fluoro-1-triphenylmethylimidazole. This ester was dissolved in dioxan, and hydrolysed at ambient temperature by 2N aqueous NaOH. Extractive work-up and trituration with ether gave 4-(2-carboxyethyl)-2-fluoro-1-triphenylmethylimidazole. It was characterised by means of its $^{13}$C n.m.r. spectrum in CDCl$_3$: (downfield from tetramethylsilane) 23.51; 33.53; 74.75; 113.6; 127.8; 128.0; 129.1; 129.3; 141.4; 149.1 and 177.2 p.p.m.

Example 18: A solution of 4-(2-carboxyethyl)-2-fluoro-1-triphenylmethylimidazole in CH$_2$Cl$_2$ was treated with triethylamine. The mixture was cooled, isobutyl chloroformate added, and stirred for 25 min. 4-Chloroaniline was then added, and stirring continued for 1 hour. Extractive work-up, followed by chromatography, gave 4-[2-(4-chlorophenylcarbamoyl)ethyl]-2-fluoro-1-triphenylmethylimidazole, having the following n.m.r. spectrum in CDCl$_3$+d$_6$DMSO: 2.4–2.75 (m, 4H); 6.25 (s, 1H); 6.9–7.65 (m, 19H); 9.9 (br s, 1H).

Example 19: 2-Fluoro-4-formyl-1-triphenylmethylimidazole and acetyl triphenyl phosphorane were reacted in toluene at 100° over 18 hours to give E-2-fluoro-4-(3-oxobut-1-enyl)-1-triphenylmethylimidazole. This was hydrogenated in a mixture of EtOAC and EtOH, using 5% w/w palladium on carbon as catalyst, to give 2-fluoro-4-(3-oxobutyl)-1-triphenylmethylimidazole. This was treated in EtOH with O-methylhydroxylamine hydrochloride and pyridine. Evaporation of solvent and trituration with water gave 2-fluoro-4-(3-methoxyiminobutyl)-1-triphenylmethylimidazole as a mixture of isomers, the major Z-isomer having the following n.m.r. spectrum in CDCl$_3$: 1.84 (s, 3H); 2.4–2.7 (m, 4H); 3.86 (s, 3H); 6.37 (s, 1H); 7.1–7.4 (m, 15H).

EXAMPLES 20–25

Using the appropriate starting materials, the process of Example 11 was repeated, except that for Example 24 two equivalents of toluene-p-sulphonic acid were used. The following compounds were obtained.

| Example | R$^1$— | —R$^2$ | HPLC eluant |
|---|---|---|---|
| 20 | CH$_3$CO— | —OCOCH$_3$ | 75:25:1 |
| 21 | CH$_3$CO— | —S-tetrazolyl-N-CH$_3$ | 75:25:1 |
| 22 | CF$_3$CO— | —OCOCH$_3$ | 70:30:1 |
| 23 | CH$_3$SO$_2$— | —OCOCH$_3$ | 75:25:1 |

-continued

| Example | R¹— | —R² | HPLC eluant |
|---|---|---|---|
| 24 | H₂N-(thiazol)-CH₂CO— | —S-(tetrazol-N-CH₃) | 77.5:22.5:1 |
| 25 | C₂H₅—N(piperazine-2,3-dione)—CO— | —S-(tetrazol-N-CH₃) | 60:40:1 |

Notes
The HPLC eluant was the indicated mixture of water/MeOH/HOAc, v/v/v. The n.m.r. spectra of the products, obtained in d₆DMSO + CD₃CO₂D, were as follows: -
Example 20: 1.69 (t, 2H); 1.8 (s, 3H); 2.0 (s, 3H); 2.4 (t, 2H); 3.06 (t, 2H); 3.44 (q, 2H); 4.93 (q, 2H); 5.11 (d, 1H); 5.74 (d, 1H); 6.59 (s, 1H); 7.98 (br, 1H); 8.9 (br, 1H).
Example 21: 1.63 (t, 2H); 1.78 (s, 3H); 2.33 (t, 2H); 3.03 (t, 2H); 3.47 (d, 1H); 3.73 (d, 1H); 3.89 (s, 3H); 4.29 (br s, 2H); 5.05 (d, 1H); 5.5 (d, 1H); 6.6 (s, 1H).
Example 22: 1.78 (m, 2H); 2.0 (s, 3H); 2.4 (sh); 3.23 (t, 2H); 3.48 (q, 2H); 4.9 (q, 2H); 5.1 (d, 1H); 5.63 (d, 1H); 6.57 (s, 1H); 8.3 (br, 1H); 9.46 (br, 1H).
Example 23: 1.7 (quintet, 2H); 2.0 (s, 3H); 2.5 (t, 2H); 2.88 (s, 3H); 2.94 (t, 2H); 3.49 (d, 2H); 4.88 (q, 2H); 5.1 (d, 1H); 5.54 (d, 1H); 6.6 (s, 1H).
Example 24: 1.72 (quintet, 2H); 2.5 (t, 2H); 3.03 (t, 2H); 3.28 (s, 2H); 3.74 (s, 2H); 3.95 (s, 3H); 4.32 (s, 2H); 5.15 (d, 1H); 5.55 (d, 1H); 6.25 (s, 1H); 6.77 (s, 1H); toluene-p-sulphonic acid: - 2.28 (s, 3H); 7.12 (d, 12H); 7.51 (d, 2H).
Example 25: 1.10 (t, 3H); 1.76 (quintet, 2H); 2.5 (t, 2H); 3.1–3.75 (m, 8H); 3.94 (s, 3H); 3.94 (q, 2H); 4.31 (s, 2H); 5.08 (d, 1H); 5.55 (d, 1H); 6.55 (s, 1H).

Starting materials for the above process may be obtained as follows:

Examples 20, 21: 4-(2-Cyanoethyl)-2-fluoro-1-triphenylmethylimidazole was suspended in an ethanolic solution of cobalt chloride hexahydrate, and reduced by the addition of several portions of sodium borohydride. The mixture was diluted with water, filtered through diatomaceous earth, and the filtrate extracted with ether. Crude 4-(3-aminopropyl)-2-fluoro-1-triphenylmethylimidazole was obtained by evaporation and azeotroping with toluene. It was dissolved in dry pyridine and treated with acetyl chloride; extractive work-up and chromatography gave 4-(3-acetamidopropyl)-2-fluoro-1-triphenylmethylimidazole, having the following n.m.r. spectrum in CDCl₃: 1.87 (quintet, 2H); 1.93 (s, 3H); 2.47 (t, 2H); 3.27 (q, 2H); 6.26 (br s, 2H); 7.0–7.5 (m, 15H).

Example 22: Crude 4-(3-aminopropyl)-2-fluoro-1-triphenylmethylimidazole was prepared as in Example 20, dissolved in CH₂Cl₂ and treated with triethylamine and trifluoroacetic anhydride for 1 hour. Workup as for Example 20 gave 2-fluoro-4-(3-trifluoroacetylaminopropyl)-1-triphenylmethylimidazole, having the following n.m.r. spectrum in CDCl₃: 1.86 (quintet, 2H); 2.54 (t, 2H); 3.43 (q, 2H); 6.28 (s, 1H); 7.0–7.5 (m, 15H); 8.18 (br, 1H).

Example 23: Using the same procedure as for the starting material of Example 20, but replacing acetyl chloride with methanesulphonyl chloride, there was obtained 2-fluoro-4-(3-methanesulphonamidopropyl)-1-triphenylmethylimidazole, which was unstable and used without further characterisation.

Example 24: Crude 4-(3-aminopropyl)-2-fluoro-1-triphenylmethylimidazole was prepared as for the starting material of Example 20 and reacted in THF with 2-triphenylmethylaminothiazol-4-ylacetic acid by the mixed anhydride procedure described for the starting material of Example 18, to give 2-fluoro-1-triphenylmethyl-4-[3-(2-triphenylmethylaminothiazol-4-ylacetylamino)-propyl]imidazole, having the following n.m.r. spectrum in CDCl₃: 1.68 (quintet, 2H); 2.4 (t, 2H); 3.16 (q, 2H); 3.34 (s, 2H); 6.07 (s, 1H); 6.21 (s, 1H); 7.0–7.5 (m, 30H).

Example 25: Crude 4-(3-aminopropyl)-2-fluoro-1-triphenylmethylimidazole was dissolved in CH₂Cl₂ and treated with 4-dimethylaminopyridine and a solution of 1-chlorocarbonyl-4-ethylpiperazine-2,3-dione in CH₂Cl₂. Work-up by chromatography gave 4-[3-(2,3-dioxo-4-ethylpiperazine-1-carbonylamino)propyl]-2-fluoro-1-triphenylmethylimidazole, having the following n.m.r. spectrum in CDCl₃: 1.25 (t, 3H); 1.85 (quintet, 2H); 2.25–3.7 (m, 6H); 4.05 (q, 2H); 6.25 (s, 1H); 7.05–7.5 (m, 15H).

EXAMPLE 26–38

Using the appropriate starting materials, the process of Example 11 was repeated, except that for Examples 35 and 37 two equivalents of toluene-p-sulphonic acid were used. The following compounds were obtained.

| Example | R¹— | —R² | HPLC eluant |
|---|---|---|---|
| 26 | —NO₂ | —OCOCH₃ | 70:30:1 |
| 27 | —NO₂ | —S-(tetrazol-N-CH₃) | 75:25:1 |
| 28 | —NO₂ | —S-(triazol-NH) | 70:30:1 |
| 29 | CH₃CONH— | —OCOCH₃ | 80:20:1 |
| 30 | (isoxazol)-CONH— | —OCOCH₃ | 70:30:1 |
| 31 | CH₃-(isoxazol)-CONH— | —OCOCH₃ | 65:35:1 |

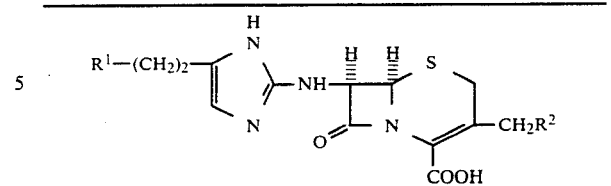

| Example | R¹— | —R² | HPLC eluant |
|---|---|---|---|
| 32 | ![structure: isoxazole-CONH-] (5-methylisoxazol-3-yl)CONH— | —OCOCH₃ | 70:30:1 |
| 33 | pyridazin-4-yl-CONH— | —OCOCH₃ | 70:30:1 |
| 34 | (2-oxo-1,2-dihydropyrimidin-5-yl)CONH— | —OCOCH₃ | 75:25:1 |
| 35 | (2-amino-thiazol-4-yl)CH₂CONH— | —OCOCH₃ | 80:20:1 |
| 36 | CH₃NHCONH— | —OCOCH₃ | 80:20:1 |
| 37 | (pyridin-3-yl)NHCONH— | —OCOCH₃ | 75:25:1 |
| 38 | CH₃SO₂NH— | —S-(1-methyl-1H-tetrazol-5-yl) | 80:20:1 |

Notes
The HPLC eluant was the indicated mixture of water/MeOH/HOAc, v/v/v. The n.m.r. spectra of the products, obtained in d₆DMSO + CD₃CO₂D, were as follows: -
Example 26: 2.0 (s, 3H); 3.02 (t, 2H); 3.52 (d, 2H); 4.72 (t, 2H); 4.84 (q, 2H); 5.1 (d, 1H); 5.57 (d, 1H); 6.46 (s, 1H).
Example 27: 3.03 (t, 2H); 3.64 (d, 2H); 3.92 (s, 3H); 4.3 (s, 2H); 4.72 (t, 2H); 5.08 (d, 1H); 5.55 (d, 1H); 6.48 (s, 1H).
Example 28: 3.09 (t, 2H); 3.66 (d, 2H); 3.97 (d, 2H); 4.75 (t, 2H); 5.09 (d, 1H); 5.5 (d, 1H); 6.58 (s, 1H); 7.88 (s, 1H).
Example 29: 1.8 (s, 3H); 2.0 (s, 3H); 2.6 (t, 2H); 3.28 (t, 2H); 3.5 (d, 2H); 4.9 (q, 2H); 5.14 (d, 1H); 5.55 (d, 1H); 6.64 (s, 1H).
Example 30: 1.99 (s, 3H); 2.72 (t, 2H); 3.46 (d, 2H); 3.5 (t, 2H); 4.84 (q, 2H); 5.10 (d, 1H); 5.52 (d, 1H); 6.62 (s, 1H); 7.66 (d, 2H); 8.62 (d, 2H).
Example 31: 2.04 (s, 3H); 2.5 (s, 3H); 2.7 (t, 2H); 3.48 (t, 2H); 3.52 (d, 2H); 4.91 (q, 2H); 5.15 (d, 1H); 5.63 (d, 1H); 6.52 (s, 1H); 6.61 (s, 1H).
Example 32: 2.0 (s, 3H); 2.4 (s, 3H); 2.64 (t, 2H); 3.44 (t, 2H); 3.47 (d, 2H); 4.87 (q, 2H); 5.14 (d, 1H); 5.64 (d, 1H); 6.55 (s, 1H); 8.35 (s, 1H).
Example 33: 2.01 (s, 3H); 2.72 (t, 2H); 3.48 (d, 2H); 3.51 (t,2H); 4.88 (q, 2H); 5.09 (d, 1H); 5.61 (d, 1H); 6.63 (s, 1H); 7.94 (q, 1H); 9.38 (q, 1H); 9.5 (d, 1H).
Example 34: 2.02 (s, 3H); 2.64 (t, 2H); 3.48 (m, 4H); 4.89 (q, 2H); 5.13 (d, 1H); 5.62 (d, 1H); 6.55 (s, 1H); 8.1 (s, 1H).
Example 35: 2.03 (s, 3H); 2.6 (t, 2H); 3.25 (s, 2H); 3.25 (t, 2H); 3.58 (d, 2H); 4.87 (q, 2H); 5.17 (d, 1H); 5.55 (d, 1H); 6.19 (s, 1H); 6.72 (s, 1H); toluene-p-sulphonic acid: - 2.28 (s, 3H); 7.08 (d, 2H); 7.47 (d, 2H).
Example 36: 2.1 (s, 3H); 2.59 (m, 2H); 3.3 (m, 2H); 3.58 (q, 2H); 4.98 (q, 2H); 5.2 (d, 1H); 5.64 (d, 1H); 6.63 (s, 1H).
Example 37: 2.04 (s, 3H); 2.68 (t, 2H); 3.37 (t, 2H); 3.6 (s, 2H); 4.9 (q, 2H); 5.2 (d, 1H); 5.58 (d, 1H); 6.85 (s, 1H); 7.26 (q, 1H); 7.87 (d, 1H); 8.12 (d, 1H); 8.55 (d, 1H); toluene-p-sulphonic acid: - 2.28 (s, 3H); 7.08 (d, 2H); 7.47 (d, 2H).
Example 38: 2.64 (t, 2H); 2.86 (s, 3H); 3.17 (t, 2H); 3.66 (d, 2H); 3.93 (s, 3H); 4.31 (s, 2H); 5.09 (d, 1H); 5.52 (d, 1H); 6.62 (s, 1H).

Starting materials for the above Examples may be obtained as follows:

Examples 26–28: 2-Fluoro-4-formyl-1-triphenylmethylimidazole (10.7 g.) and anhydrous potassium carbonate (91 mg.) were added to redistilled nitromethane (180 ml.). The mixture was stirred for 20 hours at ambient temperature, after which precipitated 2-fluoro-4-(1-hydroxy-2-nitroethyl)-1-triphenylmethylimidazole was filtered off. A solution of this compound in 1,2-dimethoxyethane was treated with pyridine, a catalytic amount of 4-dimethylaminopyridine and acetic anhydride. After stirring overnight, the mixture was evaporated to dryness and triturated with ether, to give 2-fluoro-4-(2-nitrovinyl)-1-triphenylmethylimidazole.

This was suspended in methylated spirits and reduced by sodium borohydride at 30°. The product was precipitated by addition of water, and purified by chromatography to give 2-fluoro-4-(2-nitroethyl)-1-triphenylmethylimidazole, having the following n.m.r. spectrum in d₆DMSO: 3.0 (t, 2H); 4.7 (t, 2H); 6.44 (s, 1H); 6.9–7.5 (m, 15H).

Example 29: A solution of cobalt chloride hexahydrate in methylated spirits was treated with 2-fluoro-4-(2-nitroethyl)-1-triphenylmethylimidazole, and reduced at <30° C. with portions of sodium borohydride. Extractive work-up, as for the starting material of Example 20, gave crude 4-(2-aminoethyl)-2-fluoro-1-triphenylmethylimidazole. This was treated with acetylchloride, by the technique of Example 20, to give 4-(2-acetylaminoethyl)-2-fluoro-1-triphenylmethylimidazole, having the following n.m.r. spectrum in CDCl₃: 1.9 (s, 3H); 2.6 (t, 2H); 3.5 (q, 2H); 6.3 (s, 1H); 7.0–7.5 (m, 15H).

Example 30: Use of the same technique as for the starting material of Example 29, but replacing acetyl chloride with isonicotinoyl chloride gave 2-fluoro-4-(2-isonicotinoylaminoethyl)-1-triphenylmethylimidazole, having the following n.m.r. spectrum in CDCl₃: 2.7 (t, 2H); 3.71 (q, 2H); 6.35 (s, 1H); 7.0–7.5 (m, 15H); 7.65 (q, 2H); 8.72 (q, 2H).

Example 31: 5-Methylisoxazole-3-carboxylic acid and 4-(2-aminoethyl)-2-fluoro-1-triphenylmethylimidazole were reacted by the mixed anhydride procedure described for the starting material of Example 24, to give 2-fluoro-4-[2-(5-methylisoxazole-3-carboxamido)ethyl]-

1-triphenylmethylimidazole. It had the following n.m.r. spectrum in $d_6$DMSO: 2.5 (s, 3H); 2.7 (t, 2H); 3.7 (q, 2H); 6.3 (s, 1H); 6.4 (s, 1H); 7.0–7.4 (m, 15H).

Example 32: By the same procedure as for the starting material of Example 31, but using 2-methyloxazole-4-carboxylic acid, 2-fluoro-4-[2-(2-methyloxazole-4-carboxamido)ethyl]-1-triphenylmethylimidazole was prepared, having the following n.m.r. spectrum in CDCl$_3$: 2.4 (s, 3H); 2.7 (t, 2H); 3.6 (q, 2H); 6.3 (s, 1H); 7.0–7.5 (m, 15H); 8.0 (s, 1H).

Example 33: By the same procedure as for the starting material of Example 31, but using pyridazine-4-carboxylic acid, 2-fluoro-4-[2-(4-pyridazinecarboxamido)ethyl]-1-triphenylmethylimidazole was prepared, having the following n.m.r. spectrum in CDCl$_3$: 2.7 (t, 2H); 3.72 (q, 2H); 6.34 (s, 1H); 7.0–7.45 (m, 15H); 7.81 (q, 1H); 8.2 (s, 1H); 9.32 (q, 1H); 9.56 (q, 1H).

Example 34: The same procedure as for the starting material of Example 31 was used, except that the solvent was DMF, and the acid 2,4-dihydroxypyrimidine-5-carboxylic acid. The product, 4-[2-(2,4-dihydroxy-5-pyrimidinecarboxamido)ethyl]-2-fluoro-1-triphenylmethylimidazole, had the following n.m.r. spectrum in CDCl$_3$: 2.78 (t, 2H); 3.7 (t, 2H); 6.42 (s, 1H); 7.1–7.5 (m, 15H); 8.7 (s, 1H); 8.93 (s, 1H).

Example 35: The same procedure as for the starting material of Example 31 was used, starting with 2-triphenylmethylaminothiazole-4-acetic acid. The product, 2-fluoro-1-triphenylmethyl-4-[2-(2-triphenylmethylaminothiazole-4-acetamido)ethyl]imidazole had the following n.m.r. spectrum in CDCl$_3$: 2.5 (t, 2H); 3.3 (s, 2H); 3.35 (q, 2H); 6.0 (s, 1H); 6.25 (s, 1H); 6.6 (s, 1H); 6.9–7.4 (m, 30H).

Example 36: 4-(2-Aminoethyl)-2-fluoro-1-triphenylmethylimidazole was dissolved in ether, treated with methylisocyanate, and stirred overnight at ambient temperature. Work-up gave 1-[2-(2-fluoro-1-triphenylmethylimidazol-4-yl)ethyl]-3-methylurea, having the following n.m.r. spectrum in CDCl$_3$: 2.54 (t, 2H); 2.7 (d, 3H); 3.35 (q, 2H); 5.1 (m, 1H); 6.4 (m, 1H); 6.3 (s, 1H); 7.2 (m, 15H).

Example 37: Using the same procedure as for the starting material of Example 36, except that CH$_2$Cl$_2$ was used as solvent, and 3-pyridylisocyanate in place of methyl isocyanate, there was obtained 1-[2-(2-fluoro-1-triphenylmethylimidazol-4-yl)ethyl]-3-(pyrid-3-yl)urea, having the following n.m.r. spectrum in $d_6$DMSO: 2.5 (t, 2H); 3.28 (t, 2H); 6.33 (s, 1H); 7.0–7.5 (m, 16H); 7.83 (d, 1H); 8.17 (s, 1H); 8.6 (s, 1H).

Example 38: Using the same procedure as for the starting material of Example 29 but using methanesulphonyl chloride in place of acetyl chloride, there was obtained 2-fluoro-4-(2-methanesulphonylaminoethyl)-1-triphenylmethylimidazole, which was used without further characterisation.

EXAMPLE 39

The bis toluene-p-sulphonate salt of t-butyl 3-acetoxymethyl-7-[4-(2-carbamoylethyl)imidazol-2-yl]aminoceph-3-em-4-carboxylate (318 mg.) was dissolved in TFA (10 ml), precooled to 0°, and stirred for 2 hours at this temperature. The solvent was evaporated, replaced by MeOH, and re-evaporated. The residue was purified by preparative HPLC, using water/MeOH/HOAc 80:20:1 v/v/v as eluant, to give the toluene-p-sulphonate salt of 3-acetoxymethyl-7-[4-(2-carbamoylethyl)imidazol-2-yl]aminoceph-3-em-4-carboxylic acid, having the following n.m.r. in $d_6$DMSO+CD$_3$CO$_2$D: 1.93 (s, 3H); 2.57 (m, 4H); 3.49 (q, 2H); 4.64 (d, 1H); 4.95 (d, 1H); 5.08 (d, 1H); 5.46 (d, 1H); 6.6 (s, 1H); Toluene-p-sulphonic acid: 2.19 (s, 3H); 7.02 (d, 2H); 7.41 (d, 2H).

The starting material may be prepared as follows:

4-(2-Cyanoethyl)-2-fluoro-1-triphenylmethylimidazole was dissolved in acetone and treated with aqueous KOH. Hydrogen peroxide was added in portions over seven days at ambient temperature. Extractive work-up and trituration with ether gave 4-(2-carbamoylethyl)-2-fluoro-1-triphenylmethylimidazole, having the following n.m.r. spectrum in CDCl$_3$: 2.58 (m, 4H); 5.3 (br s, 1H; 6.0 (br s, 1H); 6.26 (s, 1H); 7.0–7.35 (m, 15H).

The above imidazole was heated in dry CH$_3$CN with toluene-p-sulphonic acid monohydrate for 5 minutes at 85°. t-Butyl 3-acetoxymethyl-7-aminoceph-3-em-4-carboxylate was added, and heating continued for 1.25 hours. Work-up as for the starting material of Example 3 gave t-butyl 3-acetoxymethyl-7-[4-(2-carbamoylethyl)imidazol-2-yl]aminoceph-3-em-4-carboxylate as a bis toluene-p-sulphonate salt, having the following n.m.r. spectrum in CD$_3$OD: 1.54 (s, 9H); 2.07 (s, 3H); 2.52 (t, 2H); 2.72 (t, 2H); 3.54 (d, 1H); 3.61 (d, 1H); 4.76 (d, 1H); 5.10 (d, 1H); 5.15 (d, 1H); 5.54 (d, 1H); 6.54 (s, 1H); toluene-p-sulphonic acid: 2.37 (s, 6H); 7.25 (q, 8H).

EXAMPLE 40

Using the same process as for Example 39, except that the appropriate starting material was dissolved in a mixture of CH$_2$Cl$_2$ and TFA, there was obtained 3-acetoxymethyl-7-[4-(3-isobutoxycarbonylaminopropyl)imidazol-2-yl]aminoceph-3-em-4-carboxylic acid, after purification by HPLC using water/MeOH/H$_2$O 50:50:1 v/v/v, having the following n.m.r. spectrum in $d_6$DMSO+CD$_3$CO$_2$D: 0.89 (d, 6H); 1.63 (m, 3H); 2.05 (s, 3H); 2.46 (m, 2H); 3.03 (t, 2H); 3.40 (d, 1H); 3.66 (d, 1H); 3.75 (d, 2H); 4.76 (d, 1H); 5.05 (d, 1H); 5.14 (d, 1H); 5.57 (d, 1H); 6.58 (s, 1H).

The starting material may be prepared as follows:

4-(3-Aminopropyl)-2-fluoro-1-triphenylmethylimidazole was dissolved in THF and treated with N-methylmorpholine and isobutylchloroformate. Extractive work-up followed by chromatography gave 2-fluoro-4-(3-isobutoxycarbonylaminopropyl)-1-triphenylmethylimidazole.

Using the same procedure as for the starting material of Example 39, the above imidazole was reacted with t-butyl 3-acetoxymethyl-7-aminoceph-3-em-4-carboxylate to give t-butyl 3-acetoxymethyl-7-[4-(3-isobutoxycarbonylaminopropyl)imidazol-2-yl]aminoceph-3-em-4-carboxylate, having the following n.m.r. spectrum in CDCl$_3$: 0.9 (d, 6H); 1.52 (s, 9H); 1.76 (m, 3H); 2.07 (s, 3H); 2.48 (t, 2H); 3.2 (q, 2H); 3.42 (q, 2H); 3.83 (d, 2H); 4.75 (d, 1H); 5.08 (d, 1H); 5.05 (d, 1H); 5.65 (d, 1H); 6.35 (s, 1H).

EXAMPLES 41–43

The process described in Example 39 was repeated using the appropriate starting materials to give the following compounds.

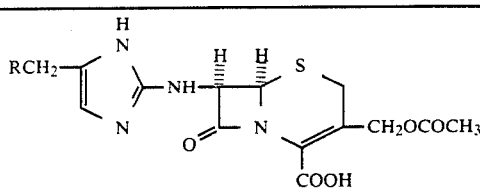

| Example | R— | Notes |
|---|---|---|
| 41 | N₃— | 1 |
| 42 | CH₃O— | 2, 3 |
| 43 | CH₃S— | 2, 4 |

Notes
1. Product purified by precipitation from ether with pentane; n.m.r. spectrum obtained in CDCL₃ + CD₃OD.
2. Product purified by silica gel chromatography, eluting with a mixture of CH₂Cl₂/MeOH/HCOOH 9:1:1 v/v/v, and precipitating the product from ether.
3. N.m.r. spectrum obtained in d₆DMSO.
4. N.m.r. spectrum obtained in d₆DMSO + CD₃CO₂D.
The products had the following n.m.r. spectra: -
Example 41: 2.08 (s, 3H); 3.6 (m, 2H); 4.38 (s, 2H); 4.9 (d, 1H); 5.15 (d, 1H); 5.2 (d, 1H); 5.55 (d, 1H); 6.85 (s, 1H).
Example 42: 2.0 (s, 3H); 3.3 (s, 3H); 3.4 (d, 1H); 3.7 (d, 1H); 4.3 (s, 2H); 4.7 (d, 1H); 5.1 (d, 1H); 5.2 (d, 1H); 5.6 (d, 1H); 7.0 (s, 1H).
Example 43: 2.0 (s, 6H); 3.4 (m, 2H); 3.7 (m, 2H); 4.7 (d, 1H); 5.1 (d, 1H); 5.1 (d, 1H); 5.65 (d, 1H); 6.7 (s, 1H).

Starting materials for the above process may be obtained as follows:

Example 41: 2-Fluoro-4-formyl-1-triphenylmethylimidazole was dissolved in a 2:1 (v/v) mixture of THF and isopropanol and treated with sodium borohydride at 20°. After 5 minutes the reaction was quenched with water. Extractive work-up and final trituration with MeOH gave 2-fluoro-4-hydroxymethyl-1-triphenylmethylimidazole. This was reacted with methanesulphonyl chloride and triethylamine in CH₂Cl₂ at ambient temperature to give 4-chloromethyl-2-fluoro-1-triphenylmethylimidazole. This was treated at ambient temperature in a water/THF solution with sodium azide, and crude product deprotected with toluene-p-sulphonic acid in CH₂Cl₂, to give 4-azidomethyl-2-fluoroimidazole as its toluene-p-sulphonate salt. This was reacted at 60° for 4 hours in DMF with t-butyl 3-acetoxymethyl-7-aminoceph-3-em-4-carboxylate. The product was purified by silica gel chromatography at −20°, using as eluant CH₂Cl₂/MeOH/HOAc 96:2:2 v/v/v, to give t-butyl 3-acetoxymethyl-7-(4-azidomethylimidazol-2-yl)aminoceph-3-em-4-carboxylate, having the following i.r. spectrum: νmax (film) 1680; 1725; 1745; 1790; 2110 cm⁻¹.

Example 42: 4-Chloromethyl-2-fluoro-1-triphenylmethylimidazole was dissolved in MeOH, and allowed to stand 1 hour, giving 2-fluoro-4-methoxymethyl-1-triphenylmethylimidazole. This was reacted at 60° for 3 hours in CHCl₃/MeOH solution with t-butyl 3-acetoxymethyl-7-aminoceph-3-em-4-carboxylate in the presence of toluene-p-sulphonic acid, and the product purified by chromatography to give t-butyl 3-acetoxymethyl-7-(4-methoxymethylimidazol-2-yl)aminoceph-3-em-4-carboxylate, having the following n.m.r. spectrum in d₆DMSO: 1.5 (s, 9H); 2.05 (s, 3H); 3.3 (s, 3H); 3.5 (d, 1H); 3.7 (d, 1H); 4.3 (s, 2H); 4.7 (d, 1H); 5.0 (d, 1H); 5.2 (d, 1H); 5.7 (d, 1H); 7.1 (s, 1H).

Example 43: 4-Chloromethyl-2-fluoro-1-triphenylmethylimidazole was treated with methanethiol and triethylamine in THF solution to give 2-fluoro-4-methylthiomethyl-1-triphenylmethylimidazole. This was condensed with t-butyl 3-acetoxymethyl-7-aminoceph-3-em-4-carboxylate as for the starting material of Example 42 to give t-butyl 3-acetoxymethyl-7-(4-methylthi-omethylimidazol-2-yl)aminoceph-3-em-4-carboxylate, having the following n.m.r. spectrum in d₆DMSO: 1.5 (s, 9H); 2.0 (s, 6H); 3.5 (d, 2H); 3.8 (d, 2H); 4.7 (d, 1H); 5.0 (d, 1H); 5.25 (d, 1H); 5.65 (d, 1H); 7.0 (s, 1H).

EXAMPLES 44–47

The process described in Example 11 was repeated, using the appropriate starting materials, to give the following compounds.

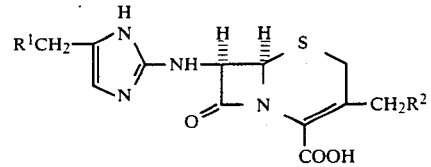

| Example | R¹— | —R² | HPLC eluant |
|---|---|---|---|
| 44 | —CN | (S-[1,3,4-thiadiazol], N—N, N—N, CH₃) | 82.5:17.5:1 |
| 45 | —CN | (S-[1,2,3-triazol], N, N—N, H) | 80:20:1 |
| 46 | (Ph-CH₂N(COCF₃)—) | —OCOCH₃ | 40:60:1 |
| 47 | (H₂N-thiazol-CH₃) | (S-tetrazol, N—N, N—N, CH₃) | 85:15:1 |

Notes
The HPLC eluant was the indicated mixture of water/MeOH/HOAc v/v/v. The n.m.r. spectra of the products, obtained in d₆DMSO + CD₃CO₂D, were as follows:
Example 44: 3.5 (d, 1H); 3.63 (s, 2H); 3.75 (d, 1H); 3.94 (s, 3H); 4.2 (d, 1H); 4.4 (d, 1H); 5.1 (d, 1H); 5.6 (d, 1H); 6.56 (s, 1H).
Example 45: 3.5 (d, 1H), 3.8 (d, 1H); 3.7 (s, 2H); 3.84 (d, 1H); 4.06 (d, 1H); 5.1 (d, 1H); 5.55 (d, 1H); 6.64 (s, 1H); 7.86 (s, 1H).
Example 46: 2.0 (s, 3H); 3.4 (d, 1H); 3.64 (d, 1H); 4.28 (m, 2H); 4.62 (m, 2H); 4.64 (d, 1H); 5.02 (d, 1H); 5.11 (d, 1H); 5.62 (d, 1H); 6.44, 6.55 (conformational isomers, 1H); 7.1–7.35 (m, 5H).
Example 47: 2.1 (s, 3H); 3.8 (m, 4H); 3.98 (s, 3H); 4.35 (m, 2H); 5.18 (d, 1H); 5.58 (d, 1H); 6.7 (s, 1H). 1.2 moles of toluene-p-sulphonic acid was also present: 2.29 (s, 3H); 7.08 (d, 2H); 7.5 (d, 2H).

Starting materials used in the above process may be obtained as follows:

Examples 44, 45: Toluene-p-sulphonylmethyl isocyanide, dissolved in dimethoxyethane, was added to a suspension of potassium t-butoxide in the same solvent at −30°. The mixture was cooled to −50° and treated with a solution of 2-fluoro-4-formyl-1-triphenylmethylimidazole in THF plus dimethoxyethane. After 45 minutes, MeOH was added and the mixture heated under reflux briefly. Extractive work-up gave 4-cyanomethyl-2-fluoro-1-triphenylmethylimidazole, having the following n.m.r. spectrum in CDCl₃: 3.53 (s, 2H); 6.57 (s, 1H); 7.05–7.45 (m, 15H).

Example 46: A solution of 2-fluoro-4-formyl-1-triphenylmethylimidazole in CH₂Cl₂ was treated at ambient temperature for 18 hours with benzylamine. After changing solvent to MeOH, sodium borohydride was added, and the mixture allowed to stand for 2 hours. Work-up gave 4-benzylaminomethyl-4-fluoro-1-triphenylmethylimidazole. This was dissolved in CH₂Cl₂ and treated with triethylamine and trifluoroacetic anhydride. Evaporation and trituration with ether gave 4-(N-benzyl-trifluoroacetylaminomethyl)-2-fluoro-1-triphenylmethylimidazole, having the following n.m.r. spectrum in CDCl₃: 4.25 (m, 2H); 4.7 (m, 2H); 6.3 (s, 1H); 6.4 (s, 1H); 7.1–7.5 (m, 20H).

Example 47: 2-Fluoro-4-(3-oxobutyl)-1-triphenylmethylimidazole was dissolved in dimethoxyethane and treated with triethylamine and trimethylsilyl trifluoromethylsulphonate at 0°. The resulting silyl enolate was treated with N-bromosuccinimide for 30 minutes at ambient temperature, followed by thiourea. Reaction overnight at ambient temperature gave a mixture after extractive work-up, in which the desired 4-(2-amino-4-methylthiazol-5-ylmethyl)-2-fluoro-1-triphenylmethylimidazole could be identified by its n.m.r. spectrum in CDCl₃, having resonances at 2.32 (s, 3H); 3.88 (s, 2H); 6.48 (s, 1H); 7.04–7.6 (m, 15H). It was used without further purification in the condensation with the 7-aminocephalosporin.

EXAMPLES 48–51

The process described in Example 11 was repeated, using the appropriate starting materials, to give the following compounds.

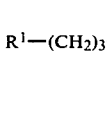

| Example | R¹— | —R² | HPLC eluant |
|---|---|---|---|
| 48 | N₃— | —OCOCH₃ | 60:40:1 |
| 49 | CH₃O— | —OCOCH₃ | 70:30:1 |
| 50 | C₂H₅S(=O)— | 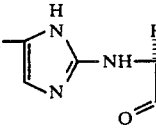 | 65:35:1 |
| 51 | C₂H₅S(=O)₂— | 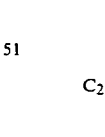 | 70:30:1 |

Notes:
The HPLC eluant was the indicated mixture of water/MeOH/HOAc v/v/v. The n.m.r. spectra of the products, obtained in d₆DMSO + CD₃CO₂D, were as follows.
Example 48: 1.9 (2H); 2.07 (s, 3H); 2.52 (t, 2H); 3.4 (t, 2H); 3.58 (q, 2H); 4.91 (q, 2H); 5.18 (d, 1H); 5.61 (d, 1H); 6.63 (s, 1H).
Example 49: 1.85 (m, 2H); 2.0 (s, 3H); 2.5 (t, 2H); 3.24 (s, 3H); 3.34 (t, 2H); 3.51 (q, 2H); 4.88 (q, 2H); 5.11 (d, 1H); 5.56 (d, 1H); 6.6 (s, 1H).
Example 50: 1.06 (t, 3H); 1.75 (m, 2H); 2.3–2.7 (m, 6H); 3.53 (q, 2H); 3.8 (s, 3H); 4.2 (brs, 2H); 4.98 (d, 1H); 5.43 (d, 1H); 6.55 (s, 1H).
Example 51: 1.17 (t, 3H); 1.85 (m, 2H); 2.5 (t, 2H); 3.04 (m, 4H); 3.64 (q, 2H); 3.91 (s, 3H); 4.3 (s, 2H); 5.06 (d, 1H); 5.55 (d, 1H); 6.59 (s, 1H).

Starting materials for the above process may be obtained as follows:

Example 48: A solution of 2-fluoro-4-(3-hydroxypropyl)-1-triphenylmethylimidazole in pyridine was treated with methanesulphonyl chloride. Work-up as for the starting material of Example 9 gave 2-fluoro-4-(3-methanesulphonyloxypropyl)-1-triphenylmethylimidazole, having the following n.m.r. spectrum in CDCl₃: 2.03 (m, 2H); 2.52 (t, 2H); 2.94 (s, 3H); 4.21 (t, 2H); 6.27 (s, 1H); 7.0–7.5 (m, 15H).

A solution of the above compound in dimethoxyethane and DMF was treated with tetramethylguanidinium azide at 85°. Work-up as above gave 4-(3-azidopropyl)-2-fluoro-1-triphenylmethylimidazole, having the following n.m.r. in CDCl₃: 1.86 (m, 2H); 2.47 (t, 2H); 3.23 (t, 2H); 6.22 (s, 1H); 7.0–7.5 (m, 15H).

Example 49: A solution of 2-fluoro-4-(3-methanesulphonyloxypropyl)-1-triphenylmethylimidazole in MeOH was treated with sodium metal and stirred at 65°. Work-up as for the starting material of Example 9 gave 2-fluoro-4-(3-methoxypropyl)-1-triphenylmethylimidazole, having the following n.m.r. in CDCl₃: 1.87 (m, 2H); 2.45 (t, 2H); 3.26 (s, 3H); 3.33 (t, 2H); 6.21 (s, 1H); 7.0–7.5 (m, 15H).

Example 50: A solution of ethanethiol in DMF was treated with sodium hydride, and then with 2-fluoro-4-(3-methanesulphonyloxypropyl)-1-triphenylmethylimidazole. After stirring at ambient temperature for 16 hours, the mixture was worked up by extraction and chromatography to give 4-(3-ethylthiopropyl)-2-fluoro-1-triphenylmethylimidazole, having the following n.m.r. in CDCl₃: 1.2 (t, 3H); 1.85 (quintet, 2H); 2.48 (q, 6H); 6.24 (s, 1H); 7.0–7.4 (m, 15H). This thioether was dissolved in CH₂Cl₂, cooled to 0°, and treated in portions with one equivalent of 3-chloroperbenzoic acid, having the reaction closely by HPLC. Complete conversion to product occurred 10 minutes after the final addition of peracid. The solution was extracted with aqueous sodium bicarbonate, dried and evaporated to give 4-(3-ethanesulphinylpropyl)-2-fluoro-1-triphenylmethylimidazole, having the following n.m.r. in CDCl₃: 1.28 (t, 3H); 2.02 (quintet, 2H); 2.66 (m, 6H); 6.27 (s, 1H); 7.0–7.4 (m, 15H).

Example 51: Using the same technique as for the starting material of Example 50, but using two equivalents of 3-chloroperbenzoic acid, there was obtained 4-(3-ethanesulphonylpropyl)-2-fluoro-1-triphenylmethylimidazole, having the following n.m.r. in CDCl₃: 1.35 (t, 3H); 2.09 (quintet, 2H); 2.58 (t, 2H); 2.84 (q, 4H); 6.29 (s, 1H); 7.0–7.4 (m, 15H).

EXAMPLES 52–56

The process of Example 11 was repeated, using the appropriate starting materials, to give the following compounds:

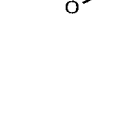

| Example | R¹— | —R² | Probable stereochemistry of CH=CH | HPLC eluant |
|---|---|---|---|---|
| 52 | H— | 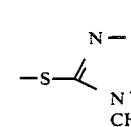 | — | 70:30:1 |
| 53 | CH₂=CH— | 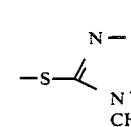 | Z | 60:40:1 |

-continued

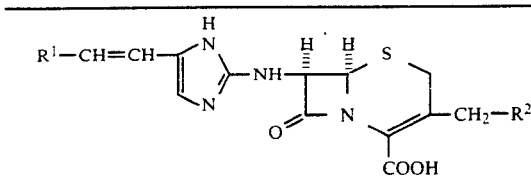

| Example | R¹— | —R² | Probable stereo-chemistry of CH=CH | HPLC eluant |
|---|---|---|---|---|
| 54 | CH≡C— | —OCOCH₃ | E | 60:40:1 |
| 55 | Z CH₃—C(=NOCH₃)/ | —OCOCH₃ | E | 55:45:1 |
| 56 | Z CH₃—C(=NOCH₃)/ | —S—⟨N—N / N—N⟩—CH₃ (tetrazole) | E | 50:50:1 |

Notes:
The HPLC eluant was the indicated mixture of water/MeOH/HOAc, v/v/v. The n.m.r. spectra of the products, obtained in d₆DMSO + CD₃CO₂D, were as follows:
Example 52: 3.56 (d, 1H); 3.76 (d, 1H); 3.92 (s, 3H); 4.3 (s, 2H); 5.02 (d, 1H); 5.11 (d, 1H); 5.5 (d, 1H); 5.63 (s, 1H); 6.23–6.6 (m, 1H); 6.77 (s, 1H).
Example 53: 3.66 (d, 2H); 3.92 (s, 3H); 4.29 (d, 2H); 4.95–5.3 (m, 3H); 5.68 (d, 1H); 5.94 (t, 2H); 6.7 (s, 1H); 7.1–7.8 (m, 2H).
Example 54: 2.04 (s, 3H); 3.42 (d, 1H); 3.66 (d, 1H); 4.28 (d, 1H); 4.75 (d, 1H); 5.03 (d, 1H); 5.15 (d, 1H); 5.3 (q, 1H); 5.7 (d, 1H); 6.57 (d, 1H); 7.1 (s, 1H).Example 55: 1.92 (s, 3H); 2.0 (s, 3H); 3.4 (d, 1H); 3.7 (d, 1H); 3.8 (s, 3H); 4.7 (d, 1H); 5.04 (d, 1H); 5.15 (d, 1H); 5.68 (d, 1H); 6.48 (d, 1H); 6.57 (s, 1H); 6.9 (d, 1H).
Example 56: 2.0 (s, 3H); 3.64 (d, 1H); 3.82 (d, 1H); 3.86 (s, 3H); 4.0 (s, 3H); 4.3 (d, 1H); 4.4 (d, 1H); 5.17 (d, 1H); 5.71 (d, 1H); 6.56 (d, 1H); 6.68 (s, 1H); 6.96 (d, 1H).

Starting materials for the above Examples may be obtained as follows:

Example 52: Methyl triphenylphosphonium iodide was treated with potassium t-butoxide in DMSO. After generation of the phosphorane, 2-fluoro-4-formyl-1-triphenylmethylimidazole was added, and the mixture heated 2 hours at 60°. Extractive work-up and chromatography gave 2-fluoro-1-triphenylmethyl-4-vinylimidazole, having the following n.m.r. in CDCl₃: 5.1 (d, 1H); 5.77 (d, 1H); 6.26–6.63 (m, 1H); 6.48 (s, 1H); 7.1–7.5 (m, 15H).

Example 53: 2-Fluoro-4-formyl-1-triphenylmethylimidazole was reacted with allyl triphenyl phosphonium bromide in CH₂Cl₂ in the presence of aqueous NaOH to give 4-(buta-1,3-dienyl)-2-fluoro-1-triphenylmethylimidazole having the following n.m.r. spectrum in CDCl₃: 5.06–5.39 (m, 2H); 5.87 (d, 1H); 6.06 (dd, 1H); 6.49 (s, 1H); 7.51 and 7.7 (d of t, 3H); 7.08–7.44 (br, 15H).

Example 54: (3-Trimethylsilylprop-2-ynyl)triphenyl phosphonium bromide in THF was treated with n-butyllithium, and reacted at −78° with 2-fluoro-4-formyl-1-triphenylmethylimidazole for 1 hour. The solution was diluted with ether, filtered, and filtrate concentrated. Triphenylphosphine oxide was filtered off, and the filtrate evaporated. The solid residue was treated with 20% w/v methanolic KOH to precipitate E-4-(but-1-en-3-ynyl)-2-fluoro-1-triphenylmethylimidazole, having the following n.m.r. in CDCl₃: 3.02 (d, 1H); 5.4 (q, 1H); 6.6 (d, 1H); 7.4 (s, 1H); 7.05–7.38 (m, 15H).

Examples 55 and 56: E-2-Fluoro-4-(3-oxobut-1-enyl)-1-triphenylmethylimidazole in EtOH was treated with O-methylhydroxylamine hydrochloride and pyridine for 18 hours. Solvent was evaporated and 2-fluoro-4-(3-methoxyiminobut-1-enyl)-1-triphenylmethylimidazole isolated by crystallisation as a 3:1 mixture of isomers. The major Z, E-isomer had the following n.m.r. in CDCl₃: 1.96 (s, 3H); 3.9 (s, 3H); 6.48 (d, 1H); 6.6 (s, 1H); 7.04–7.4 (m, 16H).

EXAMPLES 57 and 58

The process of Example 11 was repeated, using the appropriate starting materials, to give the following compounds.

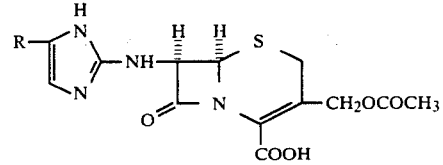

| Example | R— | HPLC eluant |
|---|---|---|
| 57 | CH₃ON=CH— | 77.5:22.5:1 |
| 58 | OHC—NH\C=CH—, CH₃—⟨C₆H₄⟩—SO₂ | 60:40:1 |

Notes:
The HPLC eluant was the indicated mixture of water/MeOH/HOAc v/v/v. Example 57 was obtained as a 1:1 mixture of Z and E isomers; Example 58 as a single isomer of unknown geometry, containing two molecules of toluene-p-sulphonic acid. The n.m.r. spectra, obtained in d₆DMSO + CD₃CO₂D, were as follows:
Example 57: 2.02 (s, 3H); 3.4 (d, 1H); 3.7 (d, 1H); 3.8 (s, 1.5H); 3.88 (s, 1.5H); 4.7 (d, 1H); 5.04 (d, 1H); 5.15 (d, 1H); 5.69 (d, 1H); 6.88 (s, 0.5H); 7.14 (s, 0.5H); 7.2 (s, 0.5H); 7.88 (s, 0.5H).
Example 58: 1.98 (s, 3H); 2.34 (s, 3H); 3.4 (d, 1H); 3.6 (d, 1H); 4.7 (d, 1H); 4.98 (d, 1H); 5.1 (d, 1H); 5.62 (d, 1H); 7.0–8.0 (m, 7H); plus toluene-p-sulphonic acid at 2.29 (s, 6H); 7.08 (d, 4H); 7.5 (d, 4H).

Starting materials for the above Examples may be obtained as follows:

Example 57: 2-Fluoro-4-formyl-1-triphenylmethylimidazole was reacted in EtOH with O-methylhydroxylamine hydrochloride and pyridine, to give 2-fluoro-4-methoxyimino-1-triphenylmethylimidazole, as a 3:1 mixture of geometrical isomers, having the following n.m.r. in CDCl₃: 3.87 (s, 0.75H); 3.93 (s, 0.25H); 7.05–7.5 (m, 17H).

Example 58: Toluene-p-sulphonylmethyl isocyanide was treated with potassium t-butoxide in 1,2-dimethoxyethane at −30°. 2-Fluoro-4-formyl-1-triphenylmethylimidazole was added in the same solvent, and reaction continued for 30 minutes. After addition of water 2-fluoro-4-[2-formylamino-2-(toluene-p-sulphonyl)-vinyl]-1-triphenylmethylimidazole precipitated, having the following n.m.r. in CDCl₃: 2.4 (s, 3H); 6.8 (s, 1H); 7.0 (br s, 1H); 7.05–7.4 (m, 18H); 7.76 (d, 2H); 8.5 (br s, 1H).

EXAMPLES 59–61

The process of Example 11 was repeated, using the appropriate starting materials, to give the following compounds.

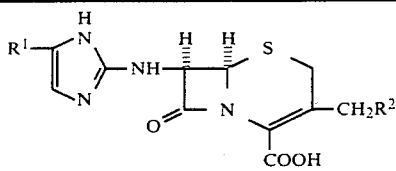 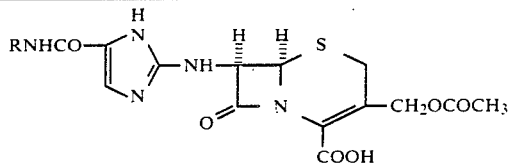

| Example | R¹— | —R² | HPLC eluant |
|---|---|---|---|
| 59 | HOCH₂CHOHCH₂— | [thiadiazole-S-] | 70:30:1 |
| 60 | H₂NCHCN (with | branch) | [methylthiadiazole-S-] | 85:15:1 |
| 61 | (CH₃)₂NCHCN (with | branch) | —OCOCH₃ | 80:20:1 |

Notes:
The HPLC eluant was the indicated mixture of water/MeOH/HOAc. v/v/v. The n.m.r. spectra, obtained in d₆DMSO + CD₃CO₂D, were as follows.
Example 59: 2.5 (m, 2H); 3.33 (d, 2H); 3.66 (d, 2H); 3.88 (m, 1H); 4.02 (s, 2H); 5.13 (d, 1H); 5.52 (d, 1H); 6.66 (s, 1H); 7.85 (s, 1H).
Example 60: 3.7 (m, 2H); 3.95 (s, 3H); 4.33 (s, 2H); 5.17 (d, 1H); 5.63 (d, 1H); 5.72 (s, 1H); 7.22 (s, 1H); 1 mole of toluene-p-sulphonic acid: −2.29 (s, 3H); 7.08 (d, 2H); 7.5 (d, 2H).
Example 61: 2.04 (s, 3H); 2.5 (under DMSO, 6H); 3.58 (d, 2H); 4.72 (d, 1H); 5.03 (d, 1H); 5.13 (d, 1H); 5.2 (s, 1H); 5.75 (d, 1H); 7.59 (s, 1H).

Starting materials for the above process may be obtained as follows:

Example 59: A solution of osmium tetroxide in acetone was treated with N-methylmorpholine in aqueous acetone. 4-Allyl-2-fluoro-1-triphenylmethylimidazole was added, and the mixture stirred at ambient temperature overnight. Reductive work-up with sodium metabisulphite and magnesium trisilicate, followed by extraction into ether, gave 4-(2,3-dihydroxypropyl)-2-fluoro-1-triphenylmethylimidazole, having the following n.m.r. in CDCl₃: 2.6 (d, 2H); 3.6 (m, 2H); 3.9 (m, 1H); 6.3 (s, 1H); 7.0–7.5 (m, 15H).

Example 60: An aqueous solution of NH₄Cl and NaCN was added to a solution of 2-fluoro-4-formyl-1-triphenylmethylimidazole in THF and EtOH. After stirring 2 hours at 20° and 5 minutes at 60°, the solution was evaporated and triturated with ether, to give 4-(1-aminocyanomethyl)-2-fluoro-1-triphenylmethylimidazole having the following n.m.r. in CDCl₃: 5.37 (s, 1H); 6.73 (s, 1H); 7.04–7.45 (m, 15H).

Example 61: An aqueous solution of dimethylamine hydrochloride and NaCN was added to a solution of 2-fluoro-4-formyl-1-triphenylmethylimidazole in THF. After stirring 3 hours at 20°, work-up gave 4-(1-dimethylaminocyanomethyl)-2-fluoro-1-triphenylmethylimidazole having the following n.m.r. in CDCl₃: 2.31 (s, 6H); 4.64 (s, 1H); 6.68 (s, 1H); 7.04–7.45 (m, 15H).

EXAMPLES 62–65

The process of Example 11 was repeated, using the appropriate starting materials, except that in Examples 64 and 65 two equivalents of toluene-p-sulphonic acid were used. The following compounds were obtained.

| Example | R— | HPLC eluant |
|---|---|---|
| 62 | CH₃— | 85:15:1 |
| 63 | phenyl- | 55:45:1 |
| 64 | (CH₃)₂N—⟨phenyl⟩— | 60:40:1 |
| 65 | (CH₃)₂N(CH₂)₃— | 87.5:12.5:1 |

Notes:
The HPLC eluant was the indicated mixture of water/MeOH/HOAc. v/v/v. The n.m.r. spectra, obtained in d₆DMSO + CD₃CO₂D, were as follows.
Example 62: 2.0 (s, 3H); 2.7 (s, 3H); 3.4 (d, 1H); 3.7 (d, 1H); 4.7 (d, 1H); 5.0 (d, 1H); 5.2 (d, 1H); 5.7 (d, 1H); 7.1 (s, 1H).
Example 63: 2.1 (s, 3H); 3.5 (d, 1H); 3.7 (d, 1H); 4.7 (d, 1H); 5.1 (d, 1H); 5.2 (d, 1H); 5.9 (d, 1H); 6.9–7.5 (m, 4H); 7.8 (d, 2H).
Example 64: 2.1 (s, 3H); 2.9 (s, 6H); 3.6 (m, 2H); 4.7 (d, 1H); 5.1 (d, 1H); 5.2 (d, 1H); 5.9 (d, 1H); 6.7 (d, 2H); 7.3 (s, 1H); 7.5 (d, 2H).
Example 65: 1.7 (m, 2H); 1.9 (s, 3H); 2.6 (s, 6H); 2.9 (t, 2H); 3.2 (t, 2H); 3.3 (d, 1H); 3.5 (d, 1H); 4.8 (q, 2H); 5.0 (d, 1H); 5.6 (d, 1H); 7.0 (s, 1H); plus 1 mole of toluene-p-sulphonic acid: −2.2 (s, 3H); 7.0 (d, 2H); 7.4 (d, 2H).

Starting materials for the above process may be obtained as follows:

Examples 62 and 64: Bromination of 2-fluoro-1-triphenylmethylimidazole with N-bromosuccinimide in DMF for 18 hours at ambient temperature gave 4-bromo-2-fluoro-1-triphenylmethylimidazole, m.p. 167°–169°. Reaction of this compound with n-butyl lithium at −75° followed by treatment with methyl isocyanate and 4-dimethylaminophenylisocyanate gave 4-methylcarbamoyl-2-fluoro-1-triphenylmethylimidazole, n.m.r. in CDCl₃: 3.0 (d, 3H); 6.9 (s, 1H); 7.1–7.5 (m, 16H) and 4-(4-dimethylaminophenyl)carbamoyl-2-fluoro-1-triphenylmethylimidazole, n.m.r. in CDCl₃: 3.0 (s, 6H); 6.8 (d, 2H); 7.1–7.7 (m, 18H); 8.5 (s, 1H), respectively.

Example 63: Reaction of 2-fluoro-1-triphenylmethylimidazole with n-butyl lithium at −75° followed by treatment with phenylisocyanate gave 2-fluoro-4-phenylcarbamoyl-1-triphenylmethylimidazole, n.m.r. in CDCl₃: 7.0–7.5 (m, 19H); 7.6 (d, 2H); 8.6 (s, 1H). Reaction of this product with toluene-p-sulphonic acid in DMF at 85° for 15 minutes gave 2-fluoro-4-phenylcarbamoylimidazole, n.m.r. in CDCl₃: 6.9–8.0 (m, 6H); 9.6 (s, 1H).

Example 65: 2-Fluoro-1-triphenylmethylimidazole-4-carboxylic acid and 3-dimethylaminopropylamine were condensed in THF by the mixed anhydride procedure described for the preparation of starting material for Example 18, to give 4-(3-dimethylaminopropylcarbamoyl)-2-fluoro-1-triphenylmethylimidazole, having the following n.m.r. in CDCl₃: 1.8 (m, 2H); 2.3 (s, 6H); 2.4 (t, 2H); 3.5 (q, 2H); 7.0–7.6 (m, 16H).

EXAMPLE 66

The process of Example 11 was repeated, using the appropriate starting materials, to give 3-acetoxymethyl-7-(4-propionylaminoimidazol-2-yl)aminoceph-3-em-4-carboxylic acid, after preparative HPLC using water/MeOH/HOAc, 70:30:1 v/v/v, was eluant. The product had the following n.m.r. in d₆DMSO: 1.03 (t, 3H); 2.05 (s, 3H); 2.23 (q, 2H); 3.45 (d, 1H); 3.65 (d, 1H); 4.7 (d, 1H); and 5.03 (d, 1H); 5.13 (d, 1H); 5.53 (dd, 1H); 6.65 (s, 1H); 6.85 (d, 1H).

Starting material for the above process may be obtained as follows:

A solution of 2-fluoro-1-triphenylmethylimidazole in THF was treated with t-butyllithium at −70° for 2 hours. A solution of toluene-p-sulphonyl azide in toluene was added, followed after 10 minutes by chlorotrimethylsilane, and the mixture allowed to come to 0°. Work-up and chromatography on magnesium silicate gave 4-azido-2-fluoro-1-triphenylmethylimidazole. This was dissolved in ether and treated with triphenylphosphine at 25°, to precipitate 2-fluoro-1-triphenylmethyl-4-(triphenylphosphimino)imidazole. A solution of this compound in EtOAc was treated for 10 minutes at 25° with propionyl chloride. Aqueous work-up, followed by magnesium silicate chromatography gave 2-fluoro-4-propionylamino-1-triphenylmethylimidazole, having the following n.m.r. in CDCl$_3$: 1.05 (t, 3H); 2.2 (q, 2H); 6.95 (s, 1H); 7.05–7.4 (m, 15H); 9.05 (s, 1H).

EXAMPLES 67–71

The process of Example 11 was repeated, using the appropriate starting materials, to give the following compounds.

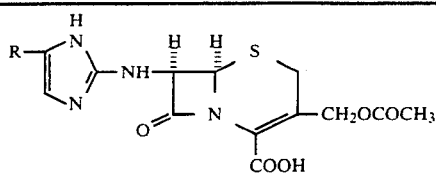

| Example | R— | HPLC eluant |
|---------|-----|-------------|
| 67 | ⬡—CONH\C=CH—/H$_2$NCO | 75:25:1 |
| 68 | ⬡—CONH\C=CH—/HOOC | 75:25:1 |
| 69 | ⬡—CONH\C=CH—/CH$_3$OCO | 60:40:1 |
| 70 | ⬡—CONH\CH—CH$_2$—/CH$_3$OCO | 65:35:1 |
| 71 | ⬡—CONH\CH—CH$_2$—/CH$_3$OCO | 60:40:1 |

Notes:
The compounds of Example 67–69 exists as one isomer, but of undetermined geometry. The HPLC eluant was the indicated mixture of water/MeOH/HOAc, v/v/v. The n.m.r. spectra, obtained in d$_6$DMSO + CD$_3$CO$_2$D, were as follows.
Example 67: 2.08 (s, 3H); 3.5 (s, 2H); 4.73 (d, 1H); 4.73 (d, 1H); 5.07 (d, 1H); 5.56 (d, 1H); 6.59 (s, 1H); 6.94 (s, 1H); 7.4–7.66 (m, 3H); 7.94–8.14 (m, 2H).
Example 68: 2.03 (s, 3H); 3.46 (brs, 2H); 4.76 (d, 1H); 4.65 (d, 1H); 5.0 (d, 1H); 5.56 (d, 1H); 6.83 (brs, 1H); 6.99 (s, 1H); 7.6–7.8 (m, 3H); 7.9–8.1 (m, 2H).
Example 69: 2.0 (s, 3H); 3.47 (brs, 2H); 3.67 (s, 3H); 4.8 (d, 1H); 4.69 (d, 1H); 5.05 (d, 1H); 5.61 (d, 1H); 6.82 (s, 1H); 7.05 (s, 1H); 7.4–7.6 (m, 3H); 7.91 (m, 2H).
Example 70: 1.91 (s, 3H); 2.94 (brd, 2H); 3.41 (brd, 2H); 3.58 (s, 3H); 4.66 (m, 1H); 4.65 (d, 1H); 4.95 (d, 1H); 5.03 (d, 1H); 5.47 (d, 1H); 6.57 (s, 1H); 7.32–7.5 (m, 3H); 7.66–7.85 (m, 2H).
Example 71: 1.0–2.4 (m, 11H); 2.02 (s, 3H); 2.82 (d, 2H); 3.62 (s, 3H); 3.35 (d, 1H); 3.64 (d, 1H); 4.44 (t, 1H); 4.72 (d, 1H); 5.03 (d, 1H); 5.1 (d, 1H); 5.58 (d, 1H); 6.49 (s, 1H).

Starting materials for the above process may be obtained as follows:

Example 67: A mixture of 2-fluoro-4-formyl-1-triphenylmethylimidazole, hippuric acid, and sodium acetate was treated with acetic anhydride. After heating for 2.25 hours at 50°, the mixture was poured into EtOH to precipitate 2-fluoro-4-(5-oxo-2-phenyl-4-oxazolinylidenemethyl)-1-triphenylmethylimidazole, having the following n.m.r. in CDCl$_3$: 7.0–7.6 (m, 21H); 7.93 (s, 1H). This azlactone was suspended in dioxan and treated with aqueous NH$_3$ (density 0.91 g./ml) for 20 minutes. Evaporation gave 4-(2-benzoylamino-2-carbamoylvinyl)-2-fluoro-1-triphenylmethylimidazole, having the following n.m.r. in CDCl$_3$+D$_2$O: 6.3 (d, 1H); 6.5 (s, 1H); 6.8–7.3 (m, 18H); 7.7–8.0 (m, 2H); 10.5 (br s, 1H).

Example 68: The azlactone from Example 67 was suspended in acetone and heated for 10 minutes on a steam bath. Addition of 2N HCl and extractive work-up gave 4-(2-benzoylamino-2-carboxyvinyl)-2-fluoro-1-triphenylmethylimidazole, having the following n.m.r. in CDCl$_3$: 6.88 (s, 1H); 6.95–7.7 (m, 19H); 8.1–8.3 (m, 2H); 13.09 (br s, 1H).

Example 69: The azlactone from Example 67 was suspended in MeOH and a catalytic quantity of sodium methoxide added. 4-(2-Benzoylamino-2-methoxycarbonylvinyl)-2-fluoro-1-triphenylmethylimidazole crystallised out, having the following n.m.r. in CDCl$_3$: 3.75 (s, 3H); 6.31 (d, 1H); 6.55 (s, 1H); 6.8–7.5 (m, 18H); 7.6–7.8 (m, 2H); 10.5 (br s, 1H).

Example 70: 4-(2-Benzoylamino-2-methoxycarbonylvinyl)-2-fluoro-1-triphenylmethylimidazole was hydrogenated in EtOAc using a prehydrogenated sodium—containing platinum oxide catalyst (Adams' catalyst), for 3 days. Removal of catalyst and evaporation gave 4-(2-benzoylamino-2-methoxycarbonylethyl)-2-fluoro-1-triphenylmethylimidazole, having the following n.m.r. in CDCl$_3$: 3.0 (d, 2H); 3.65 (s, 3H); 4.92 and 5.0 (d of t, 1H); 6.3 (s, 1H); 7.0–7.5 (m, 19H); 7.65–8.0 (m, 2H).

Example 71: 4-(2-Benzoylamino-2-methoxycarbonyl-vinyl)-2-fluoro-1-triphenylmethylimidazole was hydrogenated in EtOAc using prehydrogenated fully active platinum oxide catalyst (Adams' catalyst) for 2.5 days. Work-up gave 4-(2-cyclohexylcarbonylamino-2-methoxycarbonylethyl)-2-fluoro-1-triphenylmethylimidazole, having the following n.m.r. in CDCl$_3$: 1.0–2.3 (m, 11H); 2.85 (d, 2H); 3.6 (s, 3H); 4.2 and 4.27 (d of t, 1H); 6.24 (s, 1H); 6.8 (d, 1H); 7.0–7.5 (m, 15H).

EXAMPLES 72–77

The process of Example 11 was repeated, using the appropriate starting materials, to give the following compounds.

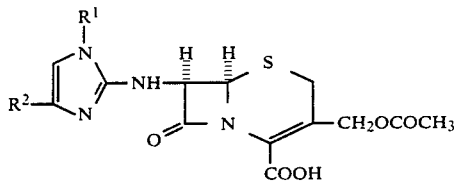

| Example | R$^1$— | R$^2$— | HPLC eluant |
|---|---|---|---|
| 72 | CH$_2$=CH—CH$_2$— | H— | 70:30:1 |
| 73 | CH$_2$=CH—CH$_2$— | CH$_2$=CH—CH$_2$— | 60:40:1 |
| 74 | C$_6$H$_5$—CH=CH—CH$_2$— | H— | 50:50:1 |
| 75 | CH≡C—CH$_2$— | H— | 80:20:1 |
| 76 | CH$_2$=C=CH— | H— | 70:30:1 |
| 77 | C$_2$H$_5$OCO(CH$_2$)$_3$— | H— | 70:30:1 |

Notes:
The HPLC eluant was the indicated mixture of water/MeOH/HOAc v/v/v. The n.m.r. spectra, obtained in d$_6$DMSO + CD$_3$CO$_2$D, were as follows.
Example 72: 1.9 (s, 3H); 3.3 (d, 1H); 3.6 (d, 1H); 4.4 (d, 2H); 4.5–5.2 (m, 5H); 5.5 (d, 1H); 5.6–6.0 (m, 1H); 6.6 (d, 1H); 6.7 (d, 1H).
Example 73: 2.0 (s, 3H); 3.2 (d, 2H); 3.4 (d, 1H); 3.6 (d, 1H); 4.4 (d, 2H); 4.6–5.3 (m, 7H); 5.6 (d, 1H); 5.7–6.0 (m, 2H); 6.4 (s, 1H).
Example 74: 2.0 (s, 3H); 3.3 (d, 1H); 3.6 (d, 1H); 4.6 (d, 2H); 4.8 (q, 2H); 5.1 (d, 1H); 5.6 (d, 1H); 6.3 (m, 2H); 6.6 (d, 1H); 6.8 (d, 1H); 7.3 (m, 5H).
Example 75: 1.9 (s, 3H); 3.2 (t, 1H); 3.3 (d, 1H); 3.6 (d, 1H); 4.7 (d, 2H); 4.8 (q, 2H); 5.0 (d, 1H); 5.7 (d, 1H); 6.6 (d, 1H); 6.8 (d, 1H).
Example 76: 1.9 (s, 3H); 3.3 (d, 1H); 3.6 (d, 1H); 4.7 (q, 2H); 5.0 (d, 1H); 5.4–5.6 (m, 3H); 6.5 (d, 1H); 6.6 (d, 1H); 7.3 (t, 1H).
Example 77: 1.2 (t, 3H); 1.8–2.4 (m, 4H); 2.0 (s, 3H); 3.5 (q, 2H); 3.8 (t 2H); 4.0 (q, 2H); 4.8 (q, 2H); 5.1 (d, 1H); 5.6 (d, 1H); 6.6 (d, 1H); 6.8 (d, 1H).

Starting materials for the above process may be obtained as follows:

Examples 72 and 73: 2-Fluoroimidazole hydrochloride, allyl bromide and a catalytic quantity of tetra-n-butylammonium hydrogen sulphate were added to a mixture of CH$_2$Cl$_2$ and 50% w/v aqueous NaOH. After stirring 3 days at 20°, the mixture was worked up by extraction and chromatography to give both 1-allyl-2-fluoroimidazole and 1,4-diallyl-2-fluoroimidazole. The compounds had the following n.m.r. spectra in CDCl$_3$:

Monoallyl: 4.4 (d of t, 2H); 5.0–5.4 (m, 2H); 5.7–6.2 (m, 1H); 6.6 (d, 1H); 6.7 (t, 1H).

Diallyl: 3.2 (d, 2H); 4.3 (d of t, 2H); 4.9–5.3 (m, 4H); 5.7–6.2 (m, 2H); 6.3 (s, 1H).

Example 74: 2-Fluoroimidazole hydrochloride was added to a suspension of powdered KOH in acetone, stirred for 10 minutes, and E-cinnamyl bromide added. After stirring 1 hour, the mixture was worked up by extraction and chromatography to give E-1-cinnamyl-2-fluoro-imidazole, having the following n.m.r. in CDCl$_3$: 4.6 (d, 2H); 6.1–6.4 (d of t, 1H); 6.6 (d, 1H); 6.6–6.8 (m, 2H); 7.2–7.5 (m, 5H).

Examples 75 and 76: 2-Fluoroimidazole hydrochloride was alkylated with propargyl bromide, using the same procedure as for the starting material of Example 74, to give a mixture of 2-fluoro-1-propargylimidazole and 1-allenyl-2-fluoroimidazole, separated by chromatography. The compounds had the following n.m.r. spectra in CDCl$_3$:

Propargyl derivative: 2.5 (t, 1H); 4.6 (d, 2H); 6.7 (d, 1H); 6.8 (t, 1H);

Allenyl derivatives: 5.6 (d, 2H); 6.7 (s, 2H); 6.8 (t, 1H).

Example 77: Using the technique for the starting material of Example 74, 2-fluoroimidazole hydrochloride was alkylated with ethyl 4-bromobutyrate to give ethyl 4-(2-fluoroimidazol-1-yl)butyrate, having the following n.m.r. in CDCl$_3$: 1.3 (t, 3H); 1.9–2.5 (m, 4H); 3.9 (t, 2H); 4.1 (q, 2H); 6.5 (d, 1H); 6.6 (d, 1H).

EXAMPLE 78

The process of Example 11 was repeated, using the appropriate starting materials, the product being purified by HPLC using water/MeOH/HOAc 60:40:1 v/v/v as eluant. This gave 3-acetoxymethyl-7-[1-(3-t-butoxycarbonylpropyl)imidazol-2-yl]aminoceph-3-em-4-carboxylic acid, having the following n.m.r. in d$_6$DMSO+CD$_3$COOD: 1.4 (s, 9H); 2.0 (s, 3H); 1.6–2.4 (m, 4H); 3.3 (d, 1H); 3.6 (d, 1H); 3.8 (t, 2H); 4.7 (d, 1H); 5.0 (d, 1H); 5.1 (d, 1H); 5.6 (d, 1H); 6.7 (d, 1H); 6.8 (d, 1H).

The starting material may be obtained as follows:

2-Fluoroimidazole was alkylated with t-butyl-4-chlorobutyrate, using the same procedure as that for the starting material of Example 74, to give 1-(3-t-butoxycarbonylpropyl)-2-fluoroimidazole.

EXAMPLE 79

3-Acetoxymethyl-7-[1-(3-t-butoxycarbonylpropyl)imidazol-2-yl]aminoceph-3-em-4-carboxylic acid was treated with TFA according to the process of Example 39, except that product was isolated by trituration, to give 3-acetoxymethyl-7-[1-(3-carboxypropyl)imidazol-2-yl]amino ceph-3-em-4-carboxylic acid, having the following n.m.r. spectrum in d$_6$DMSO+CD$_3$CO$_2$D: 1.6–2.4 (m, 4H); 2.0 (s, 3H); 3.5 (d, 1H); 3.7 (d, 1H); 4.0 (t, 2H); 4.7 (d, 1H); 5.0 (d, 1H); 5.2 (d, 1H); 5.6 (s, 1H); 7.1 (m, 2H).

EXAMPLES 80–81

The process of Example 11 was repeated, using the appropriate starting materials, to give the following compounds.

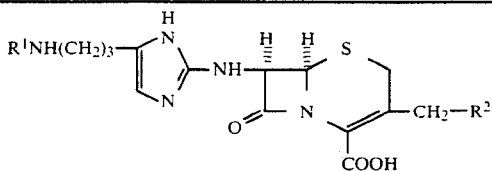

| Example | R¹— | —R² | HPLC eluant |
|---------|-----|-----|-------------|
| 80 | CF₃CH₂NHC̈S— | ![structure]-S—⟨thiadiazole-NH⟩ | 50:50:1 |
| 81 | NH₂CO— | ![structure]-S—⟨thiadiazole-CH₃⟩ | 75:25:1 |

Notes:
The HPLC eluant was the indicated mixture of water/MeOH/HOAc, v/v/v. The n.m.r. spectra, obtained in d₆DMSO + CD₃CO₂D were as follows:
Example 80: 1.8 (m, 2H); 2.48 (m, 2H); 3.46 (m, 4H); 4.01 (s, 2H); 5.04 (d, 1H); 5.48 (d, 1H); 6.54 (s, 1H); 7.81 (s, 1H).
Example 81: 1.63 (m, 2H); 2.5 (t, 2H); 3.03 (t, 2H); 3.66 (d, 2H); 3.93 (s, 3H); 4.32 (brs, 2H); 5.09 (d, 1H); 5.54 (d, 1H); 6.65 (s, 1H).

Starting materials for the above process may be obtained as follows:

Example 80: 4-(3-Aminopropyl)-2-fluoro-1-triphenylmethylimidazole was reacted in THF with 2,2,2-trifluoroethyl isothiocyanate for 2 hours. Extractive work-up and chromatography gave 2-fluoro-4-[3-(3-[2,2,2-trifluoroethyl]thioureido)propyl]-1-triphenylmethylimidazole having the following n.m.r. in CDCl₃: 1.78 (quintet, 2H); 2.43 (t, 2H); 3.5 (q, 2H); 4.25 (m, 2H); 6.24 (s, 1H); 7.0–7.35 (m, 15H).

Example 81: 4-(3-Aminopropyl)-2-fluoro-1-triphenylmethylimidazole was dissolved in THF and treated with aqueous KCNO. The mixture was stirred at 20°, and the pH reduced to 4 with 1N aqueous HCl. After 30 minutes an extractive work up followed by chromatography gave 2-fluoro-1-triphenylmethyl-4-(3-ureidopropyl)imidazole, having the following n.m.r. in d₆DMSO: 1.54 (quintet, 2H); 2.33 (t, 2H); 2.92 (q, 2H); 5.28 (s, 2H); 5.9 (t, 1H); 6.28 (s, 1H); 6.95–7.55 (m, 15H).

EXAMPLE 82

The process described in Example 11 was repeated, using the appropriate starting materials, and using as the HPLC eluant a mixture of MeOH and an aqueous solution of ammonium carbonate (2 g./l.) adjusted to pH 6 with CO₂ 27:73 v/v. There was thus obtained 7-(4-allylimidazol-2-yl)amino-3-chloroceph-3-em-4-carboxylic acid having the following n.m.r. in D₂O/TFA: 3.35 (m, 2H); 3.7 (d, 1H); 4.1 (d, 1H); 5.3 (m, 2H); 5.4 (d, 1H); 5.5 (d, 1H); 5.7–6.1 (m, 1H); 8.7 (s, 1H).

EXAMPLE 83

The process of Example 10 was repeated using the appropriate starting materials. The product was purified by HPLC using H₂O/MeOH/HOAc 60:40:1 v/v/v as eluant to give 3-acetoxymethyl-7-(1-t-butoxycarbonylmethylimidazol-2-yl)aminoceph-3-em-4-carboxylic acid having the following n.m.r. in d₆DMSO+CD₃COOD: 1.4 (s, 9H); 2.0 (s, 3H); 3.4 (d, 1H); 3.7 (d, 1H); 4.7 (s, 2H); 4.7 (d, 1H); 5.0 (d, 1H); 5.1 (d, 1H); 5.6 (d, 1H); 6.6 (d, 1H); 6.7 (d, 1H).

The starting material may be obtained as follows:
Alkylation of 2-fluoroimidazole hydrochloride with t-butyl bromoacetate using the same conditions as for the starting materials of Examples 72 and 73 gave t-butoxycarbonylmethyl-2-fluoroimidazole, n.m.r. in CDCl₃: 1.4 (s, 9H); 4.4 (s, 2H); 6.5 (d, 1H); 6.6 (t, 1H).

EXAMPLE 84

The product from Example 83 was treated with TFA to give 3-acetoxymethyl-7-(2-carboxymethylimidazol-2-yl)aminoceph-3-em-4-carboxylic acid trifluoroacetate having the following n.m.r. in d₆DMSO+CF₃COOD: 2.0 (s, 3H); 3.4 (d, 1H); 3.7 (d, 1H); 4.8 (s, 2H); 4.7 (d, 1H); 5.0 (d, 1H); 5.2 (d, 1H); 5.6 (d, 1H); 7.1 (d, 1H); 7.13 (d, 1H).

EXAMPLE 85

A mixture of 4-(2-ethoxycarbonyl-2-isocyanoethyl)-2-fluoro-1-triphenylmethylimidazole and DMF was heated at 85° for 10 minutes with 2 equivalents of toluene-p-sulphonic acid monohydrate in order to hydrolyse the isocyanide and remove the triphenylmethyl group. 7-Amino-3-(1H-1-methyltetrazol-5-yl)thiomethylceph-3-em-4-carboxylic acid was then added and heating was continued for 2.5 hours. The product was purified by HPLC using H₂O/MeOH/HOAc 75:25:1 v/v/v as eluant to give 7-[4-(2-ethoxycarbonyl-2-formylaminoethyl)imidazol-2-yl]amino-3-(1H-1-methyltetrazol-5-yl)thiomethylceph-3-em-4-carboxylic acid having the following n.m.r. in d₆DMSO+CD₃COOD: 1.08 (m, 3H); 2.68–3.0 (m, 2H); 3.68 (d, 2H); 3.91 (s, 3H); 4.09 (q, 2H); 4.3 (br s, 2H); 4.58 (t, 1H); 5.1 (d, 1H); 5.57 (d, 1H); 6.59 (s, 1H); 8.02 (s, 1H).

The starting material may be prepared as follows:
Reaction of 4-chloromethyl-2-fluoro-1-triphenylmethylimidazole with ethyl isocyanoacetate/potassium t-butoxide in THF followed by chromatography on silica gel gave 4-(2-ethoxycarbonyl-2-isocyanoethyl)-2-fluoro-1-triphenylmethylimidazole having the following n.m.r. in CDCl₃: 1.24 (t, 2H); 2.7–3.17 (d, 2H); 4.18 (q, 1H); 4.5 (dd, 1H); 6.4 (s, 1H); 7.0–7.4 (m, 15H).

What we claim is:
1. A cephalosporin derivative of the formula:

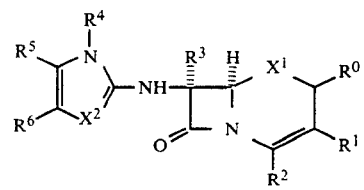

in which R⁰ is a hydrogen atom; R¹ is a hydrogen or halogen atom, a hydroxy or amino radical or a radical selected from:
(a) 1–6C alkyl, benzyl optionally substituted by fluorine or methoxy, 1–6C haloalkyl, formyl, carboxy, 1–6C alkoxy, 1–6C methylthio, 1–6C alkylamino, phenylamino, benzylamino, 3–6C cycloalkylamino, cyano, 2–6C alkoxycarbonyl, 2–6C alkanoyl, 3–10C alkoxycarbonylalkyl, 2–6C alkoxycarbonylamino, 2–6C alkylthiocarbonylamino, piperidino, pyrrolidino, morpholino, 2–6C alkanoylamino, ureido, 2–6C alkylureido, 3–8C dialkylureido, 1–6C alkanesulphinyl, 1–6C alkanesulphonyl, heterocyclyl and heterocyclylthio radicals in which the heterocycle is a 1,3,4- thiadiazol-2-yl or 1,3,4-oxadiazol-2-yl, each optionally substituted in the 5-position, a 1H-tetrazol-5-yl optionally substituted in the 1-position, or a 1H-1,2,3-triazol-4-yl radical optionally substituted in the 1 or 5 position, the optional substituents in each of these heterocycles being a 1–6C alkyl, a 1–6C sulphoalkyl, a 2–6C carboxyalkyl, a 1–6C haloalkyl or a 3–6C alkylthioalkyl radical or a pyridazin-3-yl, oxazol-3-yl or thiazol-3-yl each optionally substituted by 1 or 2 radicals selected from 1–6C alkyl, 1–6C haloalkyl and 2–6C alkoxycarbonyl radicals;

(b) radicals of the formula:

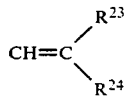

XIII in which $R^{23}$ and $R^{24}$, which may be the same or different, are hydrogen atoms, 1–6C alkyl, 5–7C cycloaliphatic, 6–12C aryl, 7–10C arylalkyl, formyl, cyano, carboxy, 2–6C alkoxycarbonyl, sulpho, 1–6C alkanesulphinyl, 1–6C alkanesulphonyl, 1–6C alkoxy, 1–6C alkylthio, carbamoyl, nitro, 1–6C hydroxyalkyl, methylcarbamoyloxymethyl, benzylcarbamoyloxymethyl, 2–6C alkoxymethyl, 2–6C alkylthiomethyl, 2-haloethoxymethyl, cyclopentyloxymethyl, benzyloxymethyl or 3–8C alkanoyloxymethyl radicals or radicals of the formula $CH_2SHet^1$ in which $Het^1$ is a 1,3,4-thiadiazol-2-yl or 1,3,4-oxadiazol-2-yl, both optionally substituted in the 5-position by a methyl radical, a 1H-triazol-5-yl radical optionally substituted in the 1-position by a methyl radical or a 1H-1,2,3-triazol-4-yl radical;

(c) radicals of the formula:

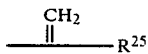

XIV in which $R^{25}$ is a cyano, carboxy or 2–6C alkoxycarbonyl radical;

(d) radicals of the formula:

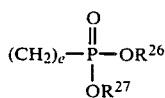

XV in which $R^{26}$ and $R^{27}$, which may be the same or different, are hydrogen atoms or 1–6C alkyl radicals and e is 1 to 4; and (e) radicals of the formula $CH_2Y$ in which Y is an atom or group which is the residue of a nucleophile or a derivative of a residue of a nucleophile, such a nucleophile or a derivative thereof being:
A. 3–15C trialkylamines;
B. heterocyclic amines having more than one heteroatom, at least heteroatom being nitrogen;
C. pyridines which are optionally substituted by 1 to 3 substituents selected from halogen atoms, and 1–6C alkyl, 6–10C aryl, 7–11C arylalkyl, 2–10C alkoxyalkyl, 3–10C alkanoyloxymethyl, formyl, carbamoyl, 2–6C alkanoyloxy, 2–6C alkoxycarbonyl, 1–6C alkoxy, 6–10C aryloxy, 7–11C aralkoxy, 1–6C alkylthio, 6–10C arylthio, 7–11C aralkylthio, cyano, hydroxy, 2–6C alkylcarbamoyl, 3–10C dialkylcarbamoyl, 2–6C (hydroxyalkyl)carbamoyl and 2–6C carbamoylalkyl radicals;
D. azide radicals;
E. amino, 1–6C alkanoylamino and 7–11C aroylamino radicals;
F. cyanide, pyrroles and substituted pyrroles;
G. nucleophiles giving rise to $R^1$ of the formula:

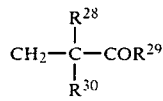

XVI in which $R^{28}$ and $R^{29}$, which may be the same or different, are selected from hydrogen atoms and cyano, 1–6C alkyl, 2–6C alkoxycarbonyl, 8–20C mono- or di-arylalkoxycarbonyl, 2–6C alkanoyl, 7–11C aralkyl, cyclopentyl and cyclohexyl radicals, and phenyl radicals optionally substituted by 1 or 2 radicals selected from halogen atoms and 1–6C alkyl, 1–6C alkoxy, 1–6C alkylamino, nitro and amino radicals, and $R^{30}$ is selected from hydrogen, 1–6C alkyl, 7–11C aralkyl, cyclopentyl and cyclohexyl radicals, and phenyl radicals optionally substituted by 1 or 2 radicals selected from halogen atoms, 1–6C alkyl, 1–6C alkoxy and 1–6C alkylamino radicals;
H. thiourea optionally substituted by a 1–6C alkyl, 6–10C aryl, 5–7C alicyclic or a heterocyclic radical, dithiocarbamates, thioamides substituted by a 1–6C alkyl or 6–10C aryl radical or thiosemicarbazides, thiosulphates, arylthioacids or heterocyclicthioacids of up to 10 carbon atoms and dithioacids of the formula:

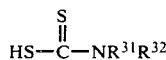

XVII in which $R^{31}$ and $R^{32}$ which may be the same or different, are hydrogen atoms, 1–6C alkyl, 2–6C hydroxyalkyl, 3–8C alkylaminoalkyl, 4–10C dialkylaminoalkyl or phenyl radicals, or $R^{31}$ and $R^{32}$ are joined to form a pyrrolidine, piperidine or morpholine ring or a piperazine ring which is optionally substituted on the nitrogen atom by one or two (in quarternised form) radicals selected from 1–6C alkyl and 3–6C alkenyl radicals;
I. radicals of the formula $R^{33}S(O)d-$ in which d is 0, 1 or 2 and $R^{33}$ is a 1–6C alkyl, 5–7C alicyclic, 6–10C aryl optionally substituted by a carboxy radical, or 7–11C arylalkyl radical or a 5- or 6-membered heterocyclic ring (partially or fully unsaturated) containing 1 to 4 nitrogen atoms which ring may further include oxygen and/or sulphur atoms, in which the nitrogen atom or atoms may be in the oxide form, which herterocyclic ring may be fused with another heterocyclic ring within the same definition or may be fused with a benzene ring, the above aryl, arylalkyl, heterocyclic or fused benzene ring being optionally substituted by 1 or 2 substituents selected from halogen atoms and 1–6C alkyl, 1–6C haloalkyl, 6–10C aryl, 2–6C alkenyl, 1–6C alkoxy, oxo, hydroxy, mercapto, amino, carboxy, cyano, isothiocyanato, carbamoyl, sulphamoyl, 2-6C alkoxycarbonyl, 3-6C alkenyloxycarbonyl, 8-12C aralkylcarbonyl, 7-11C aryloxycarbonyl, 2-6C hydroxyalkyl, 3-6C dihydroxyalkyl, sulphoamino and 1-6C alkanesulphonylamino radicals and radicals of the formula B—$R^{34}$ in which B is a 2-8C straight or branched chain which may be interrupted by a sulphur or oxygen atom or by an NH or 1-6C N-alkyl radical and $R^{34}$ is a radical selected from hydroxy, mercapto, cyano, 1-6C alkylamino, 2-6C dialkylamino, 2-6C alkanoylamino, carboxy, sulpho, carbamoyl, sulphamoyl, amidino, quinidino, 2-6C alkoxycarbonyl, 2-6C alkylcarbamoyl, 2-6C dialkylcarbamoyl, 1-6C alkylsulphamoyl, 2-6C dialkylsulphamoyl, sulphoamino, ureido, 1-6C alkoxy, 1-6C alkylthio, 1-6C alkanesulphonyl, 2-6C alkanoyl and 2-6C alkanoyloxy radicals and radicals of the formula —S—$R^{35}$ in which $R^{35}$ is a 1-6C alkyl radical or a group of the formula B—$R^{34}$ in which B and $R^{34}$ have the meanings given above and radicals of the formula $NR^{36}R^{37}$ in which $R^{36}$ and $R^{37}$, which may be the same or different, are selected from 1-6C alkyl radicals, groups of the formula B-$R^{34}$ in which B and $R^{34}$ have the definitions given above, 1-6C alkoxycarbonyl, 2-6C alkanoyl, carbamoyl, 2-6C alkylcarbamoyl and 3-10C dialkylcarbamoyl radicals;

J. radicals of the formula $R^{38}$—O— in which $R^{38}$ is a hydrogen atom, or a 1-6C alkyl, 3-6C alkenyl, 3-6C alkynyl, 5-7C cycloalkyl, 6-12C cycloalkylalkyl, 6-10C aryl, 7-11C arylalkyl or furfuryl radical, any of which may be substituted by 1 or 2 radicals selected from halogen atoms, and 1-6C alkyl, nitro, hydroxy, carboxy, 2-6C alkanoyloxy, 2-6C alkoxycarbonyl, 2-6C alkanoyl, 1-6C alkanesulphonyl, 1-6C alkoxysulphonyl, amino, 1-6 alkylamino and 2-6C alkanoylamino radicals or $R^{38}$ is a carbamoyl radical;

K. radicals of the formula $R^{39}$—Q—COO— in which Q is a direct bond, an oxygen or sulphur atom or an NH radical and $R^{39}$ is:
  (i) a hydrogen atom or a 1-6C alkyl radical which may be interrupted by an oxygen or sulphur atom or by an NH group or substituted by a cyano, carboxy, methoxycarbonyl, ethoxycarbonyl, hydroxy, carboxycarbonyl, halogen or amino radical;
  (ii) a 2-6C alkenyl radical which may be interrupted by an oxygen or sulphur atom or an NH group;
  (iii) a phenyl, hydroxyphenyl, chlorophenyl, fluorophenyl, tolyl, nitrophenyl, aminophenyl, methoxyphenyl, methylthiophenyl, thienyl, pyridyl, cyclohexyl, cyclopentyl, sydnonyl, naphthyl or ethoxynaphthyl radical;
  or (iv) $R^{40}$-$(CH_2)_g$ where $R^{40}$ has the value for $R^{39}$ listed in (i) above and g is 1 to 4;

$R^2$ is a carboxy radical;
$R^3$ is a hydrogen atom;
$X^1$ is a sulphur or oxygen atom;
$X^2$ is a nitrogen atom;
$R^4$ is hydrogen;
$R^6$ is hydrogen and $R^5$ is a 2-6C alkenyl, 2-10C alkanesulphonylaminoalkyl, 2-6C cyanoalkyl, 1-6C nitroalkyl, 2-6C alkanoylaminoalkyl, 3-8C haloalkanoylaminoalkyl, 3-8C alkylcarbamoyloxyalkyl, 2-6C ureidoalkyl, 3-15C heterocyclylcarbonylaminoalkyl or 4-15C heterocyclylalkylcarbonylaminoalkyl radical wherein the heterocyclic radical is a 5- or 6-membered aromatic or non-aromatic heterocyclic radical which contains 1, 2, 3 or 4 hetero atoms selected from oxygen, nitrogen and sulphur atoms, such ring optionally being in the form of the N-oxide and such ring being optionally fused with a benzene ring, and such fused benzene and/or heterocyclic ring being optionally substituted by one or two substituents selected from halogen atoms and 1-6C alkyl, hydroxy, 1-6C alkoxy, phenoxy, mercapto, 1-6C alkylthio, phenylthio, carboxy, 2-6C alkoxycarbonyl, phenoxycarbonyl, carbamoyl, 2-6C alkylcarbamoyl, 3-10C dialkylcarbamoyl, phenylcarbamoyl, diphenylcarbamoyl, nitro, amino, 1-6C alkylamino, 2-8C dialkylamino, phenylamino, 7-12C (phenyl(alkyl)amino, diphenylamino, carboxyamino, 2-6C (carboxy)(alkyl)amino, (carboxy)(phenyl)amino, 1-6C alkanoylamino, 2-10C (alkanoyl)(alkyl)amino, benzoylamino, 8-14C (benzoyl)-(alkyl)amino, cyano, phenyl, sulphamoyl, 1-6C alkylsulphamoyl, 2-10C dialkylsulphamoyl, phenylsulphamoyl, 1-6C haloalkyl, 1-6C aminoalkyl, 2-8C alkylaminoalkyl, 3-12C dialkylaminoalkyl, 2-6C carboxyalkyl and 1-6C sulphoalkyl radicals or $R^5$ is a radical of the formula:

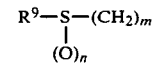

in which m is 1 to 6, n is 1 or 2 and $R^9$ is a 1-6C alkyl radical;

and, where the compound of the formula I contains a free basic or acidic group, the pharmaceutically-acceptable acid- or base-addition salts thereof.

2. A cephalosporin derivative as claimed in claim 1 in which $R^5$ is a vinyl, allyl, methanesulphonylaminomethyl, 2-(methanesulphonylamino)ethyl, 3-(methanesulphonylamino)-propyl, cyanomethyl, 2-cyanopropyl, 2-nitroethyl, methylcarbamoyloxymethyl, 3-(methylcarbamoyloxy)propyl, acetylaminomethyl, 2-acetylaminoethyl, 3-acetylaminopropyl, 2-trifluoroacetylaminoethyl, 3-trifluoroacetylaminopropyl, ureidomethyl, 3-ureidopropyl, 2-heterocyclylcarbonylaminoethyl or 3-heterocyclylcarbonylaminopropyl radical in which the heterocycle is a furan, thiophene, pyrrole, thiazole, imidazole, isoxazole, isothiazole, thiadiazole, oxadiazole, triazole, tetrazole, pyridine, pyrimidine, pyrazine, pyridazine or piperazine ring, such ring optionally being in the form of the N-oxide, such ring being optionally fused with a benzene ring and such fused benzene ring and/or heterocyclic ring being optionally substituted by one or two substituents selected from fluorine, chlorine and bromine atoms and methyl, ethyl, hydroxy, methoxy, phenoxy, mercapto, methylthio, phenylthio, carboxy, methoxycarbonyl, phenoxycarbonyl, carbamoyl, methylcarbamoyl, dimethylcarbamoyl, phenylcarbamoyl, diphenylcarbamoyl, nitro, amino, methylamino, dimethylamino, phenylamino (phenyl)(methyl)amino, diphenylamino, carboxyamino, (carboxy)(methyl)amino, (carboxy)(phenyl)amino, acetylamino, (acetyl)(methyl)amino, benzoylamino, (benzoyl)(methyl)amino, cyano, phenyl, sulphamoyl, methylsulphamoyl, dimethylsulphamoyl, phenylsulphamoyl, trifluoromethyl, 2,2,2-trifluoroethyl, 2-aminoethyl, 2-methylaminoethyl, 2-dimethylaminoethyl, 2-carboxyethyl and 2-sulphoethyl radicals, or $R^5$ is a radical of the formula II given in claim 1 in which m is 1, 2 or 3, n is 1 or 2 and $R^9$ is a methyl or ethyl radical.

3. A cephalosporin derivative as claimed in claim 1 in which $X^1$ is sulphur.

4. A cephalosporin derivative as claimed in claim 3 in which $R^5$ is allyl, 2-methanesulphonylaminoethyl, 3-methanesulphonylaminopropyl, cyanomethyl, 2-cyanoethyl, 2-nitroethyl, 3-ethanesulphinylpropyl, 3-ethanesulphonylpropyl or 2-(2-aminothiazol-4-ylacetylamino)ethyl.

5. A cephalosporin derivative as claimed in claim 3, in which $R^1$ is hydrogen, chlorine, methyl, hydroxymethyl, aminomethyl, azidomethyl, methoxymethyl, acetoxymethyl, benzoyloxymethyl, acetylaminomethyl, carbamoyloxymethyl, 1-methyl-1H-tetrazol-5-ylthiomethyl, 1-carboxymethyl-1H-tetrazol-5-ylthiomethyl, 1-(2-dimethylamino)ethyl-1H-tetrazol-5-ylthiomethyl, 1-sulphomethyl-1H-tetrazol-5-ylthiomethyl, 1-isopropyl-1H-tetrazol-5-ylthiomethyl, 1-(2,2,2-trifluoroethyl)-1H-tetrazol-5-ylthiomethyl, 1-phenyl-1H-tetrazol-5-ylthiomethyl, 1-(2-methylthioethyl)-1H-tetrazol-5-ylthiomethyl, 1,3,4-thiadiazol-2-ylthiomethyl, 5-methyl-1,3,4-thiadiazol-2-ylthiomethyl, 5-methylthio-1,3,4-thiadiazol-2-ylthiomethyl, 5-mercapto-1,3,4-thiadiazol-2-ylthiomethyl, 5-methyl-1,2,4-thiadiazol-3-ylthiomethyl, 5-acetamido-1,3,4-thiadiazol-2-ylthiomethyl, 1,2,3-thiadiazol-5-ylthiomethyl, 5-sulphomethyl-1,3,4-oxadiazol-2-ylthiomethyl, 1H-1,2,3-triazol-4-ylthiomethyl, 5-trifluoromethyl-1H-1,2,4-triazol-3-ylthiomethyl, 1H-1,2,4-triazol-3-ylthiomethyl, 2-methyl-2H-1,2,3-triazol-4-ylthiomethyl, 4-carboxymethyl-5-methylthiazol-2-ylthiomethyl, 4-(3-carboxypropyl)-5-methylthiazol-2-ylthiomethyl, 4,6-dimethylpyrimid-2-ylthiomethyl, 2-thiazolin-2-ylthiomethyl, benzoxazol-2-ylthiomethyl, benzthiazol-2-ylthiomethyl, 2-carboxyphenylthiomethyl, (6-carboxymethyl-7-hydroxypyrrolo[1,2-b]pyridazin-2-yl)thiomethyl, 4-methyl-6-hydroxy-5-oxodihydro-1,2,4-triazin-3-ylthiomethyl, 2-methyl-6-hydroxy-5-oxodihydro-1,2,4-triazin-3-ylthiomethyl, pyrid[2,3-imidazol-2-ylthiomethyl, pyrimid[4,5-c]imidazol-2-ylthiomethyl, 1-pyridiniomethyl, (1-oxido-2-pyridiniothiomethyl, 4,4-dimethyl-1-piperaziniothiocarbonylthiomethyl, tetrazol[4,5-b]pyridazin-6-ylthiomethyl, 8-aminotetrazol[4,5-b]pyridazin-6-ylthiomethyl, 4-(2-sulphoethyl)pyridiniomethyl or 6-hydroxypyridazin-3-ylthiomethyl.

6. A cephalosporin derivative selected from 7-(4-allylimidazol-2-yl)amino-3-(1-methyl-1H-tetrazol-5-yl)thiomethylceph-3-em-4-carboxylic acid, 7-(4-allylimidazol-2-yl)amino-3-(1H-1,2,3-triazol-4-yl)thiomethylceph-3-em-4-carboxylic acid, 7-(4-allylimidazol-2-yl)amino-3-(1,3,4-thiadiazol-2-yl)thiomethylceph-3-em-4-carboxylic acid, 7-(4-allylimidazol-2-yl)amino-3-chloroceph-3-em-4-carboxylic acid, 7-(4-cyanomethylimidazol-2-yl)amino-3-(1-methyl-1H-tetrazol-5-yl)thiomethylceph-3-em-4-carboxylic acid, 7-(4-cyanomethylimidazol-2-yl)amino-3-(1H-1,2,3-triazol-4-yl)thiomethylceph-3-em-4-carboxylic acid, 7-[4-(2-cyanomethyl)imidazol-2-yl]amino-3-(1-methyl-1H-tetrazol-5-yl)thiomethylceph-3-em-4-carboxylic acid, 7-[4-(2-methanesulphonylaminoethyl)imidazol-2-yl]amino-3-(1-methyl-1H-tetrazol-5-yl)thiomethylceph-3-em-4-carboxylic acid, 7-[4-(3-methanesulphonylaminopropyl)imidazol-2-yl]amino-3-acetoxymethylceph-3-em-4-carboxylic acid, 7-[4-(2-nitroethyl)imidazol-2-yl]amino-3-(1-methyl-1H-tetrazol-5-yl)thiomethylceph-3-em-4-carboxylic acid, 7-[4-(3-ethanesulphinylpropyl)imidazol-2-yl]amino-3-(1-methyl-1H-tetrazol-5-yl)thiomethylceph-3-em-4-carboxylic acid, 7-[4-(3-ethanesulphonylpropyl)imidazol-2-yl]amino-3-(1-methyl-1H-tetrazol-5-yl)thiomethylceph-3-em-4-carboxylic acid, 7-[4-(3-acetylaminopropyl)imidazol-2-yl]amino-3-(1-methyl-1H-tetrazol-5-yl)thiomethylceph-3-em-4-carboxylic acid, 3-acetoxymethyl-7-[4-(2-[2-aminothiazol-4-ylacetylamino]ethyl)imidazol-2-yl]aminoceph-3-em-4-carboxylic acid, 3-(1-methyl-1H-tetrazol-5-yl)thiomethyl-7-[4-(3-ureidopropyl)imidazol-2-yl]aminoceph-3-em-4-carboxylic acid and the pharmaceutically acceptable acid-addition salts and base-addition salts thereof.

7. A cephalosporin derivative according to claim 1, said derivative being 7-[4-(3-ethanesulphinylpropyl)imidazol-2-yl]amino-3-(1-methyl-1H-tetrazol-5-yl)thiomethylceph-3-em-4-carboxylic acid.

8. A pharmaceutical composition which comprises an effective amount of a cephalosporin derivative as claimed in claim 1 in association with a pharmaceutically-acceptable diluent or carrier.

9. A method of treating a bacterial infection in a warm-blooded animal which comprises administering to the animal a therapeutically effective amount of the compound of claim 1.

* * * * *